US007985353B2

(12) United States Patent
Leeming et al.

(10) Patent No.: US 7,985,353 B2
(45) Date of Patent: Jul. 26, 2011

(54) OLIGOMERIC IS POLYACENE AND SEMICONDUCTOR FORMULATIONS

(75) Inventors: Stephen William Leeming, Manchester (GB); Remi Manouk Anemian, Cheadle (GB); Richard Williams, Manchester (GB); Beverley Anne Brown, Warrington (GB)

(73) Assignee: Merck Patent GmbH, Darmstadt (DE)

( * ) Notice: Subject to any disclaimer, the term of this patent is extended or adjusted under 35 U.S.C. 154(b) by 699 days.

(21) Appl. No.: 11/915,061

(22) PCT Filed: Apr. 26, 2006

(86) PCT No.: PCT/EP2006/003889
§ 371 (c)(1),
(2), (4) Date: Nov. 20, 2007

(87) PCT Pub. No.: WO2006/125504
PCT Pub. Date: Nov. 30, 2006

(65) Prior Publication Data
US 2008/0197325 A1 Aug. 21, 2008

Related U.S. Application Data

(60) Provisional application No. 60/683,297, filed on May 23, 2005.

(30) Foreign Application Priority Data

May 21, 2005  (EP) ..................................... 05011063

(51) Int. Cl.
*H01B 1/00* (2006.01)
*C07C 49/00* (2006.01)
*C08G 2/00* (2006.01)

(52) U.S. Cl. .......................... 252/500; 568/303; 528/220
(58) Field of Classification Search .................. 252/500; 568/303; 528/220
See application file for complete search history.

(56) References Cited

U.S. PATENT DOCUMENTS

| 3,557,233 A | 1/1971 | Zwieg et al. |
| 3,751,246 A | 8/1973 | Printy et al. |
| 5,151,478 A * | 9/1992 | Chiang et al. .................. 526/258 |
| 5,635,308 A | 6/1997 | Inoue et al. |
| 6,203,933 B1 | 3/2001 | Nakaya et al. |
| 6,326,640 B1 | 12/2001 | Shi et al. |
| 6,690,029 B1 | 2/2004 | Anthony et al. |
| 6,864,396 B2 | 3/2005 | Smith et al. |

(Continued)

FOREIGN PATENT DOCUMENTS
CN 1821193 * 8/2006

(Continued)

OTHER PUBLICATIONS

Payne, M. et al., "Organic Field-Effect Transistors from Solution-Deposited Functionalized Acenes with Mobilities as High as 1 cm2/Vs," JACS, 127, pp. 4986-4987 (2005).*

(Continued)

*Primary Examiner* — Mark Kopec
*Assistant Examiner* — Jaison P Thomas
(74) *Attorney, Agent, or Firm* — Millen, White, Zelano & Branigan, P.C.

(57) ABSTRACT

The invention relates to novel oligomeric polyacene compounds, organic semiconducting formulations and layers comprising them, a process for preparing the formulation and layer and electronic devices, including organic field effect transistors (OFETs), comprising the same.

34 Claims, 2 Drawing Sheets

U.S. PATENT DOCUMENTS

| | | | |
|---|---|---|---|
| 6,998,068 B2 * | 2/2006 | Gerlach | 252/500 |
| 7,276,395 B2 * | 10/2007 | Gerlach | 438/99 |
| 7,495,251 B2 * | 2/2009 | Zhu et al. | 257/40 |
| 2003/0067005 A1 | 4/2003 | De Leeuw et al. | |
| 2003/0116755 A1 | 6/2003 | Takahashi | |
| 2003/0227014 A1 | 12/2003 | Murti et al. | |
| 2004/0038459 A1 | 2/2004 | Brown et al. | |
| 2005/0240061 A1 * | 10/2005 | Takahashi et al. | 568/306 |
| 2005/0258417 A1 | 11/2005 | Minakata | |
| 2007/0102696 A1 | 5/2007 | Brown et al. | |
| 2007/0232781 A1 * | 10/2007 | Zhu et al. | 528/373 |
| 2007/0238855 A1 * | 10/2007 | Li et al. | 528/380 |
| 2009/0163693 A1 * | 6/2009 | Kim | 528/212 |
| 2010/0019234 A1 * | 1/2010 | Saito et al. | 257/40 |

FOREIGN PATENT DOCUMENTS

| | | | |
|---|---|---|---|
| DE | 1 902 135 C3 | | 11/1974 |
| EP | 0 786 820 A2 | | 7/1998 |
| EP | 0 681 019 B1 | | 9/1999 |
| EP | 1 262 469 A1 | | 1/2005 |
| EP | 1 416 069 A1 | | 7/2007 |
| GB | 1258813 | * | 12/1971 |
| JP | 2004-107257 | * | 4/2004 |
| WO | WO 03 030278 A2 | | 4/2003 |

OTHER PUBLICATIONS

Ito, K et al., "Oligo(2,6-anthrylene)s: Acene-Oligomer Approach for Organic Field-Effect Transistors," Angew. Chem. Int. Ed., 42, No. 10, pp. 1159-1162 (2003).*

Tokito et al., "Acene containing polyfluorenes for red, green and blue emission in organic light-emitting diodes," Proceedings of SPIE, vol. 4105, pp. 69-74 (2001).*

Okamoto et al., "Synthesis of Solution-Soluble Pentacene-Containing Conjugated Copolymers," J. Am. Chem. Soc., 129, pp. 10308-10309 (2007).*

Lehnherr et al., "Pentacene Oligomers and Polymers: Functionalization of Pentacene to Afford Mono-, Di-, Tri- and Polymeric Materials," Org. Lett., 9 (22), pp. 4583-4586 (2007).*

T. Takahashi, et al.; "Straightforward Method for Synthesis of Highly Alkyl . . . "; J. Am. Chem. Soc.; 2000; pp. 12876-12877; vol. 122.

C. D. Sheraw, et al.; "Functionalized Pentacene Active Layer . . . "; Advanced Materials; 2003; pp. 2009-2011; vol. 15, No. 23.

O. Farooq; Oxidation of Aromatic 1,2-Dimethanols by Activated Dimethyl Sulfoxide; Synthesis; Oct. 1994; pp. 1035-1036.

D. H. Hua, et al., "Syntheses and Bioactivities of Substituted 9,10-Dihydro-9,10 . . . "; J. Org. Chem.; 2002; pp. 2907-2912; vol. 67.

D. Sparfel, et al.; "Transformations Thermiques des . . . "; Tetrahedron; 1980; pp. 2225-2235; vol. 36; Pergamon Press Ltd.

A. Maliakal, et al.; "Photochemical Stability of Pentacene and a Substituted . . . "; Chem. Mater.; 2004; pp. 4980-4986; vol. 16.

J. E. Anthony, et al.; "Functionalized Pentacene: Improved Electronic Properties . . . "; J. Amer. Chem. Soc.; 2001; pp. 9482-9483; vol. 123; XP008066070.

J. E. Anthony, et al., "A Road Map to Stable, Soluble Easily Crystallized Pentacene Derivatives"; Organic Letters; 2002; pp. 15-18; vol. 4, No. 1.

S. A. Odom, et al., "Tetracene Derivatives as Potential Red Emitters for Organics LEDs"; Organic Letters; 2003; pp. 4245-4248; vol. 5, No. 23.

M. M. Payne, et al., "Robust, Soluble Pentacene Ethers"; Organic Letters; 2004; pp. 1609-1612; vol. 6, No. 10.

M. M. Payne, et al.: "Stable, Crystalline Acenedithiophenes with up to Seven Linearly Fused Rings"; Organic Letters; 2004; pp. 3325-3328; vol. 6, No. 19.

M. M. Payne, et al.: "Functionalized Higher Acenes . . . "; J. Am. Chem. Soc.; 2005; pp. 4986-4987; vol. 127.

K. Ito, et al.; "Oligo(2,6-anthrylene)s: Acene-Oligomer . . . " Angew. Chem. Int. Ed.; 2003; pp. 1159-1162; vol. 42, No. 10; XP008066064.

M. M. Payne, et al.; "Organic Field Effect Transistors from Solution Deposited . . . " J. Am. Chem. Soc.; Mar. 19, 2005; pp. 4986-4987; vol. 127; XP008066061.

* cited by examiner

OLIGOMERIC IS POLYACENE AND SEMICONDUCTOR FORMULATIONS

This application claims the benefit of the filing date of U.S. Provisional Application Ser. No. 60/683,297, filed May 23, 2005.

FIELD OF THE INVENTION

The invention relates to novel oligomeric polyacene compounds, methods of their synthesis, organic semiconducting formulations and layers comprising them, a process for preparing the formulation and layer and electronic devices, including organic field effect transistors (OFETs), comprising the same.

BACKGROUND AND PRIOR ART

In recent years, there has been development of organic semiconducting materials in order to produce more versatile, lower cost electronic devices. Such materials find application in a wide range of devices or apparatus, including organic field effect transistors (OFETs), organic light emitting diodes (OLEDs), photodetectors, photovoltaic (PV) cells, sensors, memory elements and logic circuits to name just a few. The organic semiconducting materials are typically present in the electronic device in the form of a thin layer, for example less than 1 micron thick.

Pentacene has shown promise as an organic semiconducting material. Pentacene has been described as requiring a highly crystalline structure in order to provide a molecular orientation which results in good charge mobility. Thus, in the prior art, thin films of pentacene have been vapour deposited, due in part to the fact that pentacene is rather insoluble in common solvents. However, vapour deposition requires expensive and sophisticated equipment. In view of the latter problem, one approach has been to apply a solution containing a precursor pentacene and then chemically converting, for example by heat, the precursor compound into pentacene. However, the latter method is also complex and it is difficult to control in order to obtain the necessary ordered structure for good charge mobility.

Soluble pentacene compounds have recently been described in the prior art as organic semiconducting compounds, see for example US 2003/0116755 A and U.S. Pat. No. 6,690,029. The use of pentacenes in FETs has been suggested in WO 03/016599, in which a solution of a soluble pentacene is deposited on a substrate and the solvent evaporated to form a thin film of the pentacene. However, soluble pentacenes have been described in U.S. Pat. No. 6,690,029 and WO 03/016599 as still requiring a highly crystalline structure in the thin film for acceptable charge mobility, especially when used in FETs, which means that the pentacenes must still be deposited in a controlled way. Thus, the prior art is careful not to dilute the pentacene in any way, otherwise it would be expected to disrupt the crystalline structure of the pentacene and hence reduce charge mobility.

Improved charge mobility is one goal of new electronic devices. Another goal is improved stability, film uniformity and integrity of the organic semiconductor layer. One way potentially to improve organic semiconductor layer stability and integrity in devices would be to include the organic semiconducting component in an organic binder. However, whenever an organic semiconducting component is combined with a binder it is effectively "diluted" by the binder and a reduction of charge mobility is to be expected. Among other things, diluting an organic semiconductor by mixing with binders disrupts the molecular order in the semiconducting layer. Diluting an organic semiconducting component in the channel of an OFET for example is particularly problematic as any disruption of the orbital overlap between molecules in the immediate vicinity of the gate insulator (the first few molecular layers) is expected to reduce mobility. Electrons or holes are then forced to extend their path into the bulk of the organic semiconductor, which is undesirable. Certain organic semiconducting materials are expected to be more susceptible than others to the effects of use in a binder. Since pentacenes have been taught as requiring highly ordered structures for useful charge mobility, it has not previously been considered desirable to include pentacenes with binders. In WO 03/030278 it is attempted to use binders but there it is shown that a gradual reduction of FET mobility occurs when a (precursor) pentacene is mixed with increasing amounts of binder, even with amounts of less than 5% binder.

Certain low polarity binder resins are described in WO 02/45184 for use with organic semiconductors in FETs. However, a reduction in charge mobility is still expected when the semiconductor is diluted in the binder.

One aim of the present invention is to reduce or overcome the disadvantages in organic semiconducting layers as described above. Other aims of the present invention are immediately evident to the expert from the following detailed description.

It was now found that these aims can be achieved by providing semiconducting materials, formulations and methods as claimed in the present invention. Furthermore it was found that, when oligomeric polyacenes are provided in a formulation together with an organic binder, improved semiconducting materials with good processibility are obtained which do still show a surprisingly high charge carrier mobility.

WO 2005/055248 A2 relates to a semiconductor formulation comprising an organic binder and a polyacene, but does not disclose the materials claimed in the present invention.

SUMMARY OF THE INVENTION

The invention relates to compounds of formula I (oligomeric polyacenes)

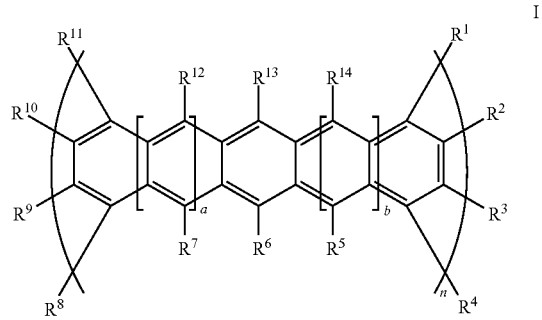

I
wherein
a is in case of multiple occurrence independently of one another 0, 1, 2 or 3,
b is in case of multiple occurrence independently of one another 0, 1, 2 or 3,
n is an integer $\geq 2$, preferably 2, 3, 4, 5, 6, 7, 8, 9 or 10,
$R^{1-14}$ denote, in case of multiple occurrence independently of one another, identical or different groups selected from H, halogen, —CN, —NC, —NCO, —NCS, —OCN, —SCN, —C(=O)NR⁰R⁰⁰, —C(=O)X, —C(=O)R⁰, —NH₂, —NR⁰R⁰⁰, —SH, —SR⁰, —SO₃H, —SO₂R⁰, —OH, —NO₂, —CF₃, —SF₅, optionally substituted silyl, or carbyl or hydrocarbyl with 1 to 40 C atoms that is optionally substituted and optionally comprises one or more hetero atoms, $R^{1-4}$ and $R^{8-11}$ can also denote a linkage to an adjacent polyacene unit, wherein said linkage is a single bond or optionally contains a spacer group, X is halogen, $R^0$ and $R^{00}$ are independently of each other H or an optionally substituted carbyl or hydrocarbyl group optionally comprising one or more hetero atoms, optionally two or more of the substituents $R^1$-$R^{14}$ which are located on adjacent ring positions of the polyacene or which are located on adjacent polyacene units, constitute a further saturated, unsaturated or aromatic ring system having 4 to 40 C atoms, which is monocyclic or polycyclic, is fused to the polyacene, is optionally intervened by one or more groups selected from —O—, —S— and —N(R⁰)—, and is optionally substituted by one or more identical or different groups $R^1$, optionally one or more of the carbon atoms in the polyacene skeleton or in the rings formed by $R^{1-14}$ are replaced by a heteroatom selected from N, P, As, O, S, Se and Te, wherein the n polyacene units are identical or different from each other, and a polyacene unit is linked to its adjacent polyacene unit(s) via one of $R^{1-4}$ and/or one of $R^{8-11}$ and/or a polyacene unit is fused to its adjacent polyacene unit(s) via two of $R^{1-4}$ and/or two of $R^{8-11}$.

The invention further relates to the use of compounds of formula I as charge carrier materials and organic semiconductors.

The invention further relates to an organic semiconducting formulation comprising one or more compounds of formula I, one or more organic polymers or organic polymeric binders, or precursors thereof, and optionally one or more solvents.

The invention further relates to an organic semiconducting formulation comprising one or more compounds of formula I, one or more organic binders, or precursors thereof, having a permittivity ∈ at 1,000 Hz of 3.3 or less, and optionally one or more solvents.

The invention further relates to an organic semiconducting layer comprising a compound of formula I or an organic semiconducting formulation as described above and below.

The invention further relates to a process for preparing an organic semiconducting layer as described above and below, comprising the following steps
(i) depositing on a substrate a liquid layer of a formulation which comprises one or more compounds of formula I, one or more organic binders or precursors thereof, and optionally one or more solvents,
(ii) forming from the liquid layer a solid layer which is the organic semiconducting layer,
(iii) optionally removing the layer from the substrate.

The invention further relates to the use of the compounds, formulations and layers as described above and below in an electronic, optical or electrooptical component or device.

The invention further relates to an electronic, optical or electrooptical component or device comprising one or more compounds, formulations or layers as described above and below.

Said electronic, optical or electrooptical component or device includes, without limitation, an organic field effect transistor (OFET), thin film transistor (TFT), component of integrated circuitry (IC), radio frequency identification (RFID) tag, organic light emitting diode (OLED), electroluminescent display, flat panel display, backlight, photodetector, sensor, logic circuit, memory element, capacitor, photovoltaic (PV) cell, charge injection layer, Schottky diode, planarising layer, antistatic film, conducting substrate or pattern, photoconductor, and electrophotographic element.

DETAILED DESCRIPTION OF THE INVENTION

Figure 1:
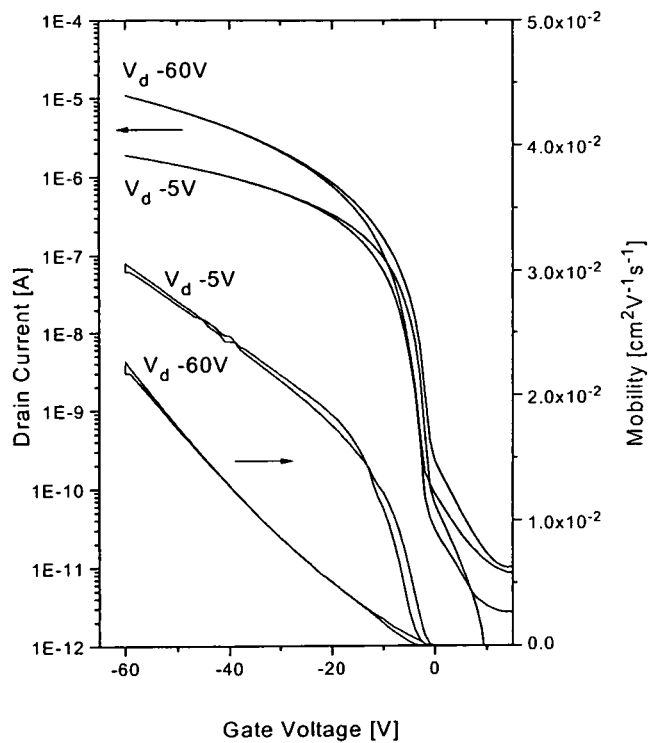
FIGS. 1 to 4 show the current-voltage and mobility-voltage characteristics for materials according to examples 1 to 4.

Formula I also includes "mixed" oligomers, for example of the type A-B-A, A-B-B-A, where A is a polyacene and B is a conjugated or non-conjugated, cyclic spacer group Z.

Unless stated otherwise, substituents and substitution positions (like $R^1$, $R^2$ etc.) in the pentacenes as shown above and below and in the polyacenes of formula I refer to the conventional nomenclature of pentacene as shown below:

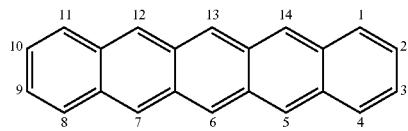

Unless stated otherwise, groups like $R^1$, $R^2$ etc., or indices like k etc., in case of multiple occurrence are selected independently from each other, and may be identical or different from each other. Thus, several different groups might be represented by a single label like for example '$R^5$'.

The terms 'alkyl', 'aryl' etc. also include multivalent species, for example alkylene, arylene etc. The term 'aryl' or 'arylene' means an aromatic hydrocarbon group or a group derived from an aromatic hydrocarbon group. The term 'heteroaryl' or 'heteroarylene' means an 'aryl' or 'arylene' group comprising one or more hetero atoms.

The term 'carbyl group' as used above and below denotes any monovalent or multivalent organic radical moiety which comprises at least one carbon atom either without any non-carbon atoms (like for example —C≡C—), or optionally combined with at least one non-carbon atom such as N, O, S, P, Si, Se, As, Te or Ge (for example carbonyl etc.). The terms 'hydrocarbon group', and 'hydrocarbyl group' denote a carbyl group that does additionally contain one or more H atoms and optionally contains or more hetero atoms like for example N, O, S, P, Si, Se, As, Te or Ge.

A carbyl or hydrocarbyl group comprising a chain of 3 or more C atoms may also be linear, branched and/or cyclic, including spiro and/or fused rings.

Preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40, very preferably 7 to 25 C atoms.

The carbyl or hydrocarbyl group may be a saturated or unsaturated acyclic group, or a saturated or unsaturated cyclic group. Unsaturated acyclic or cyclic groups are preferred, especially alkenyl and alkynyl groups (especially ethynyl). Where the $C_1$-$C_{40}$ carbyl or hydrocarbyl group is acyclic, the group may be linear or branched. The $C_1$-$C_{40}$ carbyl or hydrocarbyl group includes for example: a $C_1$-$C_{40}$ alkyl group, a $C_2$-$C_{40}$ alkenyl group, a $C_2$-$C_{40}$ alkynyl group, a $C_3$-$C_{40}$ alkyl group, a $C_4$-$C_{40}$ alkyldienyl group, a $C_4$-$C_{40}$ polyenyl group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_2$-$C_{20}$ alkenyl group, a $C_2$-$C_{20}$ alkynyl group, a $C_3$-$C_{20}$ alkyl group, a $C_4$-$C_{20}$ alkyldienyl group, a $C_6$-$C_{12}$ aryl group and a $C_4$-$C_{20}$ polyenyl group, respectively; more preferred are a $C_1$-$C_{10}$ alkyl group, a $C_2$-$C_{10}$ alkenyl group, a $C_2$-$C_{10}$ alkynyl group (especially ethynyl), a $C_3$-$C_{10}$ alkyl group, a $C_4$-$C_{10}$ alkyldienyl group, a $C_6$-$C_{12}$ aryl group and a $C_4$-$C_{10}$ polyenyl group, respectively; and most preferred is $C_{2-10}$ alkynyl.

Further preferred carbyl and hydrocarbyl groups include straight-chain, branched or cyclic alkyl with 1 to 40, preferably 1 to 25 C-atoms, which is unsubstituted, mono- or polysubstituted by F, Cl, Br, I or CN, and wherein one or more non-adjacent $CH_2$ groups are optionally replaced, in each case independently from one another, by —O—, —S—, —NH—, —NR$^0$—, —SiR$^0$R$^{00}$—, —CO—, —COO—, —OCO—, —O—CO—O—, —S—CO—, —CO—S—, —CO—NR$^0$—, —NR$^0$—CO—, —NR$^0$—CO—NR$^{00}$—, —CX$^1$=CX$^2$— or —C≡C— in such a manner that O and/or S atoms are not linked directly to one another, with R$^0$ and R$^{00}$ having one of the meanings given as described above and below and X$^1$ and X$^2$ being independently of each other H, F, Cl or CN.

R$^0$ and R$^{00}$ are preferably selected from H, straight-chain or branched alkyl with 1 to 12 C atoms or aryl with 6 to 12 C atoms.

Halogen is F, Cl, Br or I.

Preferred alkyl groups include, without limitation, methyl, ethyl, propyl, n-butyl, t-butyl, dodecanyl, trifluoromethyl, perfluoro-n-butyl, 2,2,2-trifluoroethyl, benzyl, 2-phenoxyethyl, etc.

Preferred alkynyl groups include, without limitation, ethynyl and propynyl.

Preferred aryl groups include, without limitation, phenyl, 2-tolyl, 3-tolyl, 4-tolyl, naphthyl, biphenyl, 4-phenoxyphenyl, 4-fluorophenyl, 3-carbomethoxyphenyl, 4-carbomethoxyphenyl, etc.

Preferred alkoxy groups include, without limitation, methoxy, ethoxy, 2-methoxyethoxy, t-butoxy, etc.

Preferred aryloxy groups include, without limitation, phenoxy, naphthoxy, phenylphenoxy, 4-methylphenoxy, etc.

Preferred amino groups include, without limitation, dimethylamino, methylamino, methylphenylamino, phenylamino, etc.

If two or more of the substituents $R^1$-$R^{12}$ together with the polyacene form a ring system, this is preferably a 5-, 6- or 7-membered aromatic or heteroaromatic ring, preferably selected from pyridine, pyrimidine, thiophene, selenophene, thiazole, thiadiazole, oxazole and oxadiazole, especially preferably thiophene or pyridine.

The optional substituents on the ring groups and on the carbyl and hydrocarbyl groups for $R^1$ etc. include, without limitation, silyl, sulpho, sulphonyl, formyl, amino, imino, nitrilo, mercapto, cyano, nitro, halogen, $C_{1-12}$ alkyl, $C_{6-12}$ aryl, $C_{1-12}$ alkoxy, hydroxy and/or combinations thereof. These optional groups may comprise all chemically possible combinations in the same group and/or a plurality (preferably two) of the aforementioned groups (for example amino and sulphonyl if directly attached to each other represent a sulphamoyl radical).

Preferred substituents include, without limitation, F, Cl, Br, I, —CN, —NO$_2$, —NCO, —NCS, —OCN, —SCN, —C(=O)NR$^0$R$^{00}$, —C(=O)X, —C(=O)R$^0$, —NR$^0$R$^{00}$, —OH, —SF$_5$, wherein R$^0$, R$^{00}$ and X are as defined above, optionally substituted silyl, aryl with 1 to 12, preferably 1 to 6 C atoms, and straight chain or branched alkyl, alkoxy, alkylcarbonyl, alkoxycarbonyl, alkylcarbonyloxy or alkoxycarbonyloxy with 1 to 12, preferably 1 to 6 C atoms, wherein one or more H atoms are optionally replaced by F or Cl.

Examples for these preferred substituents are F, Cl, $CH_3$, $C_2H_5$, $C(CH_3)_3$, $CH(CH_3)_2$, $CH_2CH(CH_3)C_2H_5OCH_3$, $OC_2H_5$, $COCH_3$, $COC_2H_5$, $COOCH_3$, $COOC_2H_5$, $CF_3$, $OCF_3$, $OCHF_2$ and $OC_2F_5$.

Very preferred optional substituents comprise optionally substituted silyl, amino, F, Cl, $CH_3$, $C_2H_5$, $C(CH_3)_3$, $CH(CH_3)_2$ and $CH_2CH(CH_3)C_2H_5$.

The silyl group is optionally substituted and is preferably selected of the formula —SiR'R"R'". Therein, each of R', R" and R'" are identical or different groups selected from H, a $C_1$-$C_{40}$-alkyl group, preferably $C_1$-$C_4$-alkyl, most preferably methyl, ethyl, n-propyl or isopropyl, a $C_6$-$C_{40}$-aryl group, preferably phenyl, a $C_6$-$C_{40}$-arylalkyl group, a $C_1$-$C_{40}$-alkoxy group, or a $C_6$-$C_{40}$-arylalkyloxy group, wherein all these groups are optionally substituted for example with one or more halogen atoms. Preferably, R', R" and R'" are each independently selected from optionally substituted $C_{1-10}$-alkyl, more preferably $C_{1-4}$-alkyl, most preferably $C_{1-3}$-alkyl, for example isopropyl, and optionally substituted $C_{6-10}$-aryl, preferably phenyl. Further preferred is a silyl group of formula —SiR'R"" wherein R"" forms a cyclic silyl alkyl group together with the Si atom, preferably having 1 to 8 C atoms.

In one preferred embodiment of the silyl group, R', R" and R'" are identical groups, for example identical, optionally substituted, alkyl groups, as in triisopropylsilyl. Very preferably the groups R', R" and R'" are identical, optionally substituted $C_{1-10}$, more preferably $C_{1-4}$, most preferably $C_{1-3}$ alkyl groups. A preferred alkyl group in this case is isopropyl.

A silyl group of formula —SiR'R"R'" or —SiR'R"" as described above is a preferred optional substituent for the $C_1$-$C_{40}$-carbyl or hydrocarbyl group.

Preferred groups —SiR'R"R'" include, without limitation, trimethylsilyl, triethylsilyl, tripropylsilyl, dimethylethylsilyl, diethylmethylsilyl, dimethylpropylsilyl, dimethylisopropylsilyl, dipropylmethylsilyl, diisopropylmethylsilyl, dipropylethylsilyl, diisopropylethylsilyl, diethylisopropylsilyl, triisopropylsilyl, trimethoxysilyl, triethoxysilyl, triphenylsilyl, diphenylisopropylsilyl, diisopropylphenylsilyl, diphenylethylsilyl, diethylphenylsilyl, diphenylmethylsilyl, triphenoxysilyl, dimethylmethoxysilyl, dimethylphenoxysilyl, methylmethoxyphenylsilyl, etc., wherein the alkyl, aryl or alkoxy group is optionally substituted.

In some cases it may be desirable to control the solubility of the semiconducting compounds of formula I in common organic solvents in order to make devices easier to fabricate. This may have advantages in making an FET for example, where solution coating, say, a dielectric onto the semiconducting layer may have a tendency to dissolve the semiconductor. Also, once a device is formed, a less soluble semiconductor may have less tendency to "bleed" across organic layers. In one embodiment of a way to control solubility of the semiconducting compounds of formula I above, the compounds comprise silyl groups —SiR'R"R'" wherein at least one of R', R" and R'" contains an optionally substituted aryl, preferably phenyl, group. Thus, at least one of R', R" and R'"

may be an optionally substituted $C_{6-18}$ aryl, preferably phenyl, group, an optionally substituted $C_{6-18}$ aryloxy, preferably phenoxy, group, an optionally substituted $C_{6-20}$ arylalkyl, for example benzyl, group, or an optionally substituted $C_{6-20}$ arylalkyloxy, for example benzyloxy, group. In such cases, the remaining groups, if any, among R', R" and R'" are preferably $C_{1-10}$, more preferably $C_{1-4}$, alkyl groups which are optionally substituted.

Formula I covers any type of 1,1'-, 1,2'- and 2,2'-linked and any type of 1,2-1',2'-, 1,2-2',3'- and 2,3-2',3'-fused oligomeric polyacenes. Some preferred dimers and trimers are shown below in subformulae IA1, IB1 (1,1'-linked), IA2, IB2 (2,2'-linked), IA3, IB3 (1,2'-linked), IA4, IB4 (2,3-2',3'-fused)), IA5, IB5 (1,2-2',3'-fused), IA6, IB6 (1,2-1',2'-fused).

Further covered are oligomeric polyacenes with "mixed type" linkages, i.e. comprising two or more of 1,1'-linked, 1,2'-linked and 2,2'-linked polyacene units, or comprising two or more of 1,2-1',2'-fused, 2,3-2',3'-fused and 1,2-2',3'-fused polyacene units, like the trimers of preferred subformula I7 (2,3-2',3'-fused and 1,2-2',3'-fused). These units can appear in alternating or random sequence.

Further covered are oligomeric polyacenes with "mixed type" linkages comprising one or more of 1,1'-linked, 1,2'-linked and 2,2'-linked polyacene units and further comprising one or more of 1,2-1',2'-fused, 2,3-2',3'-fused and 1,2-2',3'-fused polyacene units, either in alternating or random sequence.

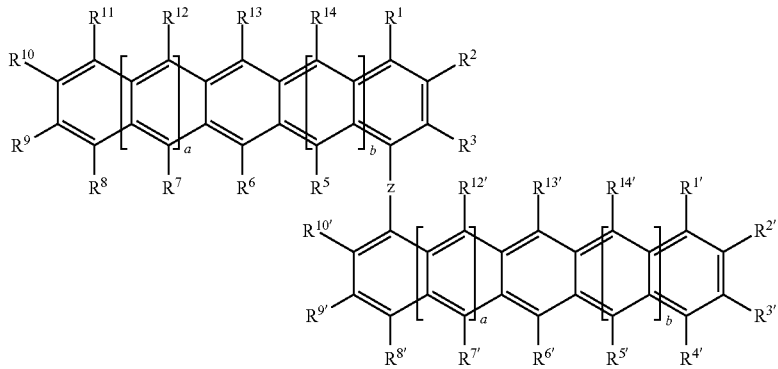

IA1

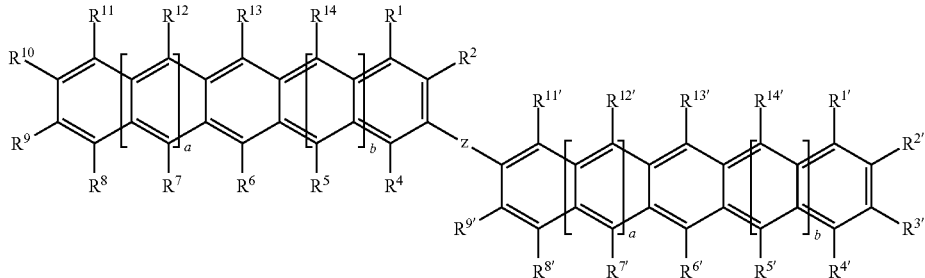

IA2

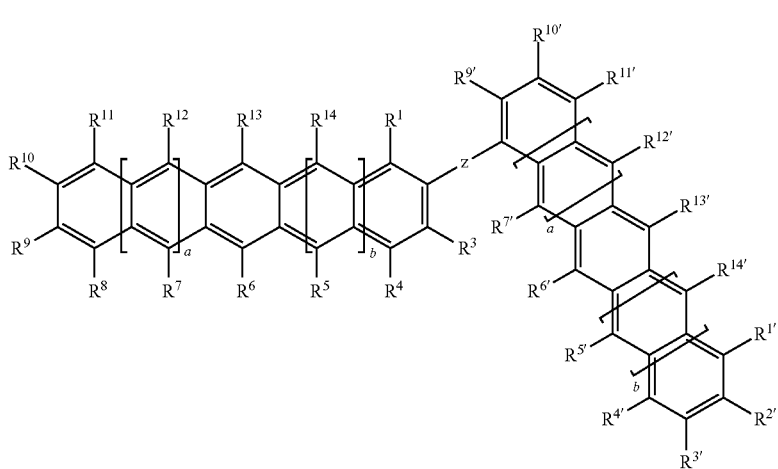

IA3

-continued
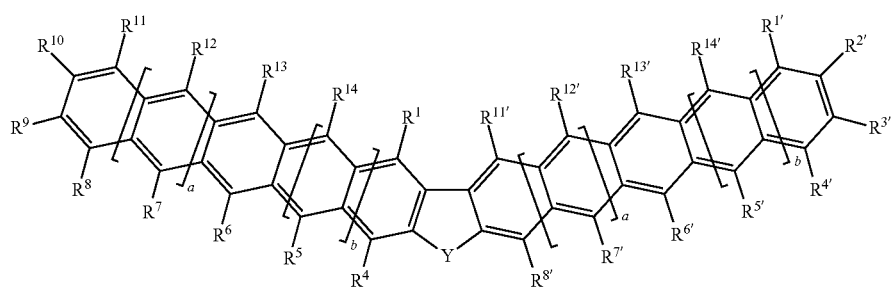
IA4
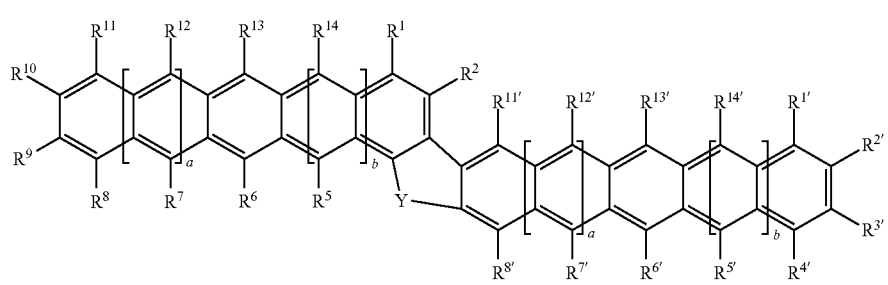
IA5
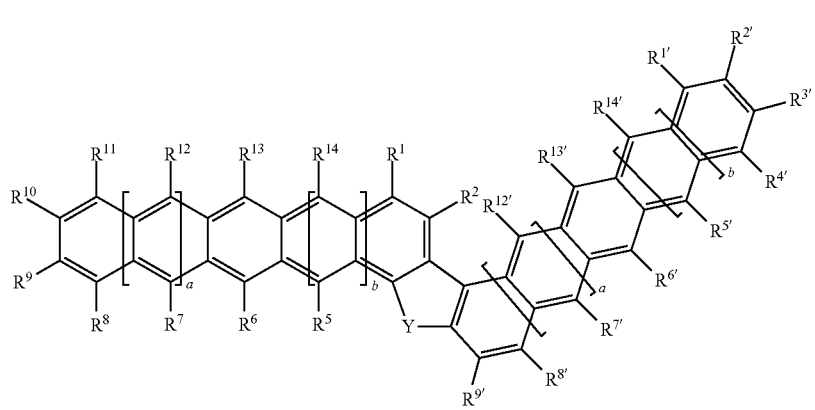
IA6
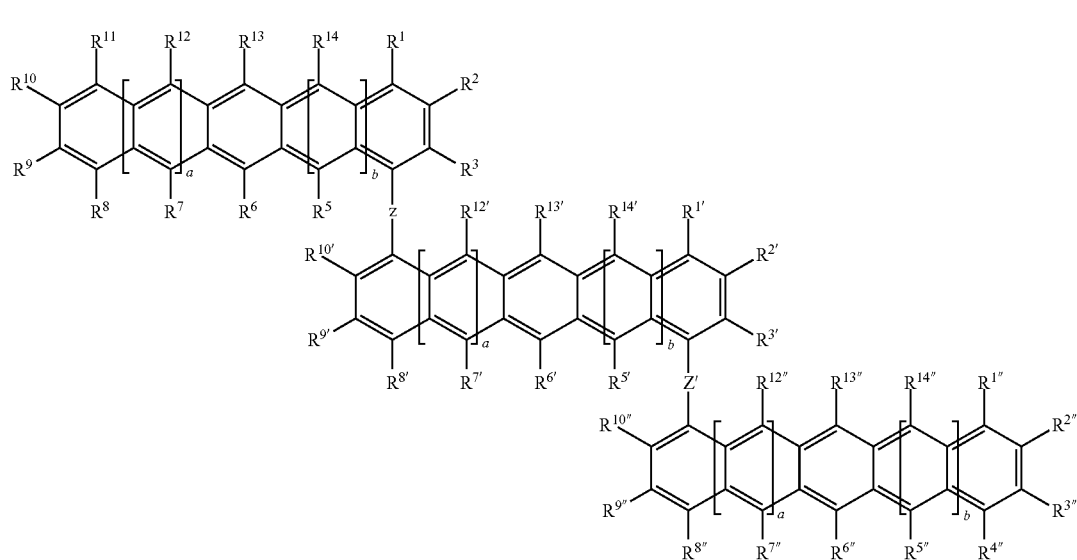
IB1

-continued
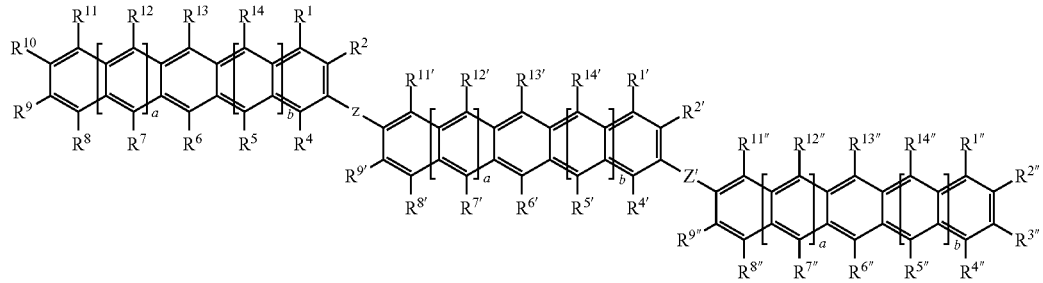
IB2
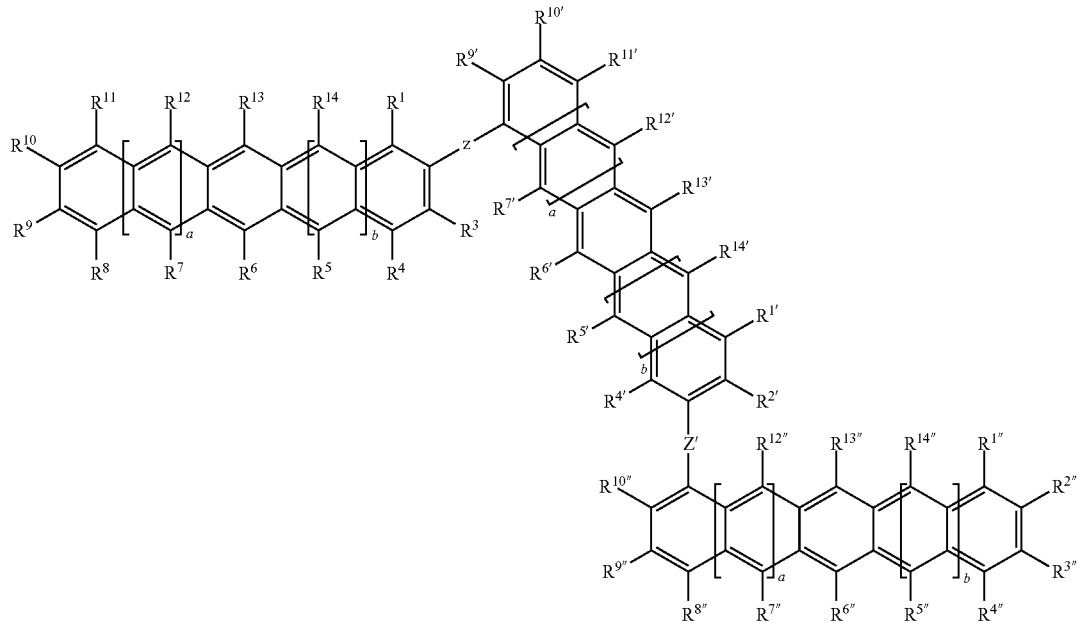
IB3
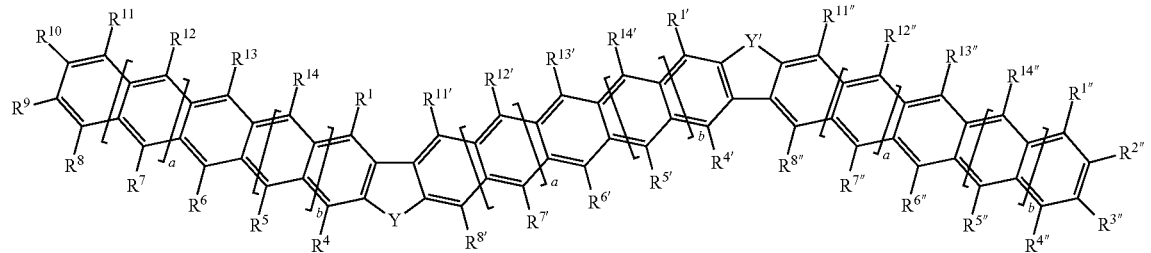
IB4
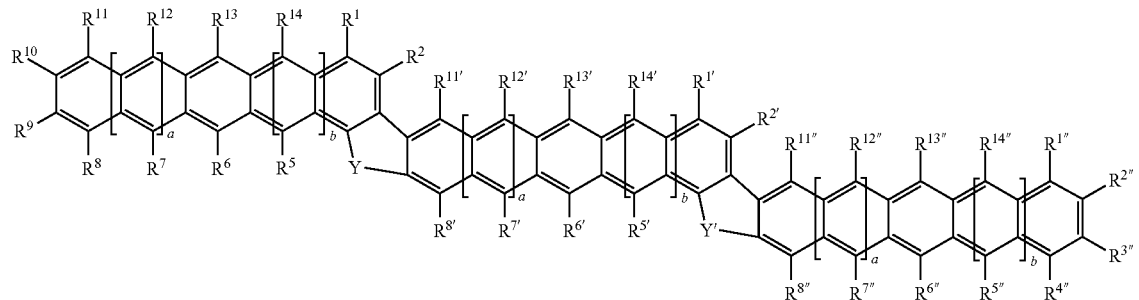
IB5

-continued

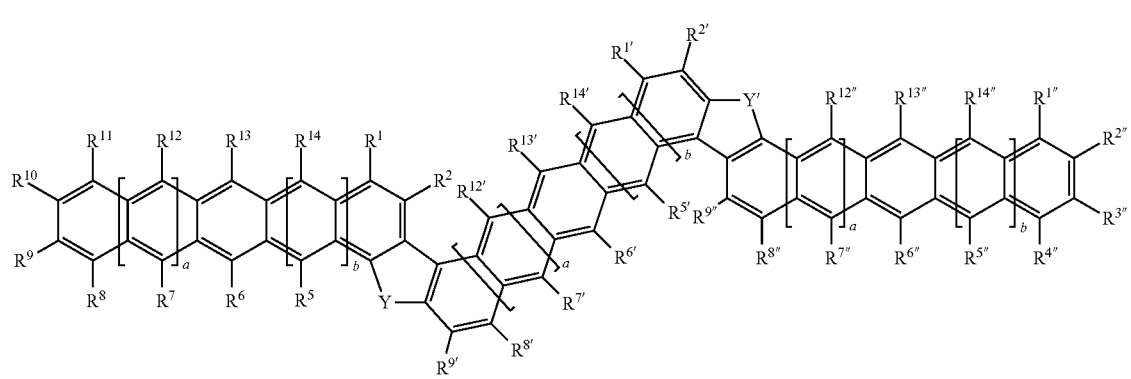

IB6

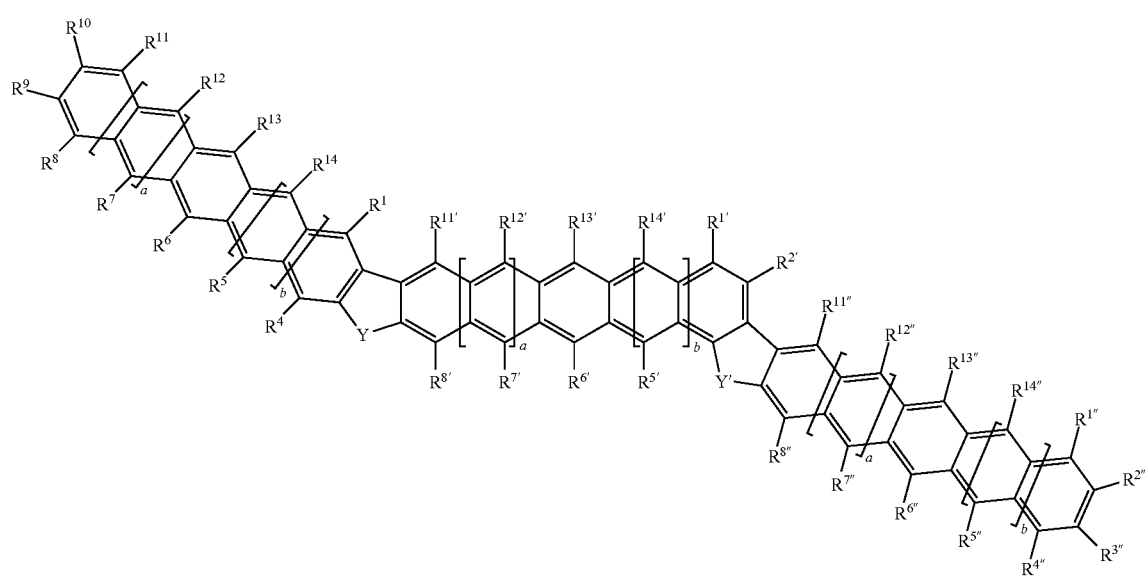

IB7 wherein a, b, $R^{1-14}$ are as defined in formula I, $R^{1'-14'}$ and $R^{1''-14''}$ have independently of each other one of the meanings of $R^1$, Z, Z' are independently of each other a single bond or a spacer group, Y, Y' are independently of each other $-(CH_2)_k-$, $-CR^{15}=CR^{16}-$, $-O-$, $-S-$, $-CR^{16}=N-$ or $-N(R^0)-$, $R^{15}$, $R^{16}$ have independently of each other one of the meanings of $R^1$, $R^0$ is as defined in formula I, k is 1, 2 or 3.

Especially preferred are the following compounds of formulae I and I1-I8:

n is 2 or 3, a is 0 and b is 0, a is 0 and b is 1, a is 1 and b is 1, both $R^6$ and $R^{13}$ and/or both $R^{6'}$ and $R^{13'}$ and/or both $R^{6''}$ and $R^{13''}$ denote $-C\equiv C-MR'R''R'''$ or $-C\equiv C-MR'R''''$, wherein M is Si or Ge and R', R'', R''' and R'''' are as defined above, the group $-C\equiv C-MR'R''R'''$ is $-C\equiv C-SiR_3$, wherein R is straight-chain, branched or cyclic $C_{1-12}$-alkyl or $C_{1-12}$-alkoxy, or optionally substituted monocyclic, polycyclic or fused aryl having 5 to 12 C atoms, both $R^9$ and $R^{10}$ and/or both $R^2$ and $R^3$ and/or both $R^{2'}$ and $R^{3'}$ and/or both $R^{2''}$ and $R^{3''}$ together with the respective polyacene unit form a 5-, 6- or 7-membered aromatic or heteroaromatic ring, preferably selected from pyridine, pyrimidine, thiophene, selenophene, thiazole, thiadiazole, oxazole and oxadiazole, especially preferably selected from the following groups or their mirror images (wherein the asterisks denote the positions where the respective group is fused to the polyacene)

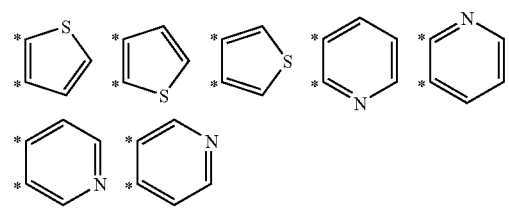

all substitutents are H, except for $R^{6,6',6'',13,13',13''}$ and the linkage groups, Z and Z' are selected from a single bond, $-O-$, monocyclic or polycyclic aryl or heteroaryl that is optionally substituted, straight-chain or branched alkylene, alkyleneoxy or alkylenedioxy that is optionally fluorinated, or a combination of the aforementioned groups, very preferably a single bond, —O—, —C(CF$_3$)$_2$— or 4,4'-isopropylidenediphenoxy, Y and Y' are independently of each other —O—, —S— or —NR$^0$—, The spacer group or group Z or Z' is preferably selected from a) straight-chain, branched or cyclic alkylene with 1 to 20 C atoms which is optionally mono- or poly-substituted by F, Cl, Br, I or CN, and wherein one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, b) mono- or polycyclic aryl or heteroaryl with 1 to 40 C atoms which is optionally mono- or polysubstituted by one or more groups R$^1$ as defined in formula I, c) —O—, —S—, —CO—, —COO—, —OCO—, —O—COO—, —CO—NR$^0$—, —NR$^0$—CO—, —NR$^0$—CO—NR$^{00}$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CX$^1$=CX$^2$—, —C≡C—, —CH=CH—COO—, —OCO—CH=CH—, wherein R$^0$ and R$^{00}$ have the meanings given in formula I and X$^1$ and X$^2$ are selected from H, F, Cl and CN, d) a combination of one or more groups selected from a), b) and c).

If Z comprises aryl or heteroaryl, it preferably comprises a 5-, 6- or 7-membered aromatic or heteroaromatic ring or two such rings which are linked directly to each other or fused to each other, preferably selected from phenylene, pyridine, pyrimidine, thiophene, selenophene, thiazole, thiadiazole, oxazole and oxadiazole, all of which are optionally substituted.

Especially preferred are the following compounds

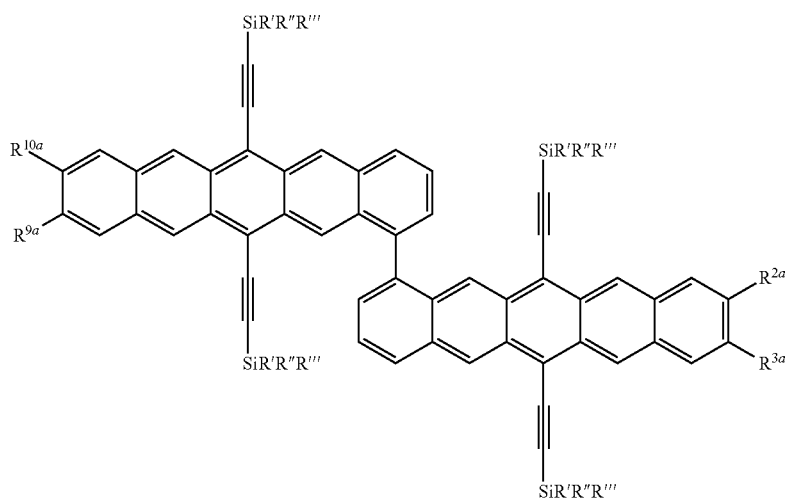

IA1a

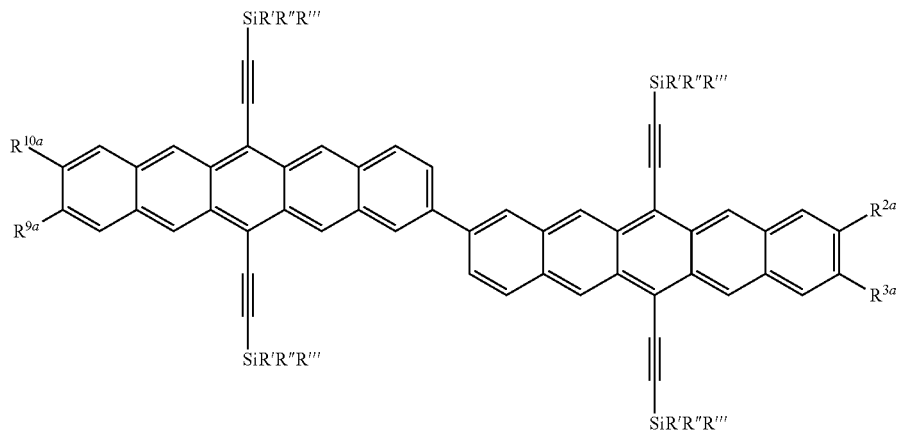

IA2a

IA2b
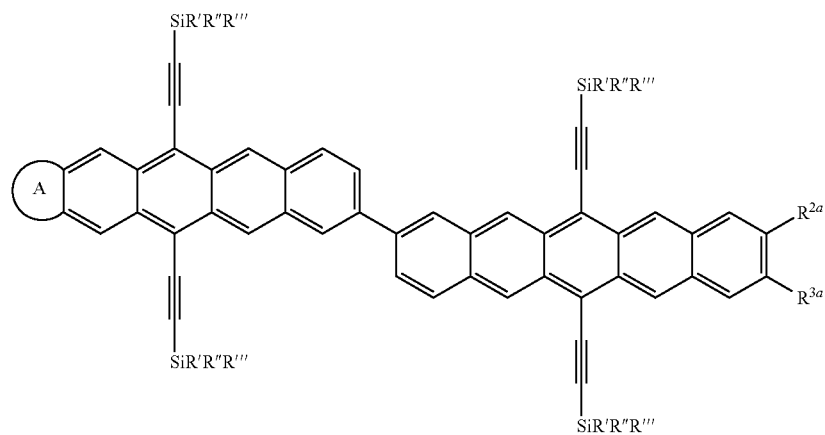
IA2c
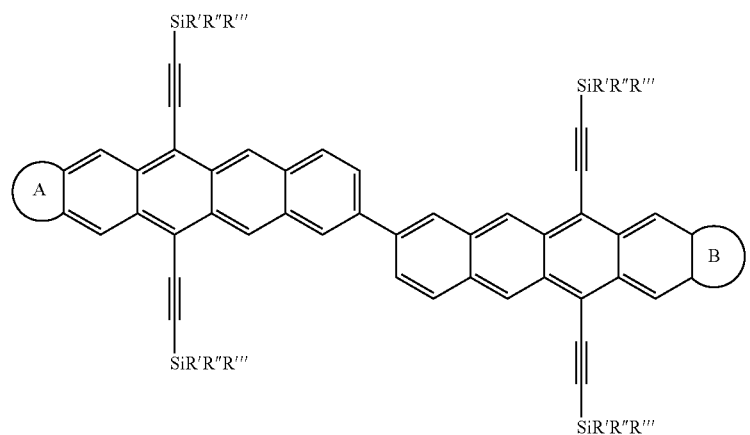
IA2d
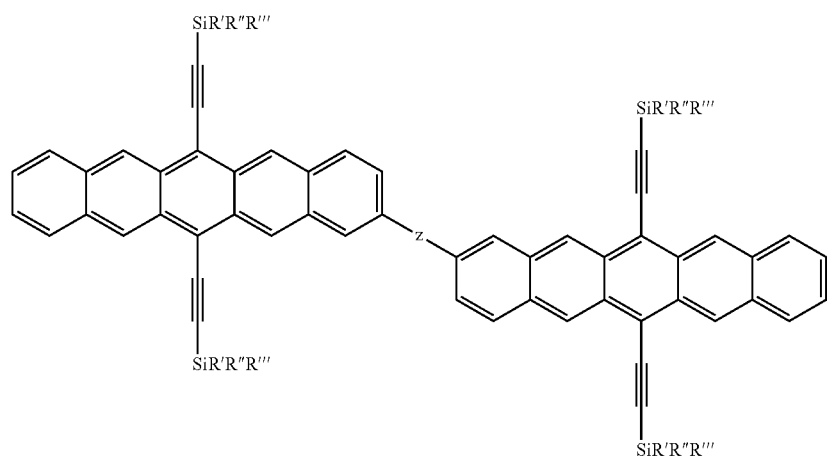

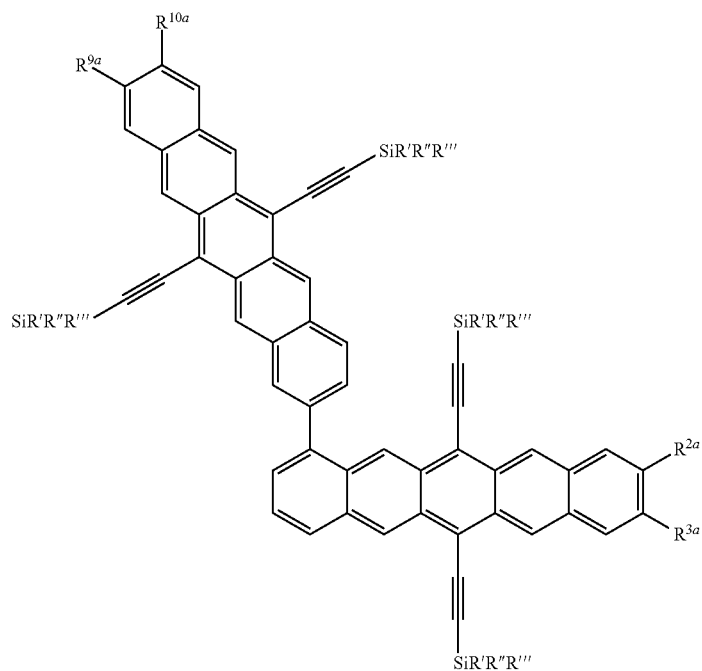
IA3a
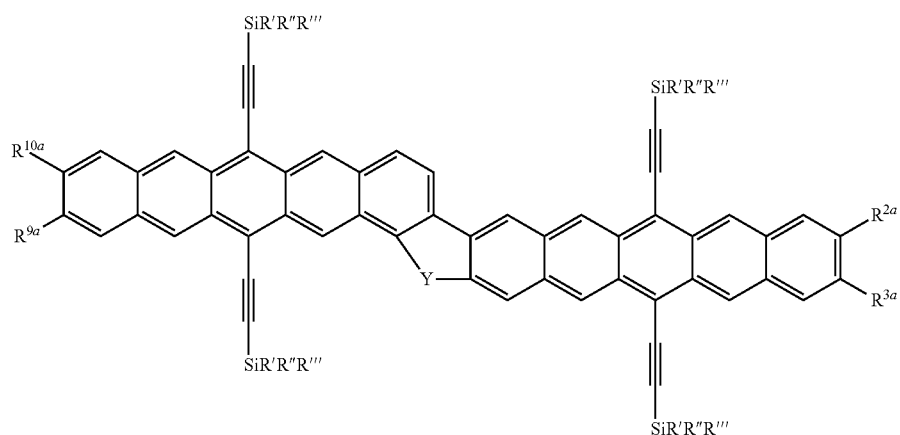
IA5a
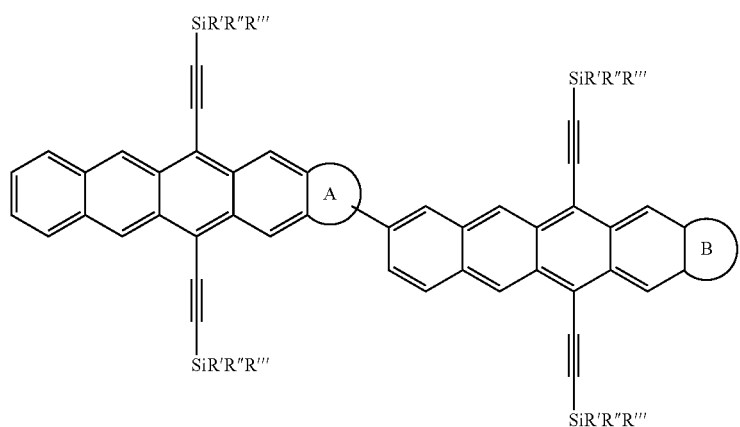
IA7a

-continued
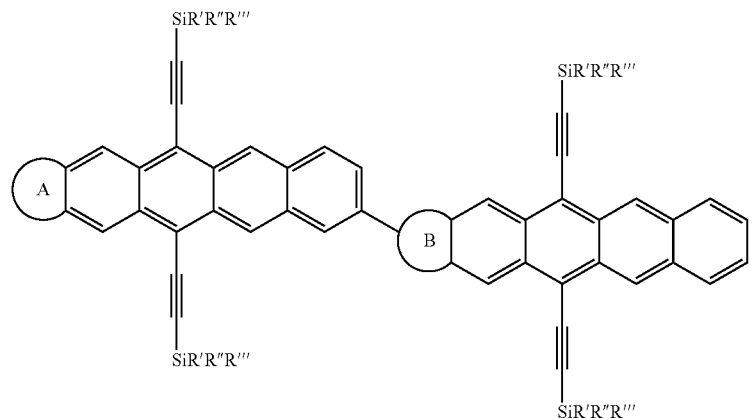
IA8a
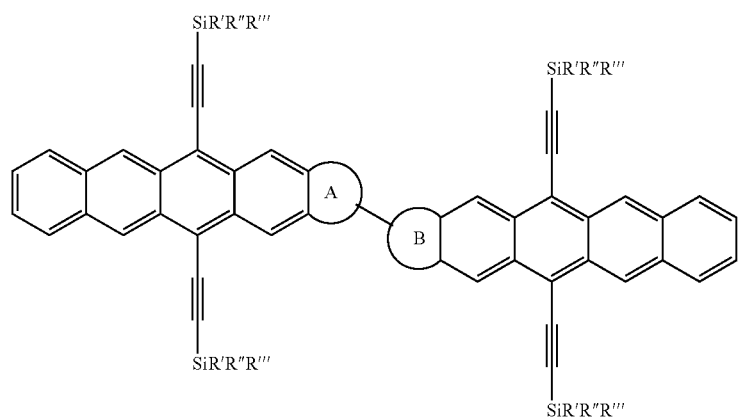
IA9a
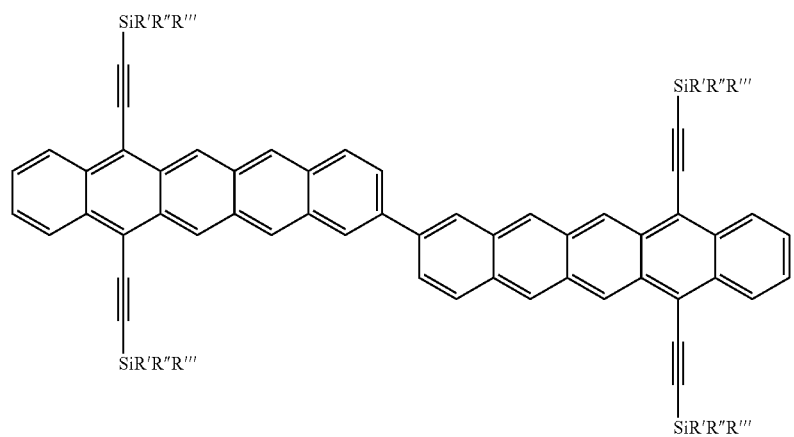
IA10a

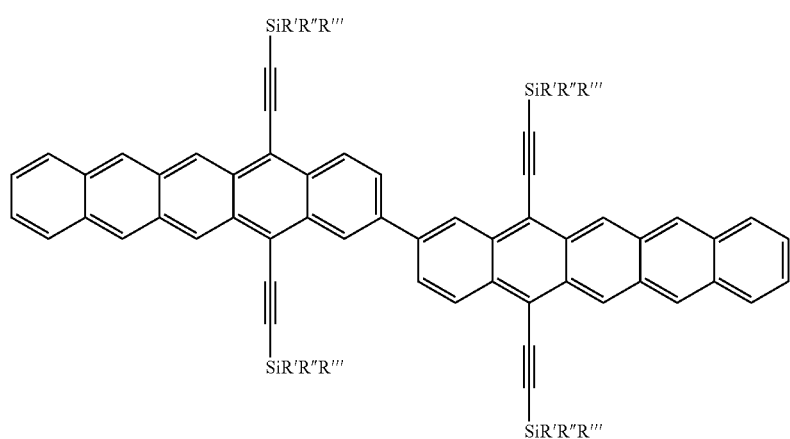

IA11a wherein Z, Y, R', R" and R'" are as defined above,
R$^{2a,3a,9a,10a}$ have one of the meanings of R$^1$ as given above and below,
A and B are independently of each other an unsaturated or aromatic ring system having 4 to 40 C atoms, which is monocyclic or polycyclic, is fused to the polyacene, is optionally intervened by one or more groups selected from —O—, —S—, =N— and —N(R$^0$)—, and is optionally substituted by one or more identical or different groups R$^1$,
R$^0$ is as defined in formula I,
and the phenylene rings are optionally substituted by one or more groups R$^1$ as defined in formula I.

Very preferred are compounds of the following subformulae

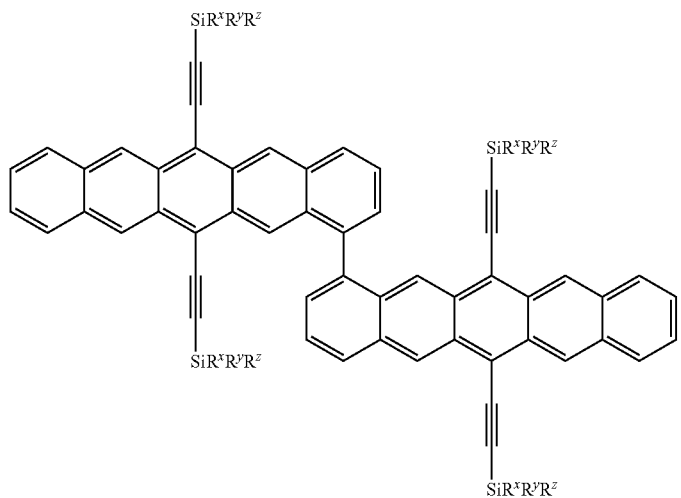

IA1a1

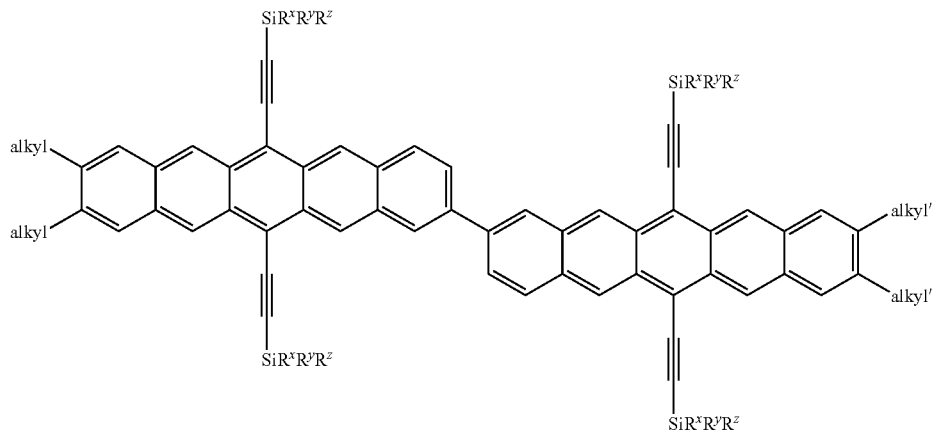

IA2a1

-continued
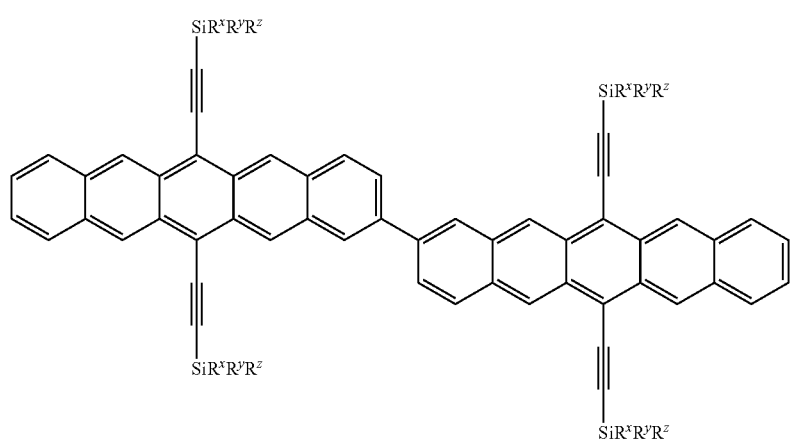
IA2a2
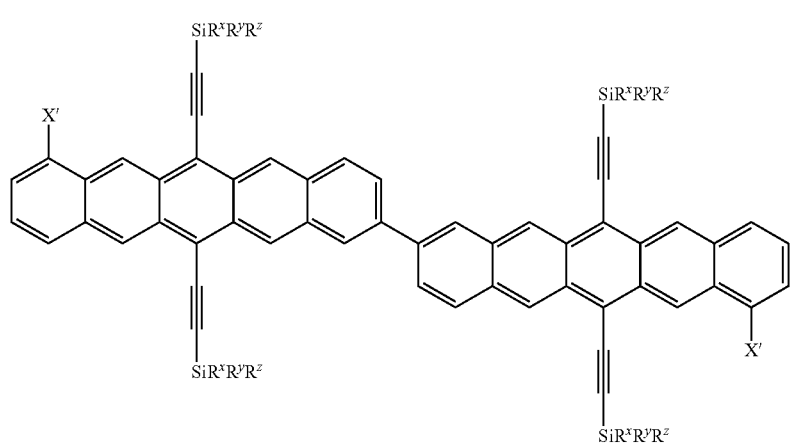
IA2a3
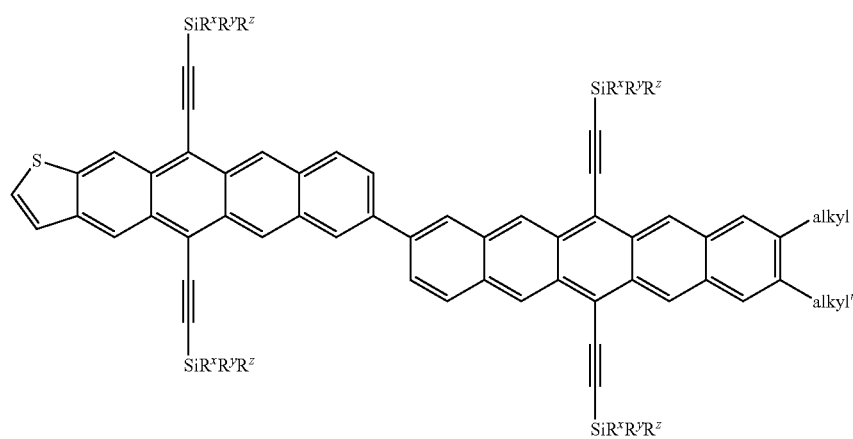
IA2b1
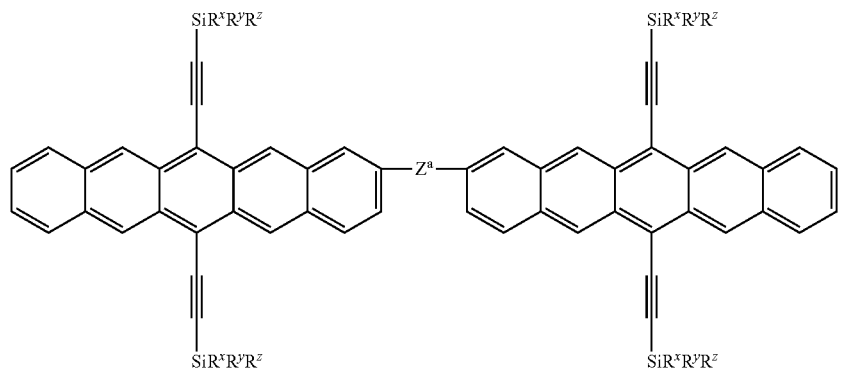
IA2d1

-continued
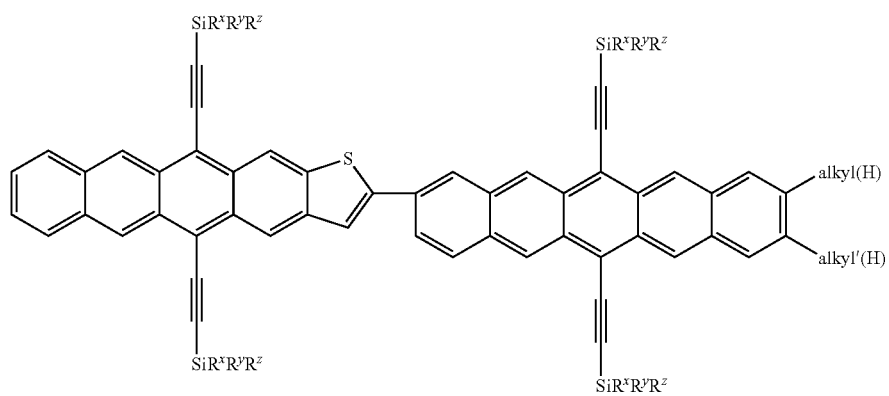
IA7a1
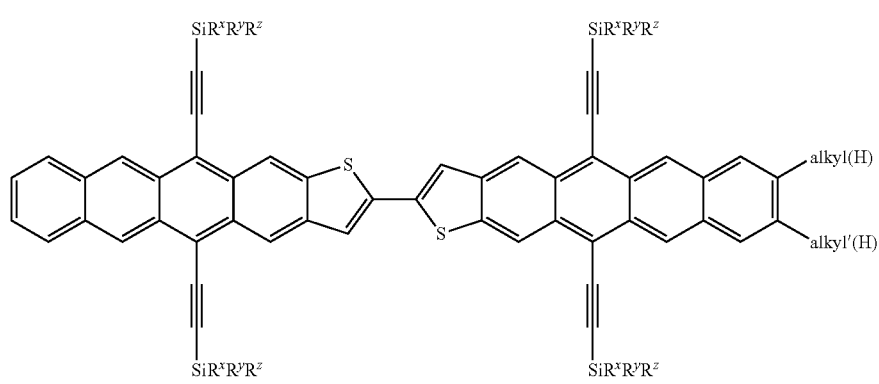
IA7a3
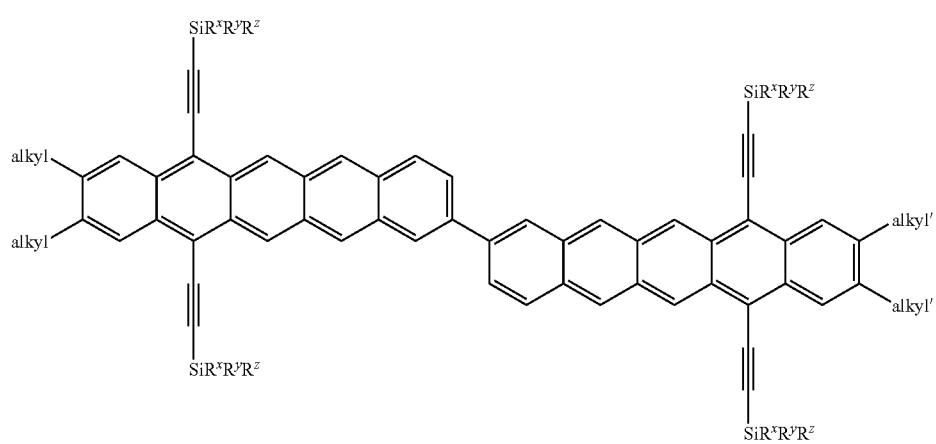
IA10a1
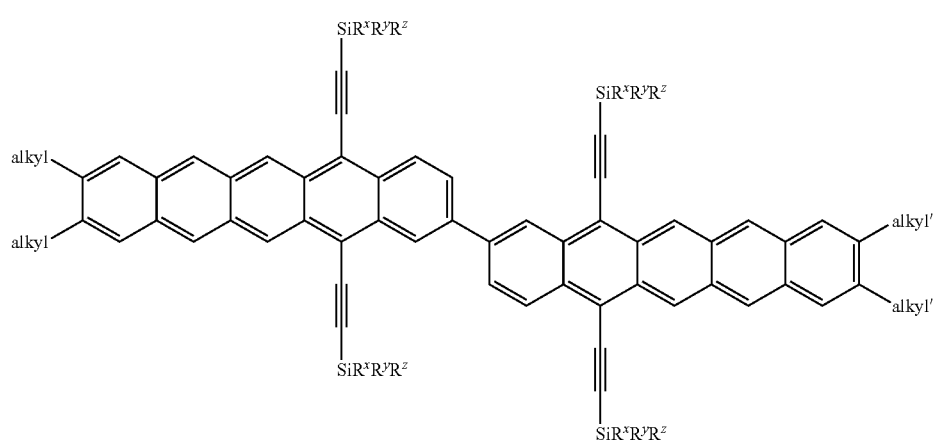
IA11a1 wherein

X' is halogen, preferably F, $Z^a$ has one of the meanings of Z as given above, and is preferably —O—, —C(CF$_3$)$_2$— or

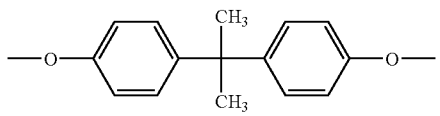

$R^x$, $R^y$ and $R^z$ are identical or different straight-chain or branched alkyl or alkoxy with 1 to 12 C atoms that is optionally fluorinated, or aryl, aryloxy or arylalkyl with 6 to 18 C atoms that is optionally substituted, alkyl and alkyl' are straight-chain or branched alkyl or alkoxy with 1 to 12 C atoms that is optionally fluorinated.

The compounds of the present invention can be synthesized according to or in analogy to known methods or to the methods described below. Further methods can be taken from the examples.

Certain polyacene compounds have been described in US 2003/0116755 A and U.S. Pat. No. 6,690,029 and the methods disclosed therein for synthesizing polyacenes may be employed in the present invention in order to make the polyacene compounds described herein. Methods for making polyacenes are also described in U.S. Pat. No. 3,557,233. Alternatively, methods within the skill and knowledge of persons skilled in the art which may be used to synthesize polyacene compounds in accordance with the present invention are disclosed in Organic Letters 2004, Volume 6, number 10, pages 1609-1612.

Compounds of formula I can for example be synthesised according to or in analogy to the method of preparing the pentacene dimer 2-(6,13-bis(triisopropylsilylethynyl)pentacenyl)-6,13-bis(triisopropylsilylethynyl)pentacene 6 as shown below (wherein R is alkyl, for example isopropyl):

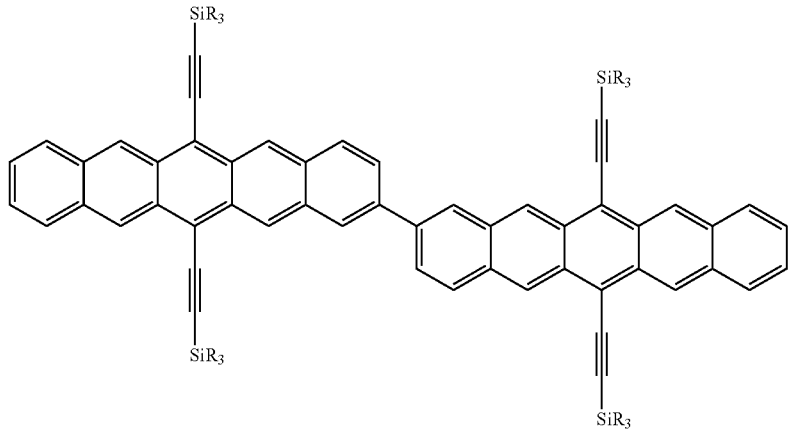

6

The silylethynylated pentacene dimer derivative 6 is obtained from its corresponding acene quinone 5 according to published procedures (see C. D. Sheraw, T. N. Jackson, D. L. Eaton, J. E. Anthony, *Adv. Mater.* 2003, 23, 2009-2011), as shown in Scheme 1.

Scheme 1:

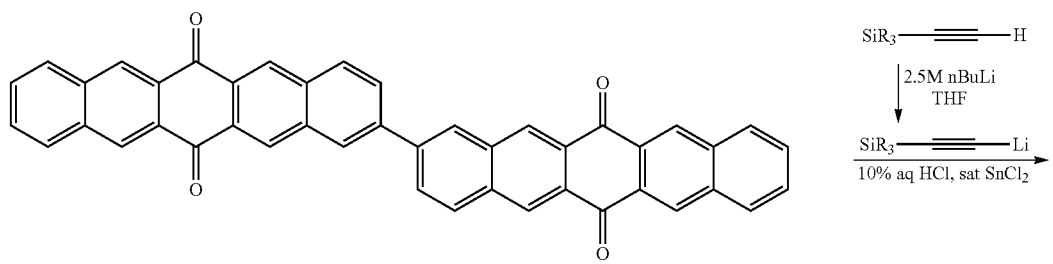

5

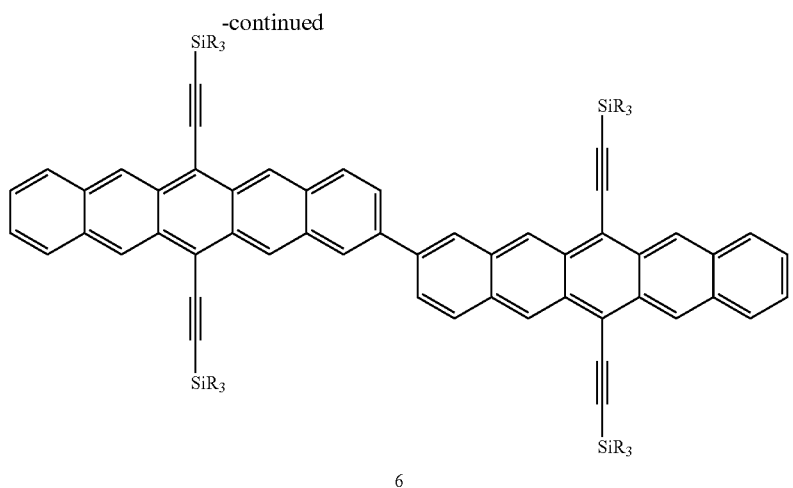

6

The acene quinone 5 is synthesised from an aldol condensation of the 1,4-dihydroxyanthracene 2 with the 1,1'-biphenyl-3,3',4,4'-tetracarboxaldehyde 4 as shown in Scheme 2.

Scheme 2

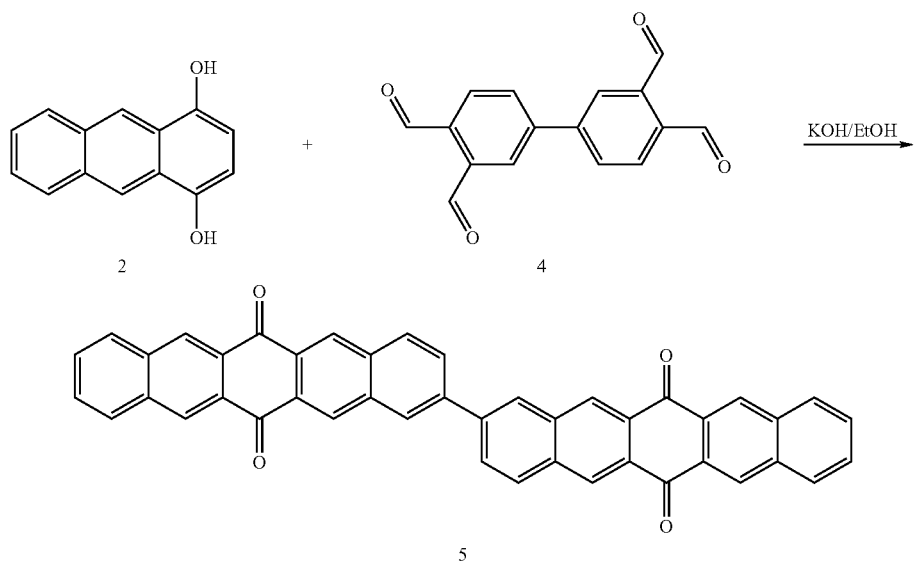

Compound 2 is prepared from commercially available quinizarin according to literature methods (see D. H. Hua, M. Tamura, X. Huang, H. A. Stephany, B. A. Helfrich, E. M. Perchellet, B. J. Sperfslage, J.-P. Perchellet, S. Jiang, D. E. Kyle, P. K. Chiang, *J. Org. Chem.*, 2002, 2907-2912) as shown in Scheme 3.

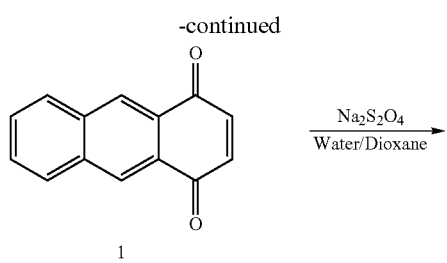

Scheme 3

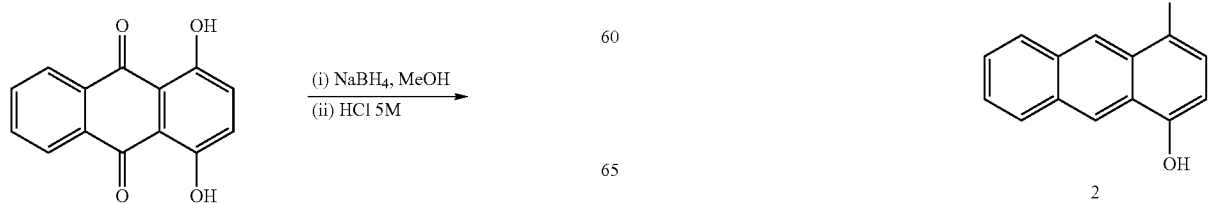

Compound 4 is prepared in two steps from commercially available 3,3',4,4'-biphenyltetracarboxylic dianhydride as shown in Scheme 4. Dianhydride is reduced with lithium aluminium hydride in dioxane to give 3,3',4,4'-tetra(hydroxymethyl)-1,1'-biphenyl 3, which is in turn oxidised following a standard swern oxidation procedure to afford tetracarbaldehyde 4.

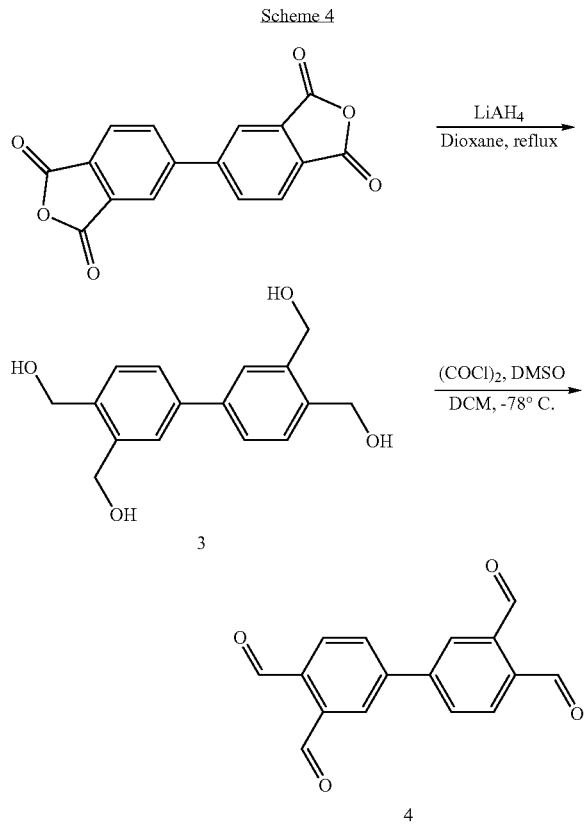

Surprisingly and beneficially, it has been found in accordance with the present invention that combining specified soluble polyacene compounds of formula I (hereinafter also referred to as "the polyacene"), especially compounds of the preferred formulae as described above and below, with an organic binder resin (hereinafter also referred to as "the binder") results in little or no reduction in charge mobility of the polyacene, even an increase in some instances. For instance, the soluble polyacene may be dissolved in a binder resin (for example poly(α-methylstyrene)) and deposited (for example by spin coating), to form an organic semiconducting layer yielding a high charge mobility, of for example 0.1-1.5 $cm^2V^{-1}s^{-1}$. This result is particularly unexpected given that the prior art teaches that in order to achieve such high mobilities a polyacene compound is expected to require strong molecular ordering. In FETs dilution in a binder would be expected to yield at least an order of magnitude reduction in mobility. It has also now been found that surprisingly even at a 1:1 ratio of binder:polyacene the mobility is comparable to that of a pure polyacene compound used alone. The results produced by the present invention are therefore surprising for both a) maintaining the mobility despite potential disruption of molecular order, and b) maintaining mobility despite the expected increase of intermolecular distance. At the same time, a semiconducting layer formed therefrom exhibits excellent film forming characteristics and is particularly stable.

Once an organic semiconducting layer formulation of high mobility is obtained by combining a polyacene with a binder, the resulting formulation leads to several other advantages. For example, since the polyacenes are soluble they may be deposited in a liquid form, for example from solution. With the additional use of the binder it has now been found that the formulation may be coated onto a large area in a highly uniform manner. Without the use of binders the polyacene cannot be spin coated onto large areas as it does not result in uniform films. In the prior art, spin and drop-casting of a pure polyacene layer may in some cases result in relatively high mobility, however, it is difficult to provide a large area film with a constant mobility over the entire substrate which is a specific requirement for electronic devices. Furthermore, when a binder is used in the formulation it is possible to control the properties of the formulation to adjust to printing processes, for example viscosity, solid content, surface tension. Whilst not wishing to be bound by any particular theory it is also anticipated that the use of a binder in the formulation fills in volume between crystalline grains otherwise being void, making the organic semiconducting layer less sensitive to air and moisture. For example, layers formed according to the process of the present invention show very good stability in OFET devices in air.

The invention also provides an organic semiconducting layer which comprises the organic semiconducting layer formulation.

The invention further provides a process for preparing an organic semiconducting layer, said process comprising the following steps:
(i) depositing on a substrate a liquid layer of a formulation comprising one or more compounds of formula I as described above and below, one or more organic binder resins or precursors thereof, and optionally one or more solvents,
(ii) forming from the liquid layer a solid layer which is the organic semiconducting layer,
(iii) optionally removing the layer from the substrate.

The process is described in more detail below.

The invention additionally provides an electronic device comprising the said organic semiconducting layer. The electronic device may include, without limitation, an organic field effect transistor (OFET), organic light emitting diode (OLED), photodetector, sensor, logic circuit, memory element, capacitor or photovoltaic (PV) cell. For example, the active semiconductor channel between the drain and source in an OFET may comprise the layer of the invention. As another example, a charge (hole or electron) injection or transport layer in an OLED device may comprise the layer of the invention. The formulations according to the present invention and layers formed therefrom have particular utility in OFETs especially in relation to the preferred embodiments described herein.

In a preferred embodiment of the present invention the semiconducting compound of formula I has a charge carrier mobility, μ, of more than $10^{-5}$ $cm^2V^{-1}s^{-1}$, preferably of more than $10^{-4}$ $cm^2V^{-1}s^{-1}$, more preferably of more than $10^{-3}$ $cm^2V^{-1}s^{-1}$, still more preferably of more than $10^{-2}$ $cm^2V^{-1}s^{-1}$ and most preferably of more than $10^{-1}$ $cm^2V^{-1}s^{-1}$.

The formulation according to the present invention may be a blend comprising one or more oligomeric polyacene(s) of formula I and further comprising one or more polymers or polymeric binders, preferably synthetic organic polymer(s), like for example thermoplastic polymers, thermosetting polymers, duromers, elastomers, conductive polymers, engineering plastics etc. The polymer may also be a copolymer.

Examples of a thermoplastic polymer include a polyolefin such as polyethylene, polypropylene, polycycloolefin, ethylene-propylene copolymer, etc., polyvinyl chloride, polyvinylidene chloride, polyvinyl acetate, polyacrylic acid, polymethacrylic acid, polystyrene, polyamide, polyester, polycarbonate, etc. Examples of a thermosetting polymer include a phenol resin, a urea resin, a melamine resin, an alkyd resin, an unsaturated polyester resin, an epoxy resin, a silicone resin, a polyurethane resin, etc. Examples of an engineering plastic include polyimide, polyphenylene oxide, polysulfone, etc. The synthetic organic polymer can also be a synthetic rubber such as styrene-butadiene, etc., or a fluoro resin such as polytetrafluoroethylene, etc. The conductive polymers include conjugated polymers such as polyacetylene, polypyrrole, polyallylenevinylene, polythienylenevinylene, etc. and those in which electron-donating molecules or electron-accepting molecules are doped.

The binder is typically a polymer and may comprise either an insulating binder or a semiconducting binder, or mixtures thereof. These are referred to herein as 'the organic binder', 'the polymeric binder' or simply 'the binder'.

Preferred binders according to the present invention are materials of low permittivity, that is, those having a permittivity ∈ at 1,000 Hz of 3.3 or less. The organic binder preferably has a permittivity ∈ at 1,000 Hz of 3.0 or less, more preferably 2.9 or less. Preferably the organic binder has a permittivity ∈ at 1,000 Hz of 1.7 or more. It is especially preferred that the permittivity of the binder is in the range from 2.0 to 2.9. Whilst not wishing to be bound by any particular theory it is believed that the use of binders with a permittivity ∈ of greater than 3.3 at 1,000 Hz, may lead to a reduction in the OSC layer mobility in an electronic device, for example an OFET. In addition, high permittivity binders could also result in increased current hysteresis of the device, which is undesirable.

An example of a suitable organic binder is polystyrene. Further examples are given below.

In one type of preferred embodiment, the organic binder is one in which at least 95%, more preferably at least 98% and especially all of the atoms consist of hydrogen, fluorine and carbon atoms.

It is preferred that the binder normally contains conjugated bonds, especially conjugated double bonds and/or aromatic rings.

The binder should preferably be capable of forming a film, more preferably a flexible film. Polymers of styrene and α-methyl styrene, for example copolymers including styrene, α-methylstyrene and butadiene may suitably be used.

Binders of low permittivity of use in the present invention have few permanent dipoles which could otherwise lead to random fluctuations in molecular site energies. The permittivity ∈ (dielectric constant) can be determined by the ASTM D150 test method.

It is also preferred that in the present invention binders are used which have solubility parameters with low polar and hydrogen bonding contributions as materials of this type have low permanent dipoles. A preferred range for the solubility parameters ('Hansen parameter') of a binder for use in accordance with the present invention is provided in Table 1 below.

TABLE 1

| | Hansen parameter | | |
|---|---|---|---|
| | $\delta_d$ MPa$^{1/2}$ | $\delta_p$ MPa$^{1/2}$ | $\delta_h$ MPa$^{1/2}$ |
| Preferred range | 14.5+ | 0-10 | 0-14 |
| More preferred range | 16+ | 0-9 | 0-12 |
| Most preferred range | 17+ | 0-8 | 0-10 |

The three dimensional solubility parameters listed above include: dispersive ($\delta_d$), polar ($\delta_p$) and hydrogen bonding ($\delta_h$) components (C. M. Hansen, Ind. Eng. and Chem., Prod. Res. and Devl., 9, No 3, p 282., 1970). These parameters may be determined empirically or calculated from known molar group contributions as described in Handbook of Solubility Parameters and Other Cohesion Parameters ed. A. F. M. Barton, CRC Press, 1991. The solubility parameters of many known polymers are also listed in this publication.

It is desirable that the permittivity of the binder has little dependence on frequency. This is typical of non-polar materials. Polymers and/or copolymers can be chosen as the binder by the permittivity of their substituent groups. A list of suitable and preferred low polarity binders is given (without limiting to these examples) in Table 2:

TABLE 2

| Binder | typical low frequency permittivity (∈) |
|---|---|
| Polystyrene | 2.5 |
| poly(α-methylstyrene) | 2.6 |
| poly(α-vinylnaphtalene) | 2.6 |
| poly(vinyltoluene) | 2.6 |
| Polyethylene | 2.2-2.3 |
| cis-polybutadiene | 2.0 |
| Polypropylene | 2.2 |
| Polyisoprene | 2.3 |
| poly(4-methyl-1-pentene) | 2.1 |
| poly (4-methylstyrene) | 2.7 |
| poly(chorotrifluoroethylene) | 2.3-2.8 |
| poly(2-methyl-1,3-butadiene) | 2.4 |
| poly(p-xylylene) | 2.6 |
| poly(α-α-α'-α' tetrafluoro-p-xylylene) | 2.4 |
| poly[1,1-(2-methyl propane)bis(4-phenyl)carbonate] | 2.3 |
| poly(cyclohexyl methacrylate) | 2.5 |
| poly(chlorostyrene) | 2.6 |
| poly(2,6-dimethyl-1,4-phenylene ether) | 2.6 |
| Polyisobutylene | 2.2 |
| poly(vinyl cyclohexane) | 2.2 |
| poly(vinylcinnamate) | 2.9 |
| poly(4-vinylbiphenyl) | 2.7 |

Other polymers suitable as binders include poly(1,3-butadiene) or polyphenylene.

Especially preferred are formulations wherein the binder is selected from poly-α-methyl styrene, polystyrene and polytriarylamine or any copolymers of these, and the solvent is selected from xylene(s), toluene, tetralin and cyclohexanone.

Copolymers containing the repeat units of the above polymers are also suitable as binders. Copolymers offer the possibility of improving compatibility with the polyacene of formula I, modifying the morphology and/or the glass transition temperature of the final layer composition. It will be appreciated that in the above table certain materials are insoluble in commonly used solvents for preparing the layer. In these cases analogues can be used as copolymers. Some examples of copolymers are given in Table 3 (without limiting to these examples). Both random or block copolymers can be used. It is also possible to add some more polar monomer components as long as the overall composition remains low in polarity.

TABLE 3

| Binder | typical low frequency permittivity ($\epsilon$) |
|---|---|
| Poly(ethylene/tetrafluoroethylene) | 2.6 |
| poly(ethylene/chlorotrifluoroethylene) | 2.3 |
| fluorinated ethylene/propylene copolymer | 2-2.5 |
| polystyrene-co-α-methylstyrene | 2.5-2.6 |
| ethylene/ethyl acrylate copolymer | 2.8 |
| poly(styrene/10% butadiene) | 2.6 |
| poly(styrene/15% butadiene) | 2.6 |
| poly(styrene/2,4 dimethylstyrene) | 2.5 |
| Topas ™ (all grades) | 2.2-2.3 |

Other copolymers may include: branched or non-branched polystyrene-block-polybutadiene, polystyrene-block(polyethylene-ran-butylene)-block-polystyrene, polystyrene-block-polybutadiene-block-polystyrene, polystyrene-(ethylene-propylene)-diblock-copolymers (e.g. KRATON®-G1701E, Shell), poly(propylene-co-ethylene) and poly(styrene-co-methylmethacrylate).

Preferred insulating binders for use in the organic semiconductor layer formulation according to the present invention are poly(α-methylstyrene), polyvinylcinnamate, poly(4-vinylbiphenyl), poly(4-methylstyrene), and Topas™ 8007 (linear olefin, cyclo-olefin(norbornene) copolymer available from Ticona, Germany). Most preferred insulating binders are poly(α-methylstyrene), polyvinylcinnamate and poly(4-vinylbiphenyl).

The binder can also be selected from crosslinkable binders, like e.g. acrylates, epoxies, vinylethers, thiolenes etc., preferably having a sufficiently low permittivity, very preferably of 3.3 or less. The binder can also be mesogenic or liquid crystalline.

As mentioned above the organic binder may itself be a semiconductor, in which case it will be referred to herein as a semiconducting binder. The semiconducting binder is still preferably a binder of low permittivity as herein defined. Semiconducting binders for use in the present invention preferably have a number average molecular weight ($M_n$) of at least 1500-2000, more preferably at least 3000, even more preferably at least 4000 and most preferably at least 5000. The semiconducting binder preferably has a charge carrier mobility, μ, of at least $10^{-5}$ $cm^2V^{-1}s^{-1}$, more preferably at least $10^4$ $cm^2V^{-1}s^{-1}$.

A preferred class of semiconducting binder is a polymer as disclosed in U.S. Pat. No. 6,630,566, preferably an oligomer or polymer having repeat units of formula 1:

$$+[Ar^1-\underset{|}{\overset{Ar^3}{N}}-Ar^2]_m+ \qquad 1$$

wherein
$Ar^1$, $Ar^2$ and $Ar^3$ which may be the same or different, denote, independently if in different repeat units, an optionally substituted aromatic group that is mononuclear or polynuclear, and
m is an integer $\geq 1$, preferably $\geq 6$, preferably $\geq 10$, more preferably $\geq 15$ and most preferably $\geq 20$.

In the context of $Ar^1$, $Ar^2$ and $Ar^3$, a mononuclear aromatic group has only one aromatic ring, for example phenyl or phenylene. A polynuclear aromatic group has two or more aromatic rings which may be fused (for example napthyl or naphthylene), individually covalently linked (for example biphenyl) and/or a combination of both fused and individually linked aromatic rings. Preferably each $Ar^1$, $Ar^2$ and $Ar^3$ is an aromatic group which is substantially conjugated over substantially the whole group.

Further preferred classes of semiconducting binders are those containing substantially conjugated repeat units. The semiconducting binder polymer may be a homopolymer or copolymer (including a block-copolymer) of the general formula 2:

$$A_{(c)}B_{(d)} \ldots Z_{(z)} \qquad 2$$

wherein A, B, ..., Z each represent a monomer unit and (c), (d), ... (z) each represent the mole fraction of the respective monomer unit in the polymer, that is each (c), (d), ... (z) is a value from 0 to 1 and the total of (c)+(d)+ ... +(z)=1.

Examples of suitable and preferred monomer units A, B, ... Z include units of formula 1 above and of formulae 3 to 8 given below (wherein m is as defined in formula 1:

wherein
$R^a$ and $R^b$ are independently of each other selected from H, F, CN, $NO_2$, —N($R^c$)($R^d$) or optionally substituted alkyl, alkoxy, thioalkyl, acyl, aryl,
$R^c$ and $R^d$ are independently or each other selected from H, optionally substituted alkyl, aryl, alkoxy or polyalkoxy or other substituents,
and wherein the asterisk (*) is any terminal or end capping group including H, and the alkyl and aryl groups are optionally fluorinated;

wherein
Y is Se, Te, O, S or —N($R^e$), preferably O, S or —N($R^e$)—,
$R^e$ is H, optionally substituted alkyl or aryl,
$R^a$ and $R^b$ are as defined in formula 3;

wherein $R^a$, $R^b$ and Y are as defined in formulae 3 and 4;

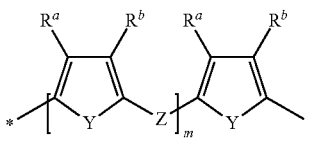

6 wherein $R^a$, $R^b$ and Y are as defined in formulae 3 and 4,
Z is —C($T^1$)=C($T^2$)-, —C≡C—, —N($R^f$)—, —N=N—, ($R^f$)=N—, —N=C($R^f$)—,
$T^1$ and $T^2$ independently of each other denote H, Cl, F, —CN or lower alkyl with 1 to 8 C atoms,
$R^f$ is H or optionally substituted alkyl or aryl;

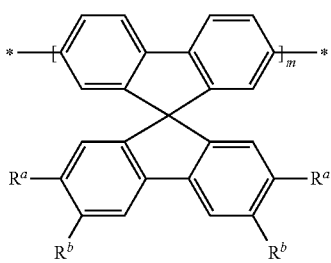

7 wherein $R^a$ and $R^b$ are as defined in formula 3;

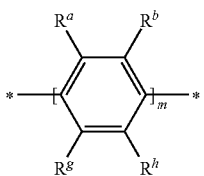

8 wherein $R^a$, $R^b$, $R^g$ and $R^h$ independently of each other have one of the meanings of $R^a$ and $R^b$ in formula 3.

In the case of the polymeric formulae described herein, such as formulae 1 to 8, the polymers may be terminated by any terminal group, that is any end-capping or leaving group, including H.

In the case of a block-copolymer, each monomer A, B, . . . Z may be a conjugated oligomer or polymer comprising a number, for example 2 to 50, of the units of formulae 3-8. The semiconducting binder preferably includes: arylamine, fluorene, thiophene, spiro bifluorene and/or optionally substituted aryl (for example phenylene) groups, more preferably arylamine, most preferably triarylamine groups. The aforementioned groups may be linked by further conjugating groups, for example vinylene.

In addition, it is preferred that the semiconducting binder comprises a polymer (either a homo-polymer or copolymer, including block-copolymer) containing one or more of the aforementioned arylamine, fluorene, thiophene and/or optionally substituted aryl groups. A preferred semiconducting binder comprises a homo-polymer or copolymer (including block-copolymer) containing arylamine (preferably triarylamine) and/or fluorene units. Another preferred semiconducting binder comprises a homo-polymer or copolymer (including block-copolymer) containing fluorene and/or thiophene units.

The semiconducting binder may also contain carbazole or stilbene repeat units. For example polyvinylcarbazole or polystilbene polymers or copolymers may be used. The semiconducting binder may optionally contain polyacene segments (for example repeat units as described for formula I above) to improve compatibility with the soluble polyacene molecules.

The most preferred semiconducting binders for use in the organic semiconductor layer formulation according to the present invention are poly(9-vinylcarbazole) and PTAA1, a polytriarylamine of the following formula

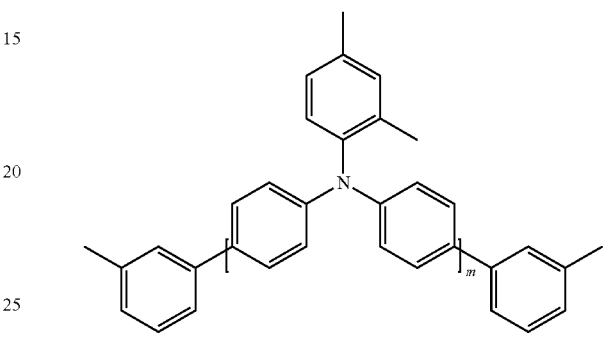

wherein m is as defined in formula 1.

For application of the semiconducting layer in p-channel FETs, it is desirable that the semiconducting binder should have a higher ionisation potential than the semiconducting compound of formula I, otherwise the binder may form hole traps. In n-channel materials the semiconducting binder should have lower electron affinity than the n-type semiconductor to avoid electron trapping.

The formulation according to the present invention may be prepared by a process which comprises:
(i) first mixing a compound of formula I and an organic binder or a precursor thereof. Preferably the mixing comprises mixing the two components together in a solvent or solvent mixture,
(ii) applying the solvent(s) containing the compound of formula I and the organic binder to a substrate; and optionally evaporating the solvent(s) to form a solid organic semiconducting layer according to the present invention,
(iii) and optionally removing the solid layer from the substrate or the substrate from the solid layer.

In step (i) the solvent may be a single solvent or the compound of formula I and the organic binder may each be dissolved in a separate solvent followed by mixing the two resultant solutions to mix the compounds.

The binder may be formed in situ by mixing or dissolving a compound of formula I in a precursor of a binder, for example a liquid monomer, oligomer or crosslinkable polymer, optionally in the presence of a solvent, and depositing the mixture or solution, for example by dipping, spraying, painting or printing it, on a substrate to form a liquid layer and then curing the liquid monomer, oligomer or crosslinkable polymer, for example by exposure to radiation, heat or electron beams, to produce a solid layer. If a preformed binder is used it may be dissolved together with the compound of formula I in a suitable solvent, and the solution deposited for example by dipping, spraying, painting or printing it on a substrate to form a liquid layer and then removing the solvent to leave a solid layer. It will be appreciated that solvents are chosen which are able to dissolve both the binder and the compound of formula I, and which upon evaporation from the solution blend give a coherent defect free layer.

Suitable solvents for the binder or the compound of formula I can be determined by preparing a contour diagram for the material as described in ASTM Method D 3132 at the concentration at which the mixture will be employed. The material is added to a wide variety of solvents as described in the ASTM method.

It will also be appreciated that in accordance with the present invention the formulation may also comprise two or more compounds of formula I and/or two or more binders or binder precursors, and that the process for preparing the formulation may be applied to such formulations.

Examples of suitable and preferred organic solvents include, without limitation, dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetralin, decalin, indane and/or mixtures thereof.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., Journal of Paint Technology, 38, No 496, 296 (1966)". Solvent blends may also be used and can be identified as described in "Solvents, W. H. Ellis, Federation of Societies for Coatings Technology, p 9-10, 1986". Such a procedure may lead to a blend of 'non' solvents that will dissolve both the binder and the compound of formula I, although it is desirable to have at least one true solvent in a blend.

Especially preferred solvents for use in the formulation according to the present invention, with insulating or semiconducting binders and mixtures thereof, are xylene(s), toluene, tetralin and o-dichlorobenzene.

The proportions of binder to the compound of formula I in the formulation or layer according to the present invention are typically 20:1 to 1:20 by weight, preferably 10:1 to 1:10 more preferably 5:1 to 1:5, still more preferably 3:1 to 1:3 further preferably 2:1 to 1:2 and especially 1:1. Surprisingly and beneficially, dilution of the compound of formula I in the binder has been found to have little or no detrimental effect on the charge mobility, in contrast to what would have been expected from the prior art.

In accordance with the present invention it has further been found that the level of the solids content in the organic semiconducting layer formulation is also a factor in achieving improved mobility values for electronic devices such as OFETs. The solids content of the formulation is commonly expressed as follows:

$$\text{Solids content }(\%) = \frac{a+b}{a+b+c} \times 100$$

wherein
a=mass of compound of formula I, b=mass of binder and c=mass of solvent.

The solids content of the formulation is preferably 0.1 to 10% by weight, more preferably 0.5 to 5% by weight.

Surprisingly and beneficially, dilution of the compound of formula I in the binder has been found to have little or no effect on the charge mobility, in contrast to what would have been expected from the prior art.

It is desirable to generate small structures in modern microelectronics to reduce cost (more devices/unit area), and power consumption. Patterning of the layer of the invention may be carried out by photolithography or electron beam lithography.

Liquid coating of organic electronic devices such as field effect transistors is more desirable than vacuum deposition techniques. The formulations of the present invention enable the use of a number of liquid coating techniques. The organic semiconductor layer may be incorporated into the final device structure by, for example and without limitation, dip coating, spin coating, ink jet printing, letter-press printing, screen printing, doctor blade coating, roller printing, reverse-roller printing, offset lithography printing, flexographic printing, web printing, spray coating, brush coating or pad printing. The present invention is particularly suitable for use in spin coating the organic semiconductor layer into the final device structure.

Selected formulations of the present invention may be applied to prefabricated device substrates by ink jet printing or microdispensing.

Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the mixture of the compound of formula I and the binder should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a formulation according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the binder and the compound of formula I which reduces or prevents clogging of the jets and separation of the components during spraying. The solvent(s) may include those selected from the following list of examples: dodecylbenzene, 1-methyl-4-tert-butylbenzene, terpineol limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The use of the binder in the present invention also allows the viscosity of the coating solution to be tuned to meet the requirements of the particular print head.

The semiconducting layer of the present invention is typically at most 1 micron (=1 µm) thick, although it may be thicker if required. The exact thickness of the layer will depend, for example, upon the requirements of the electronic device in which the layer is used. For use in an OFET or OLED, the layer thickness may typically be 500 nm or less.

In the semiconducting layer of the present invention there may be used two or more different compounds of formula I. Additionally or alternatively, in the semiconducting layer there may be used two or more organic binders of the present invention.

As mentioned above, the invention further provides a process for preparing the organic semiconducting layer which comprises (i) depositing on a substrate a liquid layer of a formulation which comprises one or more compounds of formula I, one or more organic binders or precursors thereof and optionally one or more solvents, and (ii) forming from the liquid layer a solid layer which is the organic semiconducting layer.

In the process, the solid layer may be formed by evaporation of the solvent and/or by reacting the binder resin precursor (if present) to form the binder resin in situ. The substrate may include any underlying device layer, electrode or separate substrate such as silicon wafer or polymer substrate for example.

In a particular embodiment of the present invention, the binder may be alignable, for example capable of forming a liquid crystalline phase. In that case the binder may assist alignment of the compound of formula I, for example such that the polyacene backbone is preferentially aligned along the direction of charge transport. Suitable processes for aligning the binder include those processes used to align polymeric organic semiconductors and are described in prior art, for example in WO 03/007397 (Plastic Logic).

The formulation according to the present invention can additionally comprise one or more further additives or components like for example plasticizers, antistatic agents, conductive dopants, reinforcing materials, surface-active compounds, lubricating agents, wetting agents, dispersing agents, hydrophobing agents, adhesive agents, flow improvers, defoaming agents, deaerators, diluents, reactive or non-reactive diluents, auxiliaries, colourants, dyes or pigments, furthermore, especially in case crosslinkable binders are used, catalysts, sensitizers, stabilizers, inhibitors, chain-transfer agents or co-reacting monomers.

Suitable reinforcing materials are for example fibers, such as glass fibers, carbon fibers, aramid fibers, boron fibers, carbon nanotubes etc.

The present invention also provides the use of the semiconducting compound, formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising the formulation according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The compound or formulation may be used, for example as a layer or film, in a field effect transistor (FET) for example as the semiconducting channel, organic light emitting diode (OLED) for example as a hole or electron injection or transport layer or electroluminescent layer, photodetector, chemical detector, photovoltaic cell (PVs), capacitor sensor, logic circuit, display, memory device and the like. The compound or formulation may also be used in electrophotographic (EP) apparatus. The compound or formulation is preferably solution coated to form a layer or film in the aforementioned devices or apparatus to provide advantages in cost and versatility of manufacture. The improved charge carrier mobility of the compound or formulation of the present invention enables such devices or apparatus to operate faster and/or more efficiently. The compound, formulation and layer of the present invention are especially suitable for use in an organic field effect transistor OFET as the semiconducting channel. Accordingly, the invention also provides an organic field effect transistor (OFET) comprising a gate electrode, an insulating (or gate insulator) layer, a source electrode, a drain electrode and an organic semiconducting channel connecting the source and drain electrodes, wherein the organic semiconducting channel comprises an organic semiconducting layer according to the present invention. Other features of the OFET are well known to those skilled in the art.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
a source electrode,
a drain electrode,
a gate electrode,
a semiconducting layer,
one or more gate insulator layers,
optionally a substrate.
wherein the semiconductor layer preferably comprises a polyacene compound, preferably a compound of formula I, very preferably a formulation comprising a polyacene compound of formula I and an organic binder as described above and below.

The OFET device can be a top gate device or a bottom gate device. Suitable structures and manufacturing methods of an OFET device are known to the skilled in the art and are described in the literature, for example in WO 03/052841.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377).

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

FET Measurements

Unless stated otherwise, the field effect mobility of the organic semiconductor materials according to the present invention is tested using the techniques described by Holland et al, J. Appl. Phys. Vol. 75, p. 7954 (1994).

A test field effect transistor is manufactured by using a PEN substrate upon which are patterned Pt/Pd source and drain electrodes by standard techniques, for example shadow masking. Semiconductor formulations are prepared using the organic semiconductor compound (here compound (1) of example 1 and compound (2) of example 2, respectively) blended with an inert polymeric binder resin (here poly(alpha-methylstyrene), Aldrich catalogue number 19, 184-1). The semiconductor formulations are then dissolved one part into 99 parts of solvent (here p-Xylene), and spin coated onto the substrate at 500 rpm for 18 seconds. To ensure complete drying, the samples are placed in an oven for 20 minutes at 100° C.

The insulator material (Cytop 809M®, available from Asahi Glass) is spin-coated onto the semiconductor giving a thickness typically of approximately 1 μm. The samples are placed once more in an oven at 100° C. for 20 minutes to evaporate solvent from the insulator. A gold gate contact is defined over the device channel area by evaporation through a shadow mask. To determine the capacitance of the insulator layer a number of devices are prepared which consist of a non-patterned Pt/Pd base layer, an insulator layer prepared in the same way as that on the FET device, and a top electrode of known geometry. The capacitance is measured using a hand-held multimeter, connected to the metal either side of the insulator. Other defining parameters of the transistor are the length of the drain and source electrodes facing each other (W=30 mm) and their distance from each other (L=130 μm).

The voltages applied to the transistor are relative to the potential of the source electrode. In the case of a p-type gate material, when a negative potential is applied to the gate, positive charge carriers (holes) are accumulated in the semiconductor on the other side of the gate dielectric. (For an n-channel FET, positive voltages are applied). This is called the accumulation mode. The capacitance per unit area of the gate dielectric $C_i$ determines the amount of the charge thus induced. When a negative potential $V_{DS}$ is applied to the drain, the accumulated carriers yield a source-drain current $I_{DS}$ which depends primarily on the density of accumulated carriers and, importantly, their mobility in the source-drain channel. Geometric factors such as the drain and source electrode configuration, size and distance also affect the current. Typically a range of gate and drain voltages are scanned during the study of the device. The source-drain current is described by Equation (1).

$$I_{DS} = \frac{\mu W C_i}{L}\left((V_G - V_0)V_{DS} - \frac{V_{DS}^2}{2}\right) + I_\Omega \qquad (1)$$

where $V_0$ is an offset voltage and $I_\Omega$ is an ohmic current independent of the gate voltage and is due to the finite conductivity of the material. The other parameters are as defined above.

For the electrical measurements the transistor sample is mounted in a sample holder. Microprobe connections are made to the gate, drain and source electrodes using Karl Suss PH100 miniature probe-heads. These are linked to a Hewlett-Packard 4155B parameter analyser. The drain voltage is set to −5 V and the gate voltage is scanned from +20 to −60V and back to +20V in 1 V steps. In accumulation, when $|V_G|>|V_{DS}|$ the source-drain current varies linearly with $V_G$. Thus the field effect mobility can be calculated from the gradient (S) of $I_{DS}$ vs. $V_G$ given by Equation (2).

$$S = \frac{\mu W C_i V_{DS}}{L} \qquad (2)$$

All field effect mobilities quoted below are calculated using this regime (unless stated otherwise). Where the field effect mobility varies with gate voltage, the value is taken as the highest level reached in the regime where $|V_G|>|V_{DS}|$ in accumulation mode. The values quoted below are an average taken over several devices (fabricated on the same substrate).

The invention will now be described in more detail by reference to the following examples, which are illustrative only and do not limit the scope of the invention.

The following parameters are used:

μ is the charge carrier mobility

W is the length of the drain and source electrode

L is the distance of the drain and source electrode $I_{DS}$ is the source-drain current $C_i$ is the capacitance per unit area of the gate dielectric $V_G$ is the gate voltage (in V)

$V_{DS}$ is the source-drain voltage $V_0$ is the offset voltage

Unless stated otherwise, all specific values of physical parameters like the permittivity (∈), charge carrier mobility (μ), solubility parameter (δ) and viscosity (η) as given above and below refer to a temperature of 20° C. (+/−1° C.).

Example 1

Compound (1) is prepared as described in Schemes 1-4 above.

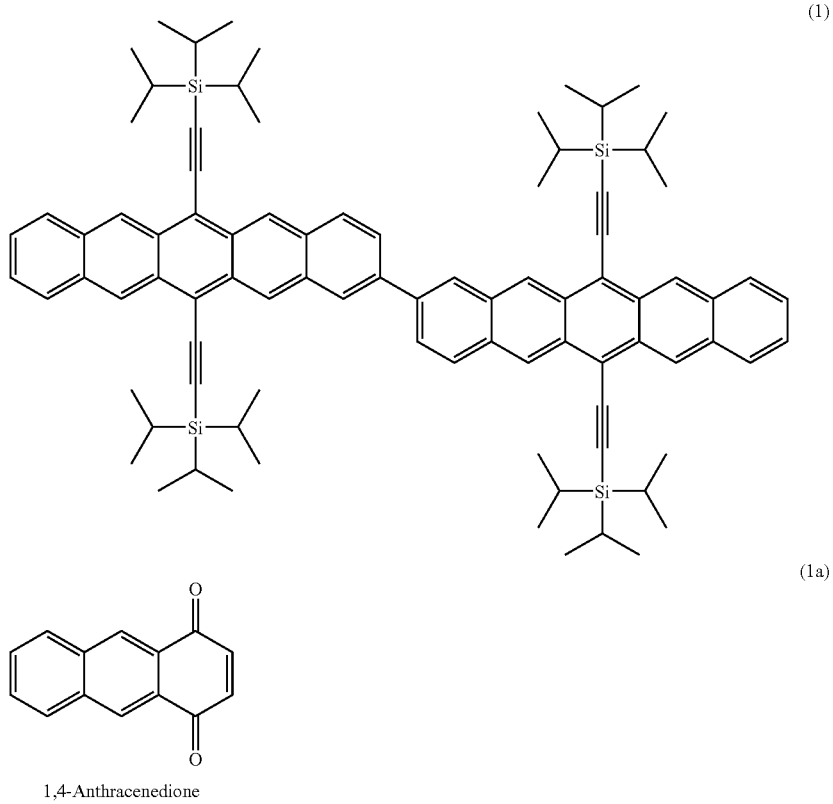

(1)

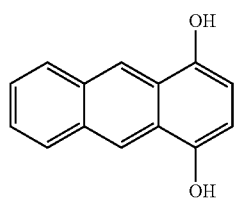

1,4-Anthracenedione (1a)

To a solution of quinizarin (10.00 g, 42.0 mmol, 1 molar equivalent) in methanol (200 mL) cooled to −0° C. is added sodium borohydride (6.38 g, 169.0 mmol, 4 molar equivalents). The resulting mixture is stirred at −0° C. for 2 h. A solution of 5M hydrochloric acid (150 mL) is then added dropwise to the reaction mixture at 0° C. The precipitated orange solid is filtered, washed twice with water, and dried under vacuum. Purification by column chromatography on alumina (eluent: dichloromethane) gave the title compound as yellow needles (5.9 g, 68%). $^1$H NMR (300.13 MHz, CDCl$_3$) δ(ppm) 7.08 (s, 2H) 7.68-7.72 (m, 2H) 8.05-8.10 (m, 2H) 8.63 (s, 2H).

1,4-dihydroxyanthracene (1b)

A solution of sodium hydrosulfite (16.70 g, 42.0 mmol, 1 molar equivalent) in a water/dioxane (3/2) (250 mL) mixture is added under nitrogen to the 1,4-anthracenedione 1a (5.00 g, 24.0 mmol, 1 molar equivalent). The resulting mixture is stirred at room temperature for 3 h. Water is added and the resulting precipitate is filtered, washed with water and dried under vacuum to give the title compound as a yellow powder (3.10 g, 61%). $^1$H NMR (300.13 MHz, THF-d$_8$) δ(ppm) 6.53 (s, 2H) 7.34-7.40 (m, 2H) 7.96-7.99 (m, 2H) 8.65 (s, 2H) 8.70 (s, 2H).

3,3',4,4'-tetra(hydroxymethyl)-1,1'-biphenyl (1c)

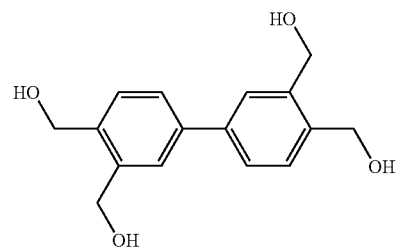

To a solution of 3,3',4,4'-biphenyltetracarboxylic dianhydride (6.0 g, 20.4 mmol, 1.0 molar equivalent) in THF (600 mL) heated to 100° C. is added carefully a solution of LiAlH$_4$ (1M in tetrahydrofuran) (81 mL, 81.6 mmol, 2.0 molar equivalents). The reaction mixture is stirred overnight at 100° C. To this resulting solution cooled at 0° C. is added a 2M sodium hydroxide solution (50 mL) followed by cold water (25 mL) and THF (50 mL). The reaction mixture is then filtered and concentrated under vacuum. The crude product is then washed with THF (20 mL), water (10 mL) and dried over vacuum to give a white powder (3.1 g, 55%). If necessary, the compound can be further purified by recrystallisation in water to give the expected compound as a white powder (3.3 g, 79%). $^1$H NMR (300.13 MHz, DMSO) δ (ppm) 4.57 (d, J=4.5

Hz, 4H) 4.61 (d, J=4.5 Hz, 4H) 5.09 (t, J=5.2 Hz, 2H) 5.15 (t, J=5.2 Hz, 2H) 7.46 (d, J=8.1 Hz, 2H) 7.52 (dd, J$_1$=8.1, J$_2$=1.8 Hz, 2H) 7.70 (d, J=1.8 Hz, 2H).

1,1'-biphenyl-3,3',4,4'-tetracarboxaldehyde (1d)

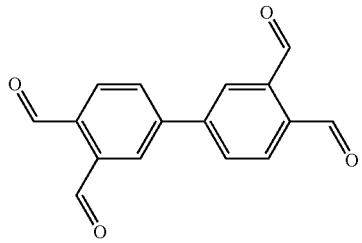

To a solution of oxalyl chloride 2M in dichloromethane (DCM) (2.8 mL, 5.6 mmol, 4.4 molar equivalents) cooled to −78° C. is added dropwise a solution of dimethylsulfoxyde (DMSO) (0.8 mL, 11.1 mmol, 8.8 molar equivalents) in DCM (10 ml). The solution is stirred at −78° C. for 5 min and 3,3',4,4'-tetra(hydroxymethyl)-1,1'-biphenyl 1c (0.22 g, 1.3 mmol, 1.0 molar equivalent) dissolved in a mixture of DCM-DMSO (1 ml-2 ml) is added dropwise. The solution is stirred for 1 h at −78° C. and triethylamine (6 mL) is slowly added at −78° C. The reaction mixture is stirred 10 minutes at −78° C. and slowly warmed up to room temperature. Ice-cold water (30 ml) is added to the reaction mixture and the aqueous layer extracted with DCM (3×30 ml). The organic fractions are combined, dried over magnesium sulfate, filtered and concentrated in vacuum to give a brown oil. Purification by column chromatography on silica gel (eluent: hexane-ethyl acetate 6/4) gave the title compound as an off-white powder (90 mg, 42%). $^1$H NMR (300.13 MHz, CDCl$_3$) δ (ppm) 8.02 (dd, J$_1$=8.1, J$_2$=1.8 Hz, 2H) 8.14 (d, J=8.1 Hz, 2H) 8.28 (d, J=1.8 Hz, 2H) 10.58 (s, 2H) 10.68 (s, 2H).

2-(6,13-pentacenequinone)-6,13-pentacenequinone or 2,2'-bi-6,13-pentacenequinone (1e)

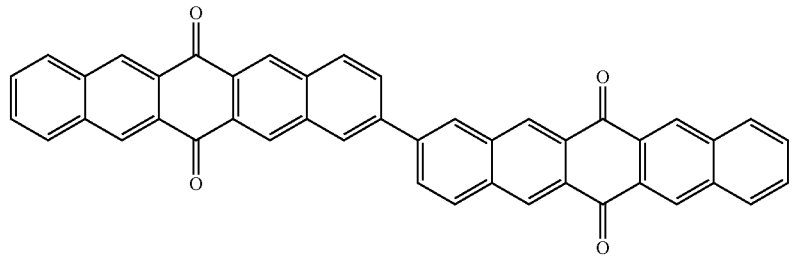

To a solution of 1,1'-biphenyl-3,3',4,4'-tetracarboxaldehyde 1d (50 mg, 0.38 mmol, 1 molar equivalent) and 1,4-dihydroxyanthracene 1b (79 mg, 1.9 mmol, 2 molar equivalents) warmed to 50° C. in ethanol (20 ml) is added a solution of 5% aqueous NaOH (1 ml). After 1 hour at 50° C., the reaction mixture is cooled to room temperature. The resulting precipitate is filtered, washed with water (15 ml), a mixture ethanol/water (20 ml) and ethanol (20 ml) to give the title compound as a yellow powder (90 mg, 78%) used as obtained.

2-(6,13-bis(triisopropylsilylethynyl)pentacenyl)-6,13-bis(triisopropylsilylethynyl)pentacene or 2,2'-bi-6,13-bis(triisopropylsilylethynyl)-pentacene (1)

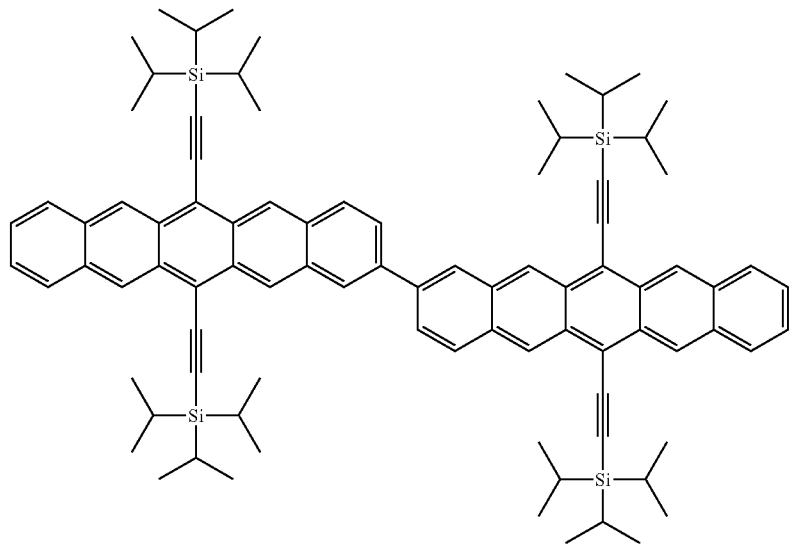

To a solution of triisopropylsilylacetylene (0.4 mL, 1.8 mmol, 12 molar equivalents) in tetrahydrofurane (THF) (10 ml) cooled to −78° C. is added dropwise a 2.5M solution of n-butyllithium in hexane (0.6 mL, 1.5 mmol, 10 molar equivalents). The solution is stirred at −78° C. for 45 min and 2-(6,13-pentacenequinone)-6,13-pentacenequinone or 2,2'-bi-6,13-pentacenequinone 1e (90 mg, 0.15 mmol, 1 molar equivalent) is added. The reaction mixture is warmed up and stirred overnight at room temperature. A solution of 10% aqueous HCl saturated with $SnCl_2$ (1 ml) is added at room temperature and the reaction mixture is stirred at 50° C. for 45 min. After cooling a solution of 2M aqueous solution of $Na_2CO_3$ (1 ml) is added to the reaction mixture and the resulting solution is stirred with celite for 5 min. The solution is filtered through celite and concentrated under vacuum to give a dark solid. Purification by column chromatography on silica gel (eluent: hexane-DCM 80/20) followed by an acetone wash gave the title compound as a grey blue powder (3 mg, 2%). $^1$H NMR (300.13 MHz, $CDCl_3$) δ (ppm) 1.32-1.43 (m, 42H) 7.41-7.44 (m 4H) 7.92-8.01 (m, 6H) 8.15 (d, J=9.0 Hz, 2H) 9.32-9.35 (m, 6H) 9.41 (s, 2H).

Example 2

Compound (2) is prepared as described below.

(2)

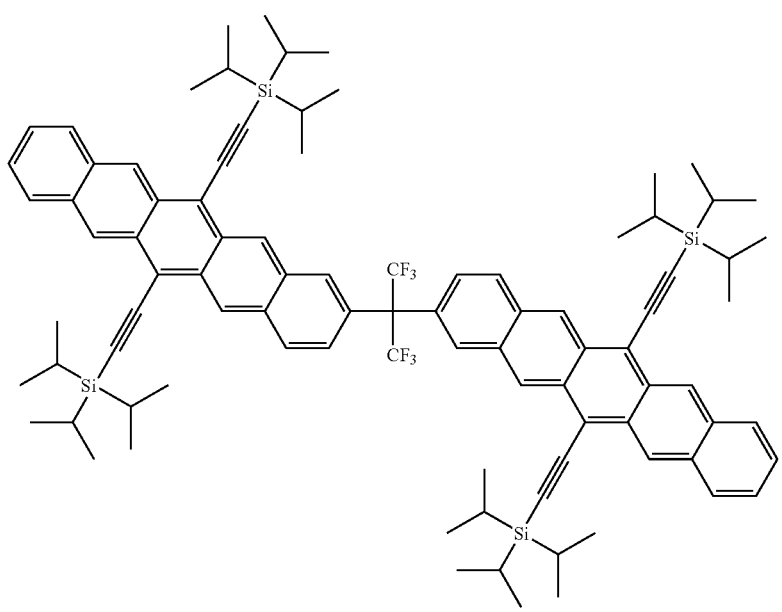

4,4'-4,4'-(Hexafluoroisopropylidene)bis(benzene-1,2-dimethanol)

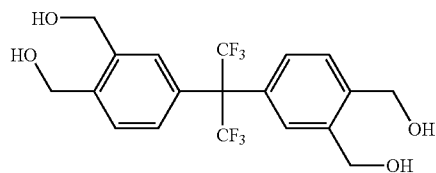

To a solution of $LiAlH_4$ (1M in THF) (22.5 mL, 23.0 mmol, 2.0 molar equivalents) in THF (60 mL) cooled to −78° C. is added dropwise a solution of 4,4'-(hexafluoroisopropylidene) diphthalic anhydride (5.0 g, 11.2 mmol, 1 molar equivalent) in THF (25 ml). The reaction mixture is allowed to warm up to room temperature and then stirred at 70° C. for 2 hrs. To this resulting solution cooled at 0° C. is added a 2M sodium hydroxide solution (20 mL) followed by cold water (25 mL) and THF (50 mL). The reaction mixture is then further extracted with THF (3×50 mL). The organic fractions are combined, washed with brine, dried as added over magnesium sulfate, filtered and concentrated in vacuum to give a white powder used as obtained (4.16 g, 87%). $^1$H NMR (300.13 MHz, DMSO-$d_6$) δ(ppm) 4.54 (d, J=5.40 Hz, 8H) 5.17-5.23 (m, 4H) 7.15 (d, J=8.10 Hz, 4H) 7.46-7.49 (m, 2H) $^{19}$F NMR (282.38 MHz, DMSO-$d_6$) δ(ppm)-62.34 (s).

4,4'-(Hexafluoroisopropylidene)diphthaldehyde

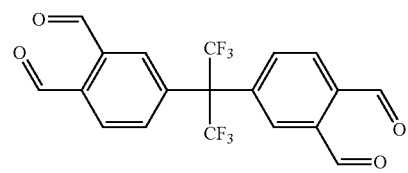

To a solution of oxalyl chloride (3.5 mL, 41 mmol, 4.4 molar equivalents) in DCM (50 mL) cooled to −78° C. is added dropwise a solution of dimethylsulfoxide (DMSO) (5.9 mL, 83 mmol, 8.8 molar equivalents) in DCM (10 ml). The solution is stirred at −78° C. for 10 min and 4,4'-(hexafluoroisopropylidene)bis(benzene-1,2-dimethanol) (4.00 g, 9.3 mmol, 1.0 molar equivalent) dissolved in a mixture of DCM-DMSO (1 ml-4 ml) is added dropwise. The solution is stirred for 30 min at −78° C. and triethylamine (30 mL) is slowly added at −78° C. The reaction mixture is stirred 10 minutes at −78° C. and slowly warmed up to room temperature. Ice-cold water (50 ml) is added to the reaction mixture and the aqueous layer extracted with DCM (3×50 ml). The organic fractions are combined, dried over magnesium sulfate, filtered and concentrated in vacuum to give a brown oil which crystallised spontaneously. Purification by hexane washes gave the title compound as a light brown solid (2.8 g, 71%). $^1$H NMR (300.13 MHz, CDCl$_3$) δ(ppm) 7.80 (d, J=8.0 Hz, 2H) 7.96 (s, 2H) 8.05 (d, J=8.0 Hz, 2H) 10.51 (s, 2H) 10.57 (s, 2H) $^{19}$F NMR (282.38 MHz, DMSO) δ(ppm)-62.34 (s).

4,4'-(Hexafluoroisopropylidene)bis(6,13-pentacene-quinone)

To a solution of triisopropylsilylacetylene (1.75 mL, 7.8 mmol, 12 molar equivalents) in anhydrous tetrahydrofurane (THF) (50 ml) cooled to −78° C. is added dropwise a 2.5M solution of n-butyllithium in hexanes (2.9 mL, 7.1 mmol, 11 molar equivalents). The solution is stirred at −78° C. for 45 min and 4,4'-(hexafluoroisopropylidene)bis(6,13-pentacene-quinone) (0.5 g, 0.65 mmol, 1 molar equivalent) is added. The reaction mixture is warmed up and stirred overnight at room

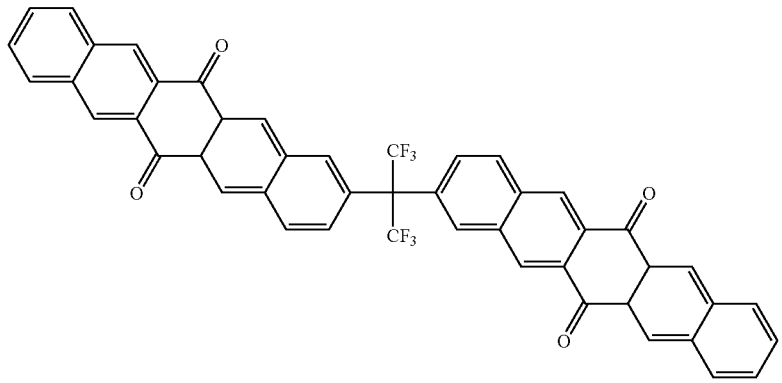

Anhydrous pyridine (80 mL) is added under nitrogen to 4,4'-(hexafluoroisopropylidene)diphthaldehyde (2.00 g, 4.8 mmol, 1 molar equivalent) and 1,4-dihydroxyanthracene (2.02 g, 96.0 mmol, 2 molar equivalents). The resulting solution is heated to 120° C. After 30 min, a yellow precipitate started to form and the reaction mixture is stirred for 16 h at 120° C. for completion. The yellow precipitate is filtered off, washed with methanol, a mixture methanol/water (1:1), acetone and dried in vacuum oven to give the title compound as a yellow powder (2.35 g, 64%).

4,4'-(Hexafluoroisopropylidene)bis(6,13-bis(triisopropylsilylethynyl)pentacene) (2)

temperature. A solution of 10% aqueous HCl saturated with SnCl$_2$ (10 ml) is added at room temperature and the reaction mixture is stirred at 50° C. for 45 min. After cooling a solution of 2M aqueous solution of Na$_2$CO$_3$ (10 ml) is added. The solution is filtered through celite and concentrated under vacuum to give a dark solid. Purification by column chromatography on silica gel (eluent: hexane-DCM 80/20) followed by a methanol wash gave the title compound as a blue powder (0.3 g, 32%). $^1$H NMR (300.13 MHz, CDCl$_3$) δ (ppm) 1.26-1.44 (m, 84H) 7.33 (d, J=9.30 Hz, 2H) 7.44-7.48 (m, 4H) 7.99-8.03 (m, 6H) 8.24 (s, 2H) 9.31 (s, 2H) 9.34 (s, 4H) 9.41 (s, 2H).

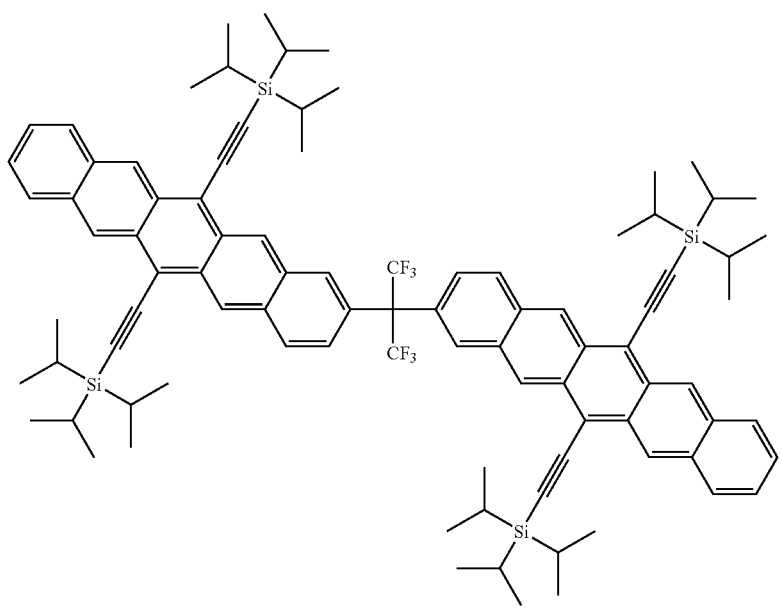

Example 3

Compound (3) is prepared as described below.

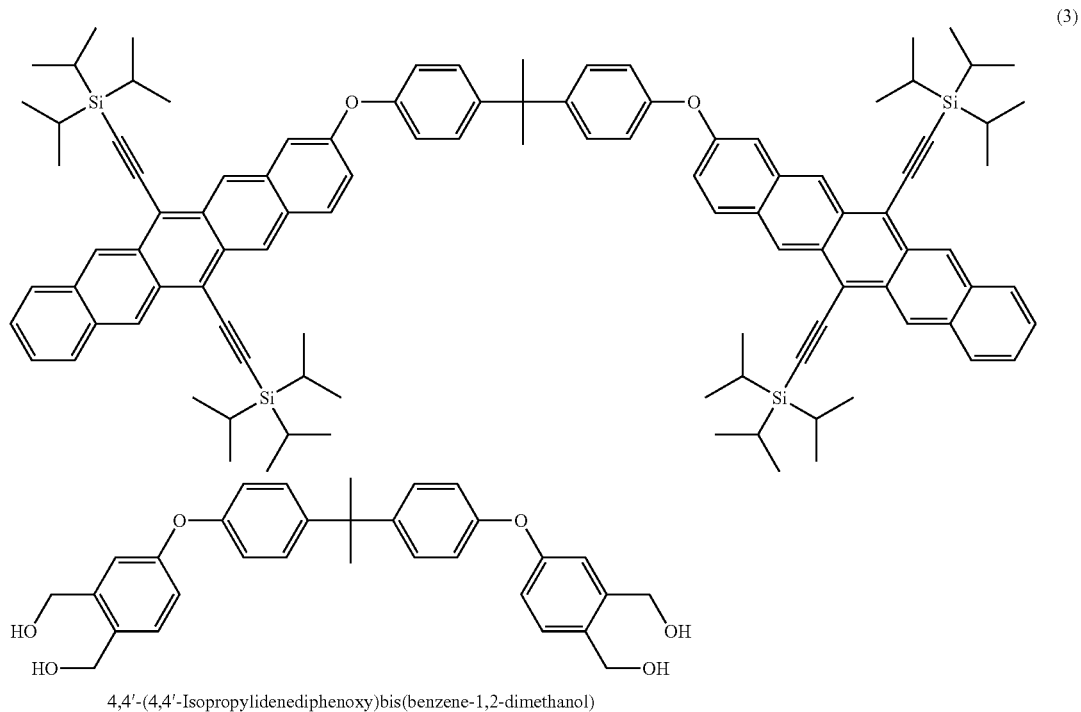

(3)

4,4'-(4,4'-Isopropylidenediphenoxy)bis(benzene-1,2-dimethanol)

To a solution of LiAlH₄ (1M in THF) (38 mL, 38.0 mmol, 4.0 molar equivalents) in THF (50 mL) cooled to −78° C. is added dropwise a solution of 4,4'-(4,4'-isopropylidenediphenoxy)bis(phthalic anhydride) (5.0 g, 9.6 mmol, 1 molar equivalent) in THF (25 ml). The reaction mixture is allowed to warm up to room temperature and then stirred at 70° C. for 2 hrs. To this resulting solution cooled at 0° C. is added a 2M sodium hydroxide solution (40 mL) followed by cold water (25 mL) and THF (50 mL). The reaction mixture is then further extracted with THF (3×50 mL). The organic fractions are combined, washed with brine, dried as added over magnesium sulfate, filtered and concentrated in vacuum to give a light brown oil. The crude oil is dissolved in acetone and Et₂O is added until an off-white precipitate started to form. After filtration, the organic layer is concentrated in vacuum to give a light brown oil which crystallises spontaneously. Purification by DCM washes gave the title compound as a white powder (3.48 g, 72%). ¹H NMR (300.13 MHz, DMSO-d₆) δ(ppm) 1.63 (s, 6H) 4.47 (d, J=5.40 Hz, 4H) 4.52 (d, J=5.40 Hz, 4H) 5.03 (t, J=5.40 Hz, 2H) 5.12 (t, J=5.40 Hz, 2H) 6.83-6.91 (m, 6H) 7.06 (d, J=2.40 Hz, 2H) 7.20-7.25 (m, 4H) 7.34 (d, J=8.40 Hz, 2H).

4,4'-(4,4'-Isopropylidenediphenoxy)bis(phthaldehyde)

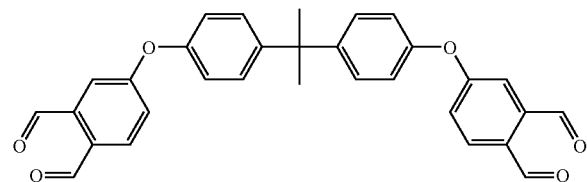

To a solution of oxalyl chloride (2.2 mL, 26 mmol, 4.4 molar equivalents) in DCM (50 mL) cooled to −78° C. is added dropwise a solution of dimethylsulfoxide (DMSO) (3.7 mL, 52 mmol, 8.8 molar equivalents) in DCM (10 ml). The solution is stirred at −78° C. for 10 min and 4,4'-(4,4'-isopropylidenediphenoxy)bis(benzene-1,2-dimethanol) (3.00 g, 6 mmol, 1.0 molar equivalent) dissolved in a mixture of DCM-DMSO (1 ml-4 ml) is added dropwise. The solution is stirred for 30 min at −78° C. and triethylamine (30 mL) is slowly added at −78° C. The reaction mixture is stirred 10 minutes at −78° C. and slowly warmed up to room temperature. Ice-cold water (50 ml) is added to the reaction mixture and the aqueous layer extracted with DCM (3×50 ml). The organic fractions are combined, dried over magnesium sulfate, filtered and concentrated in vacuum to give a brown oil which crystallised spontaneously. Purification by hexane washes gave the title compound as a light brown solid (2.10 g, 71%). ¹H NMR (300.13 MHz, CDCl₃) δ(ppm) 1.75 (s, 6H) 7.00-7.05 (m, 4H) 7.29-7.34 (m, 6H) 7.49 (d, J=2.70 Hz, 2H) 7.95 (d, J=8.70 Hz, 2H) 10.37 (s, 2H) 10.58 (s, 2H).

4,4'-(4,4'-Isopropylidenediphenoxy)bis(6,13-pentacenequinone)

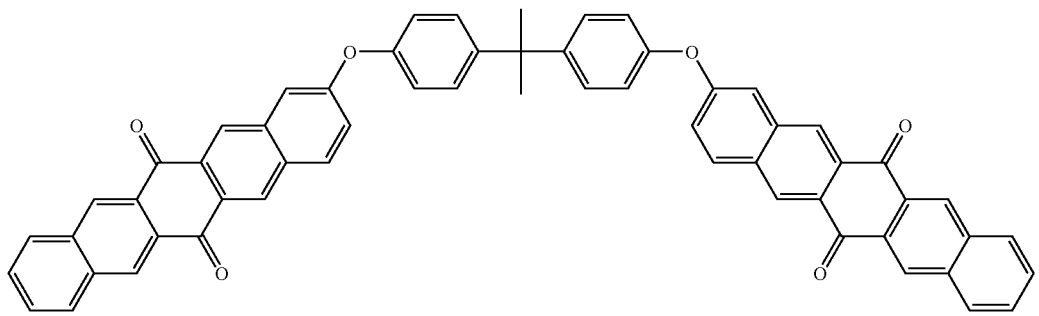

Anhydrous pyridine (25 mL) is added under nitrogen to 4,4'-(4,4'-isopropylidenediphenoxy)bis(phthaldehyde) (0.50 g, 1.0 mmol, 1 molar equivalent) and 1,4-dihydroxyanthracene (0.43 g, 2.0 mmol, 2 molar equivalents). The resulting solution is heated to 120° C. After 30 min, a yellow precipitate started to form and the reaction mixture is stirred for 16 h at 120° C. for completion. The yellow precipitate is filtered off, washed with methanol, a mixture methanol/water (1:1), acetone and dried in vacuum oven to give the title compound as a yellow powder (0.49 g, 57%).

4,4'-(4,4'-Isopropylidenediphenoxy)bis(6,13-bis(triisopropylsilylethynyl)pentacene) (3)

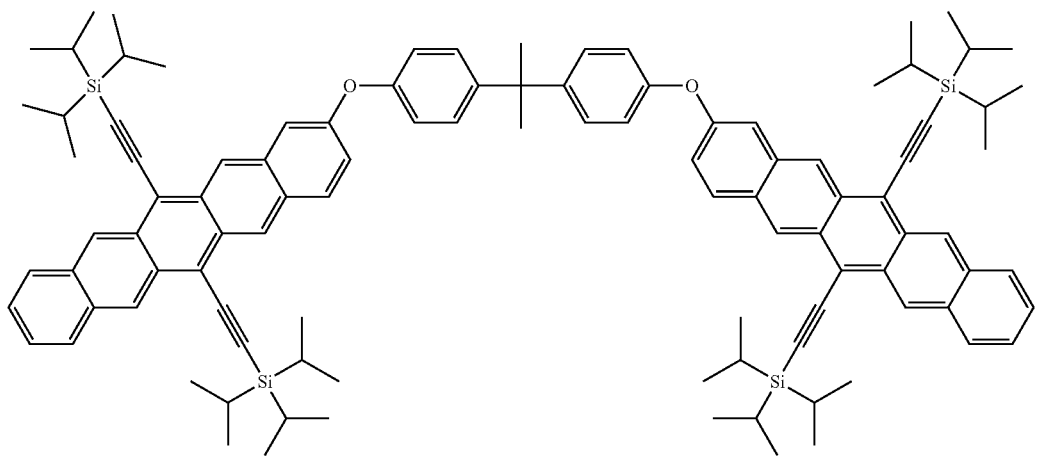

To a solution of triisopropylsilylacetylene (1.53 mL, 6.8 mmol, 12 molar equivalents) in anhydrous diethylether oxyde (Et$_2$O) (50 ml) cooled to −78° C. is added dropwise a 2.5M solution of n-butyllithium in hexanes (2.5 mL, 6.2 mmol, 11 molar equivalents). The solution is stirred at −78° C. for 45 min and 4,4'-(4,4'-isopropylidenediphenoxy)bis(6,13-pentacenequinone) (0.48 g, 0.6 mmol, 1 molar equivalent) is added. The reaction mixture is warmed up and stirred overnight at room temperature. A solution of 10% aqueous HCl saturated with SnCl$_2$ (5 ml) is added at room temperature and the reaction mixture is stirred at 50° C. for 45 min. After cooling a solution of 2M aqueous solution of Na$_2$CO$_3$ (5 ml) is added. The solution is filtered through celite and concentrated under vacuum to give a dark solid. Purification by column chromatography on silica gel (eluent: hexane-DCM 70/30) followed by an acetone wash gave the title compound as a blue powder (0.55 g, 64%). $^1$H NMR (300.13 MHz, CDCl$_3$) δ (ppm) 1.21-1.43 (m, 84H) 1.79 (s, 6H) 7.11-7.14 (m, 4H) 7.28-7.31 (m, 4H) 7.36-7.44 (m, 8H) 7.95-9.03 (m, 6H) 9.09 (s, 2H) 9.25 (s, 2H) 9.29 (s, 4H).

Example 4

Compound (4) is prepared as described below.

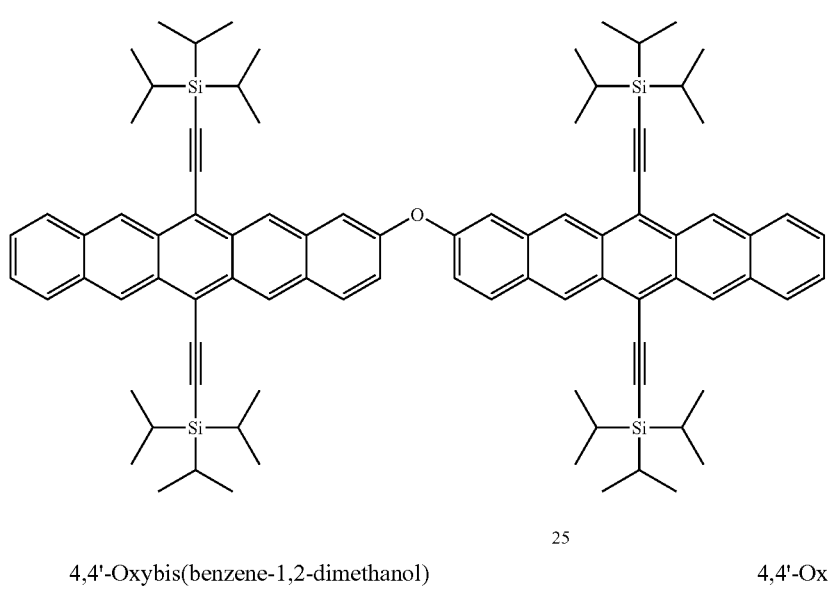

4,4'-Oxybis(benzene-1,2-dimethanol)

4,4'-Oxydiphthaldehyde

To a solution of LiAlH$_4$ (1M in THF) (64 mL, 64.0 mmol, 4.0 molar equivalents) in THF (50 mL) cooled to −78° C. is added dropwise a solution of 4,4'-oxydiphthalic anhydride (5.0 g, 9.6 mmol, 1 molar equivalent) in THF (20 ml). The reaction mixture is allowed to warm up to room temperature and then stirred at 70° C. for 2 hrs. To this resulting solution cooled at 0° C. is added a 2M sodium hydroxide solution (40 mL) followed by cold water (25 mL) and THF (50 mL). The reaction mixture is then further extracted with THF (3×50 mL). The organic fractions are combined, washed with brine, dried as added over magnesium sulfate, filtered and concentrated in vacuum to give a light brown oil. The crude oil is dissolved in acetone and Et$_2$O is added until an off-white precipitate started to form. After filtration, the organic layer is concentrated in vacuum to give a light brown oil which crystallises spontaneously. Purification by DCM washes gave the title compound as a light yellow powder (2.75 g, 59%). $^1$H NMR (300.13 MHz, DMSO-d$_6$) δ(ppm) 4.47 (d, J=5.40 Hz, 4H) 4.53 (d, J=5.40 Hz, 4H) 5.03 (t, J=5.40 Hz, 2H) 5.12 (t, J=5.40 Hz, 2H) 6.84 (dd, J$_1$=2.70 Hz, J$_2$=8.40 Hz, 2H) 7.04 (d, J=2.70 Hz, 2H) 7.34 (d, J=8.40 Hz, 2H).

To a solution of oxalyl chloride (3.4 mL, 40 mmol, 4.4 molar equivalents) in DCM (50 mL) cooled to −78° C. is added dropwise a solution of dimethylsulfoxide (DMSO) (5.8 mL, 81 mmol, 8.8 molar equivalents) in DCM (10 ml). The solution is stirred at −78° C. for 10 min and 4,4'-oxybis (benzene-1,2-dimethanol) (2.68 g, 9 mmol, 1.0 molar equivalent) dissolved in a mixture of DCM-DMSO (1 ml-4 ml) is added dropwise. The solution is stirred for 30 min at −78° C. and triethylamine (30 mL) is slowly added at −78° C. The reaction mixture is stirred 10 minutes at −78° C. and slowly warmed up to room temperature. Ice-cold water (50 ml) is added to the reaction mixture and the aqueous layer extracted with DCM (3×50 ml). The organic fractions are combined, dried over magnesium sulfate, filtered and concentrated in vacuum to give a vitreous compound used as obtained (1.75 g, 67%). $^1$H NMR (300.13 MHz, CDCl$_3$) δ(ppm) 7.43 (dd, J$_1$=2.40 Hz, J$_2$=8.40 Hz, 2H) 8.06 (d, J=2.40 Hz, 2H) 8.06 (d, J=8.40 Hz, 2H) 10.44 (s, 2H) 10.61 (s, 2H).

4,4'-Oxybis(6,13-pentacenequinone)

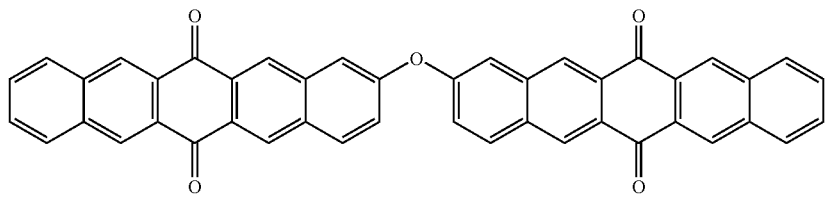

Anhydrous pyridine (75 mL) is added under nitrogen to 4,4'-oxydiphthaldehyde (1.75 g, 6.2 mmol, 1 molar equivalent) and 1,4-dihydroxyanthracene (2.60 g, 12.3 mmol, 2 molar equivalents). The resulting solution is heated to 120° C. After 30 min, a yellow precipitate started to form and the reaction mixture is stirred for 16 h at 120° C. for completion. The yellow precipitate is filtered off, washed with methanol, a mixture methanol/water (1:1), acetone and dried in vacuum oven to give the title compound as a yellow powder (1.49 g, 38%).

4,4'-Oxybis(6,13-bis(triisopropylsilylethynyl)pentacene) (4)

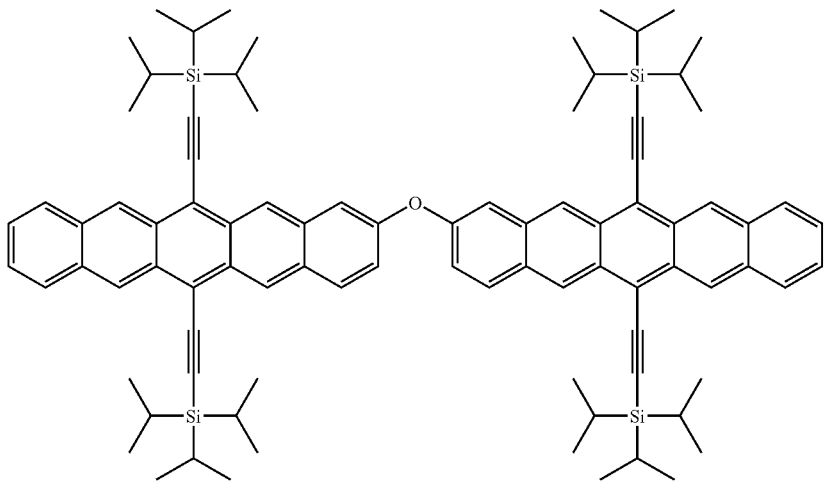

To a solution of triisopropylsilylacetylene (2.14 mL, 9.5 mmol, 12 molar equivalents) in anhydrous diethylether (Et$_2$O) (50 ml) cooled to −78° C. is added dropwise a 2.5M solution of n-butyllithium in hexanes (3.5 mL, 8.7 mmol, 11 molar equivalents). The solution is stirred at −78° C. for 45 min and 4,4'-oxybis(6,13-pentacenequinone) (0.5 g, 0.79 mmol, 1 molar equivalent) is added. The reaction mixture is warmed up and stirred overnight at room temperature. A solution of 10% aqueous HCl saturated with SnCl$_2$ (5 ml) is added at room temperature and the reaction mixture is stirred at 50° C. for 45 min. After cooling a solution of 2M aqueous solution of Na$_2$CO$_3$ (5 ml) is added to the reaction mixture. The solution is filtered through celite and concentrated under vacuum to give a dark solid. Purification by column chromatography on silica gel (eluent: hexane-DCM 70/30) followed by a methanol wash gave the title compound as a blue powder (0.52 g, 51%). $^1$H NMR (300.13 MHz, CDCl$_3$) δ (ppm) 1.24-1.43 (m, 84H) 7.38-7.47 (m, 6H) 7.55 (s, 2H) 7.98-8.02 (m, 4H) 8.10 (d, J=9.6 Hz, 2H) 9.20 (s, 2H) 9.30 (s, 2H) 9.33 (s, 2H) 9.37 (s, 2H).

Example 5

FET Measurements

The field effect mobility of organic semiconductor materials comprising compounds (1)-(4) is tested as described above. Examples of the current-voltage and mobility-voltage characteristics for example 1 to 4 are shown in FIGS. 1 to 4, respectively. The forward and reverse scans illustrate the low current hysteresis of the device.

FIG. 1: Compound 1 (TIPS dimer pure)+polyalphamethylstyrene binder (1:1) 1% solids in chlorobenzene. Average mobility=2.9×10$^{-2}$ cm$^2$Vs.

Figure 2:
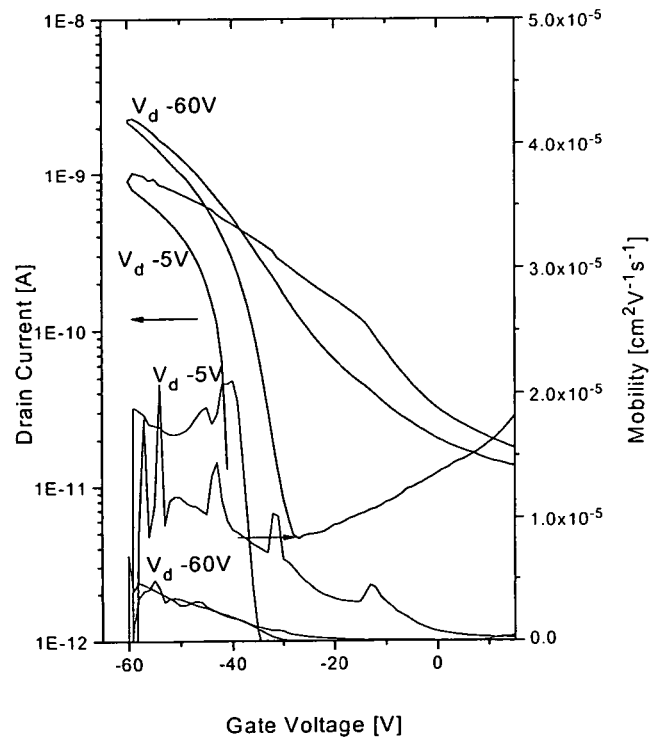

FIG. 2: Compound 2 (TIPS non conjugated pentacene dimer)+polyvinylcinnamate binder (1:1) 1% solids in o-DCB. Average mobility=4.0×10$^{-5}$ cm$^2$Vs.

Figure 3:
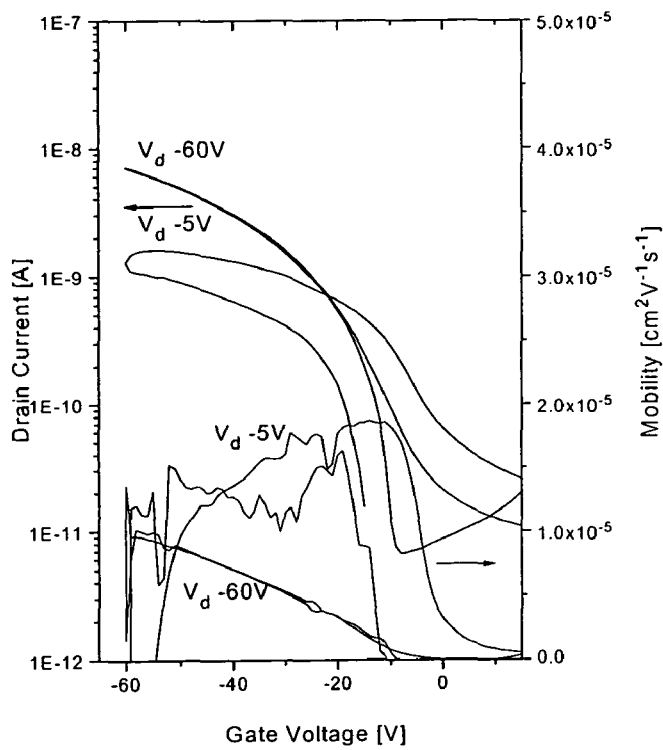

FIG. 3: Compound 3 (TIPS non conjugated pentacene dimer)+polyalphamethylstyrene binder (1:1) 4% solids in m-xylene. Average mobility=2.5×10$^{-5}$ cm$^2$Vs.

Figure 4:
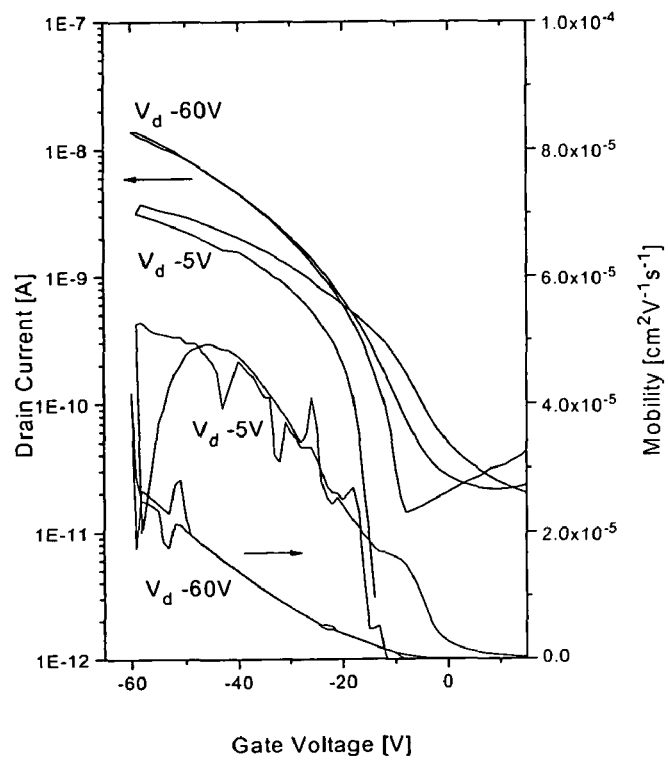

FIG. 4: Compound 4 (TIPS pentacene dimer ether)+polyalphamethylstyrene binder (1:1) 4% solids in m-xylene. Average mobility=5.0×10$^{-5}$ cm$^2$Vs.

The invention claimed is:
1. A compound of formula I

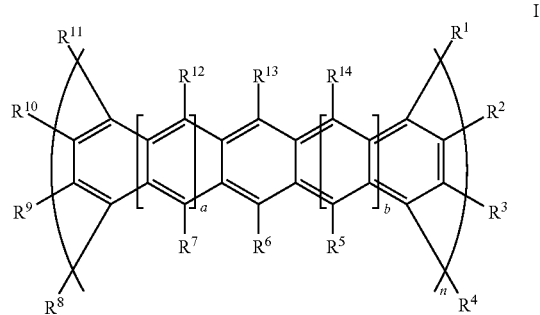

wherein
a is 1,
b is 1,
n is an integer ≧2,
R$^{1-14}$ denote, in case of multiple occurrence independently of one another, identical or different groups selected from the group consisting of H, halogen, —CN, —NC, —NCO, —NCS, —OCN, —SCN, —C(=O)NR$^o$R$^{oo}$, —C(=O)X, —C(=O)R$^o$, —NH$_2$, —NR$^o$R$^{oo}$, —SH, —SR$^o$, —SO$_3$H, —SO$_2$R$^o$, —OH, —NO$_2$, —CF$_3$, —SF$_5$, optionally substituted silyl, and carbyl and hydrocarbyl with 1 to 40 C atoms that is optionally substituted and optionally comprises one or more hetero atoms, $R^{1-4}$ and $R^{8-11}$ can also denote a linkage to an adjacent polyacene unit, wherein said linkage is a single bond or optionally contains a spacer group, X is halogen, and $R^0$ and $R^{00}$ are independently of each other H or an optionally substituted carbyl or hydrocarbyl group optionally comprising one or more hetero atoms, optionally two or more of the substituents $R^1$-$R^{14}$ which are located on adjacent ring positions of the polyacene or which are located on adjacent polyacene units, constitute a further saturated, unsaturated or aromatic ring system having 4 to 40 C atoms, which is monocyclic or polycyclic, is fused to the polyacene, is optionally intervened by one or more groups selected from the group consisting of —O—, —S—, =N— and —N($R^0$)—, and is optionally substituted by one or more identical or different groups $R^1$, optionally one or more of the carbon atoms in the polyacene skeleton or in the rings formed by $R^{1-14}$ are replaced by a heteroatom selected from the group consisting of N, P, As, O, S, Se and Te, wherein the n polyacene units are identical or different from each other, and a polyacene unit is linked to its adjacent polyacene unit(s) via one of $R^{1-4}$ and/or one of $R^{8-11}$, and/or a polyacene unit is optionally fused to its adjacent polyacene unit(s) via two of $R^{1-4}$ and/or two of $R^{8-11}$.

2. A compound according to claim 1, wherein n is 2 or 3.

3. A compound according to claim 1, which is one of the following formulae

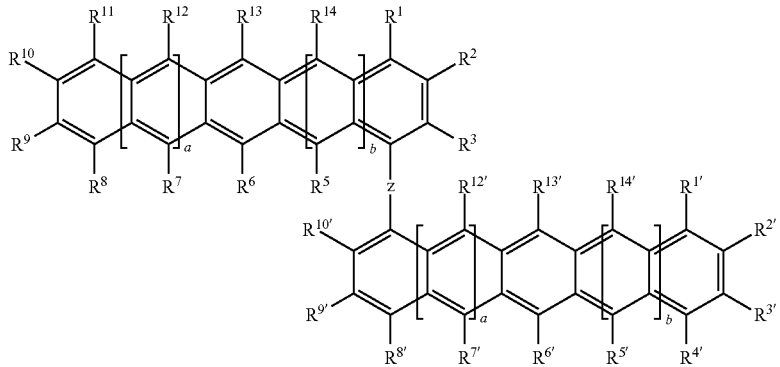

IA1

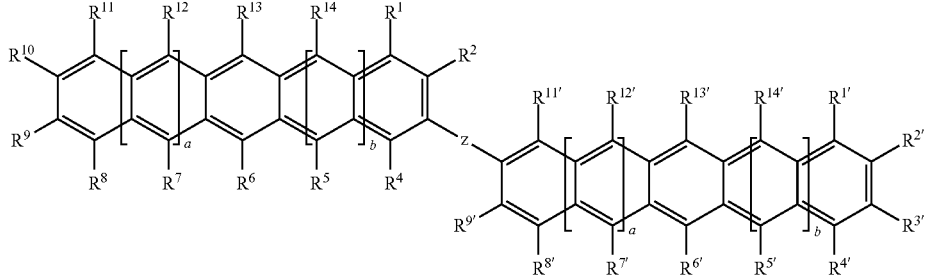

IA2

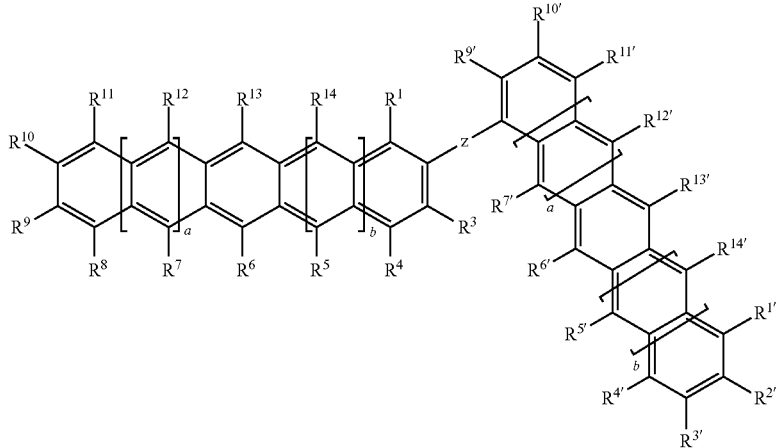

IA3

IA4
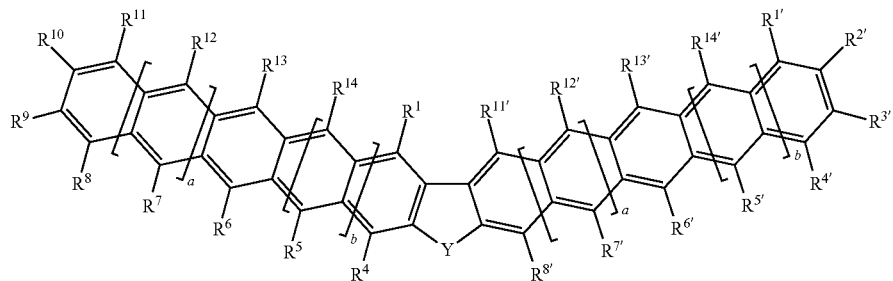
IA5
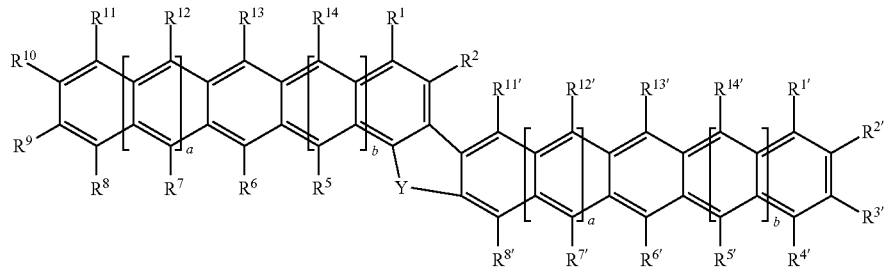
IA6
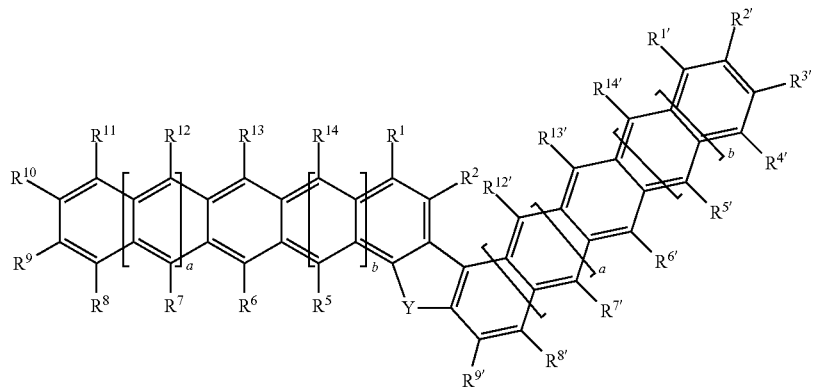
IB1
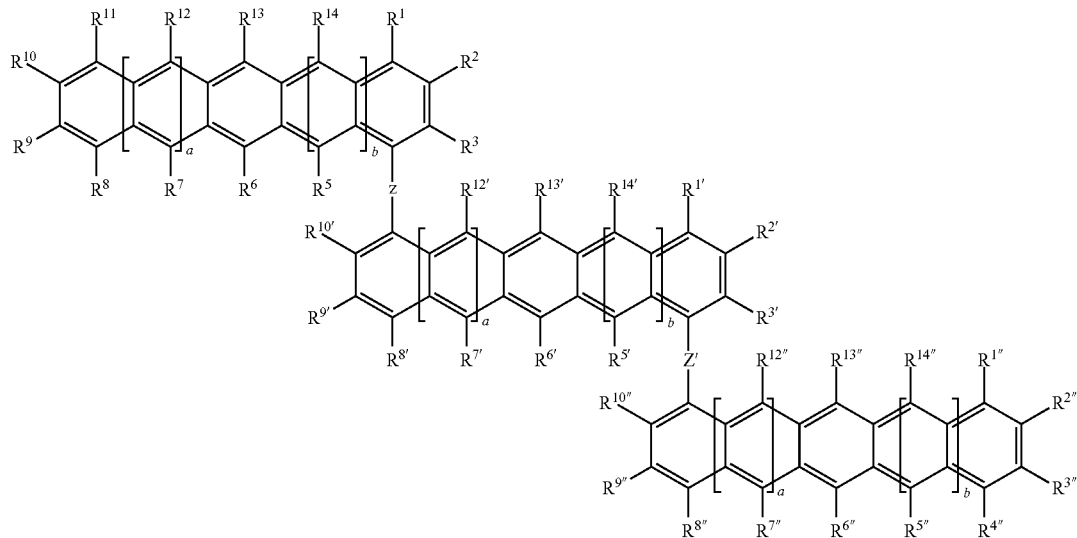

-continued
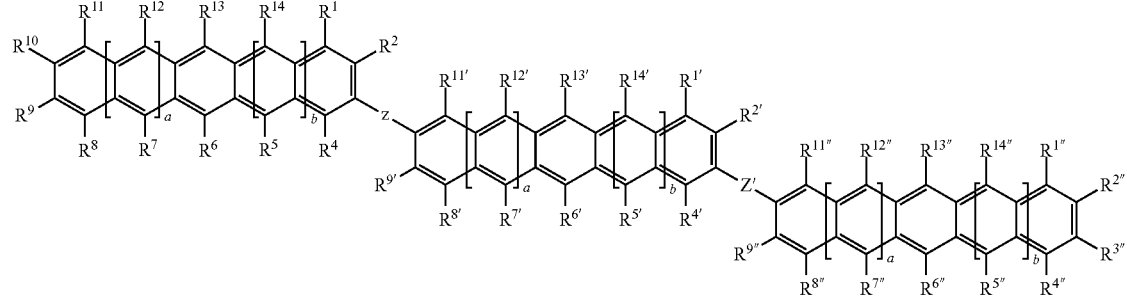
IB2
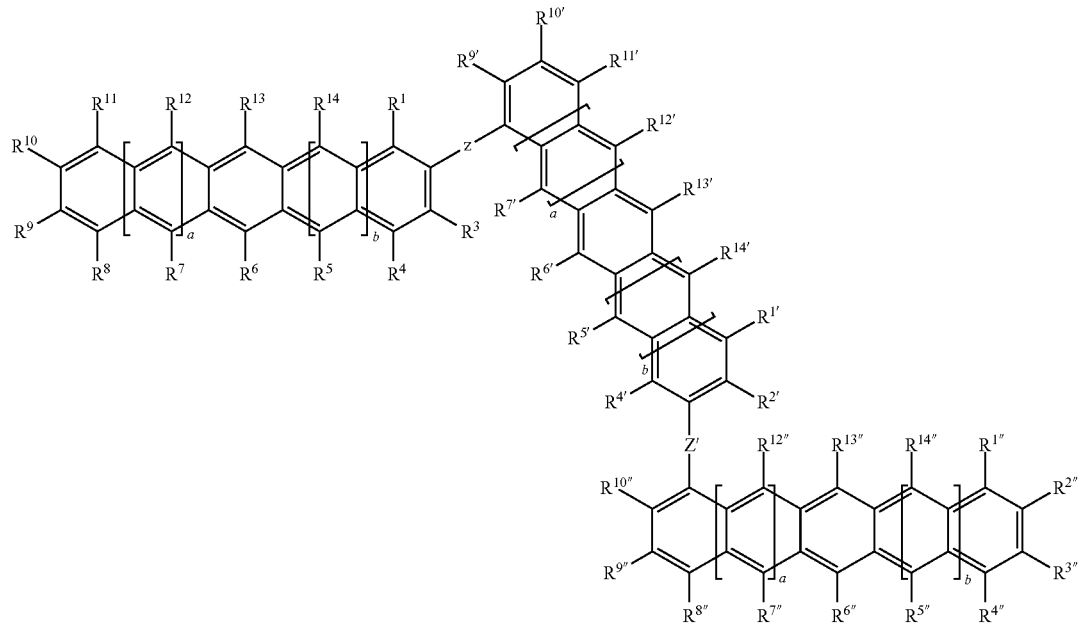
IB3
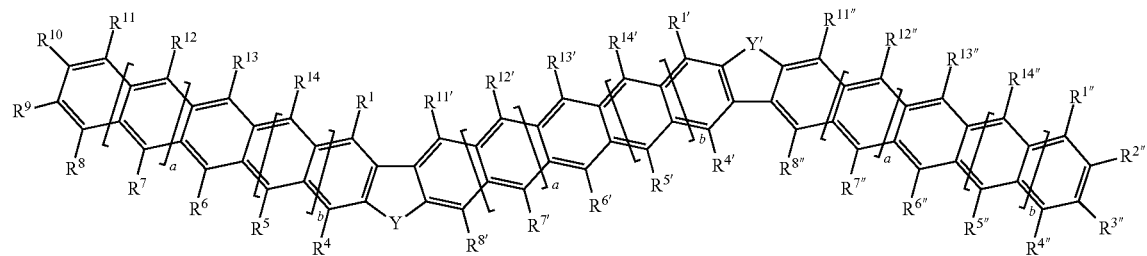
IB4
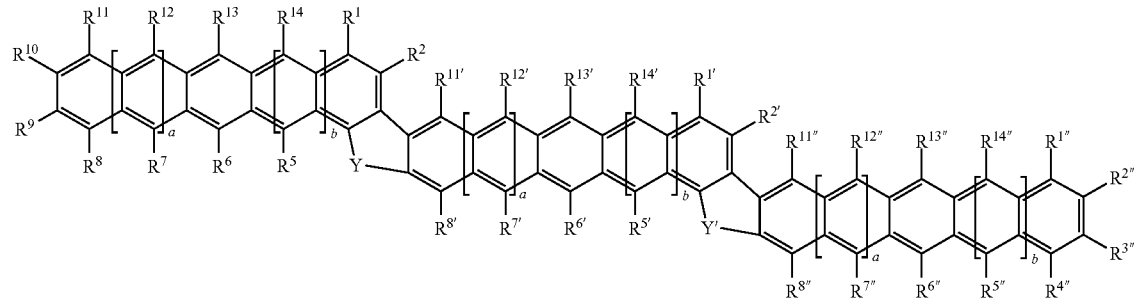
IB5

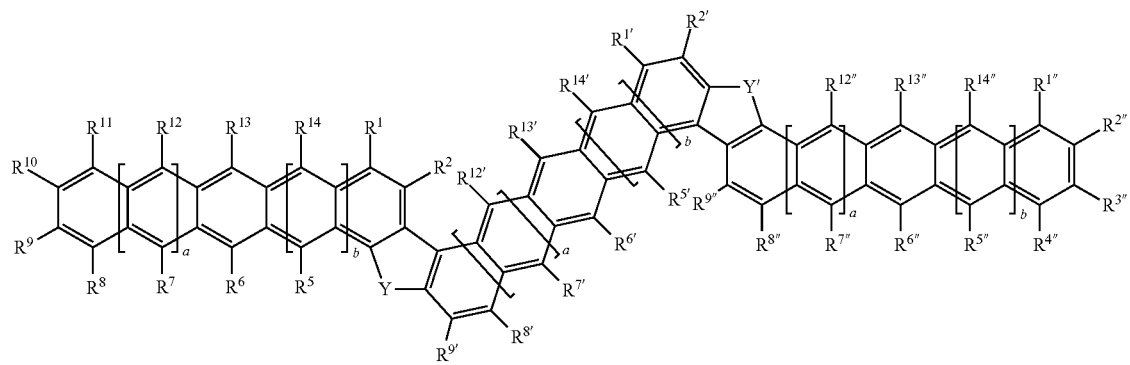

IB6

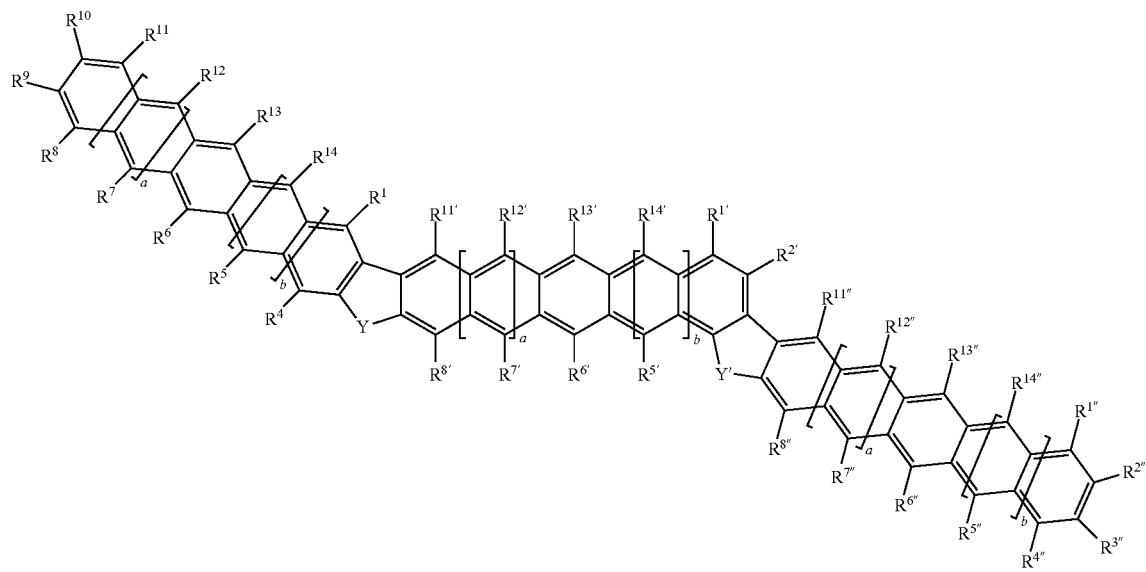

IB7 wherein
a, b, $R^{1-14}$ are as defined in formula I,
$R^{1'-14'}$ and $R^{1''-14''}$ have independently of each other one of the meanings of $R^1$,
Z, Z' are independently of each other a single bond or a spacer group,
Y, are independently of each other —$(CH_2)_k$—, —$CR^{15}$=$CR^{16}$—, —O—, —S—, —$CR^{16}$=N— or —N($R^0$)—,
$R^{15}$, $R^{16}$ have independently of each other one of the meanings of $R^1$,
$R^0$ is as defined in formula I, and
k is 1, 2 or 3.

4. A compound according to claim 3, wherein both $R^6$ and $R^{13}$ and/or both $R^{6'}$ and $R^{13'}$ and/or both $R^{6''}$ and $R^{13''}$ denote —C≡C-MR'R"R'" or —C≡C-MR'R"" wherein
M is Si or Ge,
R', R" and R'" are identical or different groups selected from the group consisting of H, a $C_1$-$C_{40}$-alkyl group, a $C_6$-$C_{40}$-aryl group, a $C_6$-$C_{40}$-arylalkyl group, a $C_1$-$C_{40}$-alkoxy group, and a $C_6$-$C_{40}$-arylalkyloxy group,
R"" forms a cyclic silyl alkyl group together with the M atom,
wherein all these groups are optionally substituted.

5. A compound according to claim 3, wherein both $R^9$ and $R^{10}$ and/or both $R^2$ and $R^3$ and/or both $R^{2'}$ and $R^{3'}$ and/or both $R^{2''}$ and $R^{3''}$ together with the respective polyacene unit form a 5-, 6- or 7-membered aromatic or heteroaromatic ring.

6. A compound according to claim 3, wherein both $R^9$ and $R^{10}$ and/or both $R^2$ and $R^3$ and/or both $R^{2'}$ and $R^{3'}$ and/or both $R^{2''}$ and $R^{3''}$ together with the respective polyacene unit form a 5-, 6- or 7-membered aromatic or heteroaromatic ring selected from the group consisting of pyridine, pyrimidine, thiophene, selenophene, thiazole, thiadiazole, oxazole and oxadiazole.

7. A compound according to claim 3, wherein both $R^9$ and $R^{10}$ and/or both $R^2$ and $R^3$ and/or both $R^{2'}$ and $R^{3'}$ and/or both $R^{2''}$ and $R^{3''}$ together with the respective polyacene unit form a 5-, 6- or 7-membered aromatic or heteroaromatic ring selected from the group consisting of the following groups or their mirror images

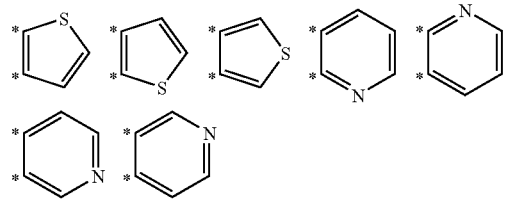

wherein the asterisks denote the positions where the respective group is fused to the polyacene.

8. A compound according to claim 3, wherein both $R^6$ and $R^{13}$ and/or both $R^{6'}$ and $R^{13'}$ and/or both $R^{6''}$ and $R^{13''}$ denote —C≡C-MR'R''R''' or —C≡C-MR'R'''', wherein
M is Si or Ge,
R', R'' and R''' are identical or different groups selected from the group consisting of H, a $C_1$-$C_{40}$-alkyl group, a $C_6$-$C_{40}$-aryl group, a $C_6$-$C_{40}$-arylalkyl group, a $C_1$-$C_{40}$-alkoxy group, and a $C_6$-$C_{40}$-arylalkyloxy group,
R'''' forms a cyclic silyl alkyl group together with the M atom.

9. A compound according to claim 1, which is one of the following formulae

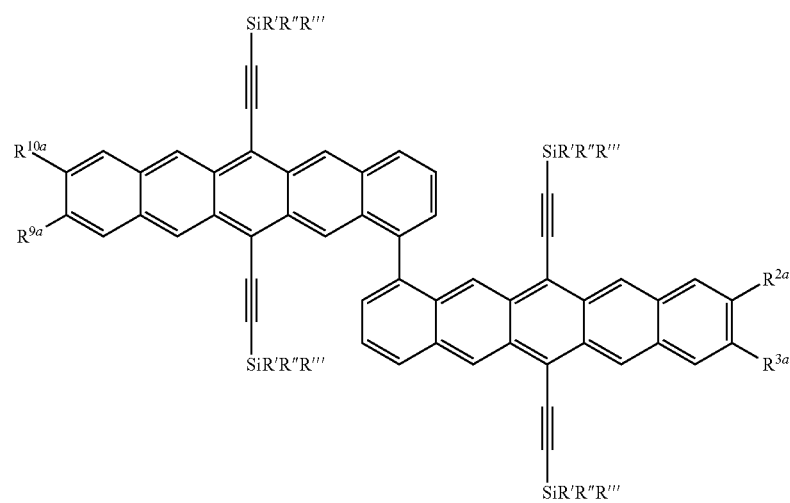

IA1a

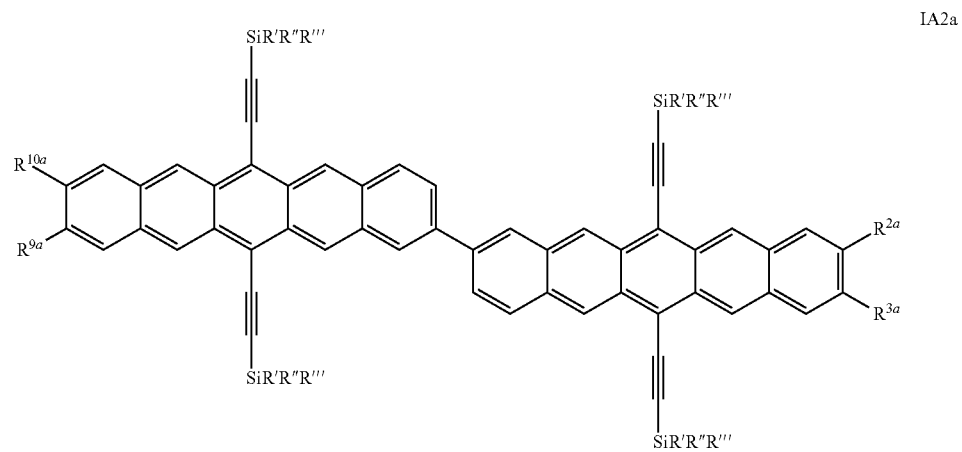

IA2a

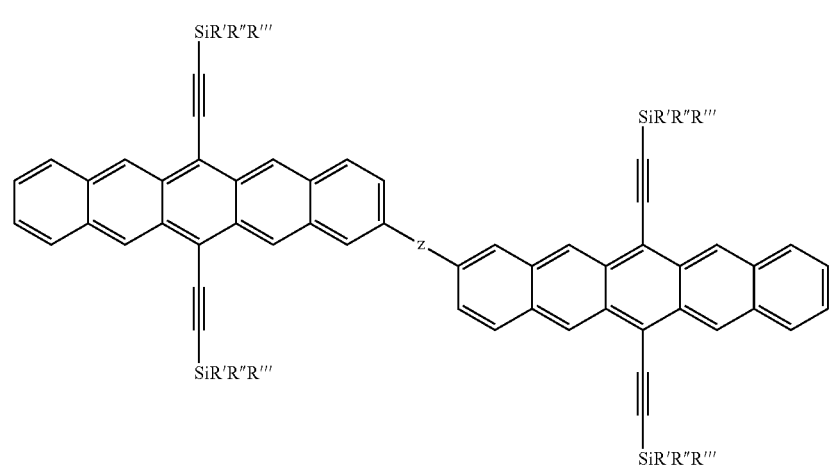

IA2d

-continued
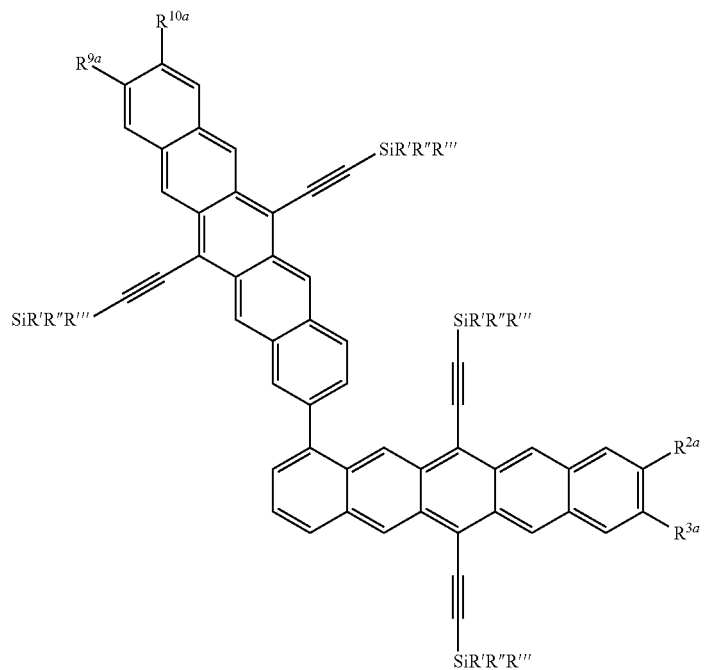
IA3a
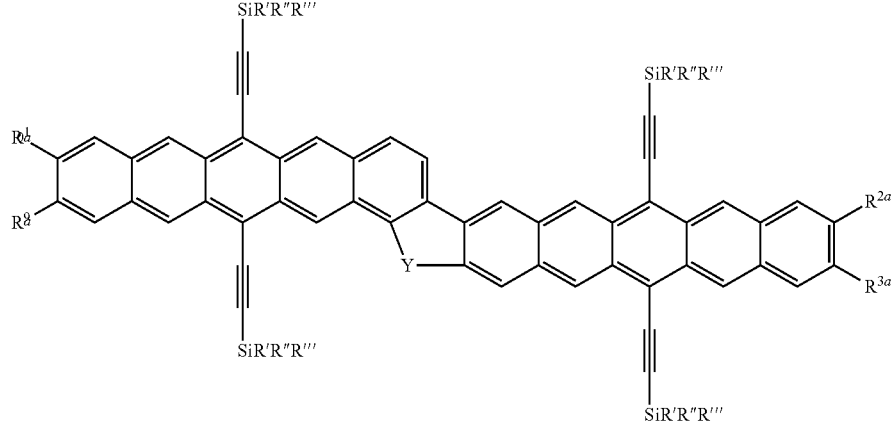
IA5a
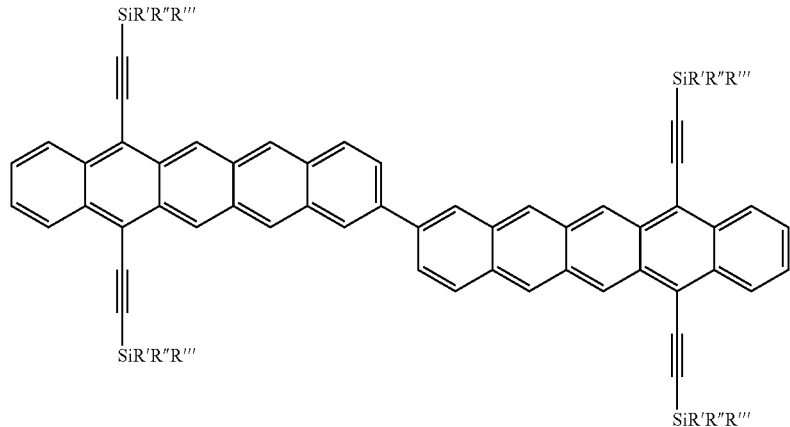
IA10a

-continued

IA11a

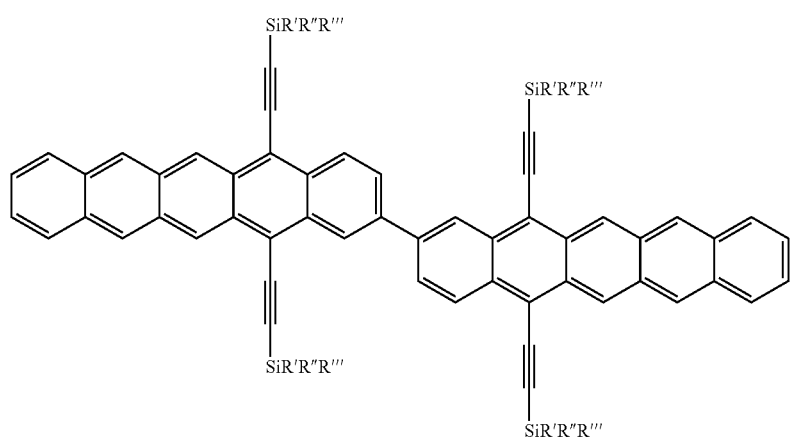

wherein

Z is a single bond or a spacer group,

Y is —(CH$_2$)$_k$—, —CR$^{15}$=CR$^{16}$—, —O—, —S—, —CR$^{16}$=N— or —N(R$^0$)—,

R', R" and R'" are identical or different groups selected from the group consisting of H, a C$_1$-C$_{40}$-alkyl group, a C$_6$-C$_{40}$-aryl group, a C$_6$-C$_{40}$-arylalkyl group, a C$_1$-C$_{40}$-alkoxy group, and a C$_6$-C$_{40}$-arylalkyloxy group, wherein all these groups are optionally substituted, R$^{2a,3a,9a,10a}$ have one of the meanings of R$^1$ as given for the compound of formula I, R$^0$ is as defined in formula I, and the phenylene rings are optionally substituted by one or more groups R$^1$ as defined for the compound of formula I.

10. A compound according to claim 9, wherein

R', R" and R'" are identical or different groups selected from the group consisting of H, a C$_1$-C$_{40}$-alkyl group, a C$_6$-C$_{40}$-aryl group, a C$_6$-C$_{40}$-arylalkyl group, a C$_1$-C$_{40}$-alkoxy group, and a C$_6$-C$_{40}$-arylalkyloxy group.

11. A compound according to claim 3, wherein the spacer group of the groups Z and Z' are selected from the group consisting of a) straight-chain, branched or cyclic alkylene with 1 to 20 C atoms which is optionally mono- or poly-substituted by F, Cl, Br, I or CN, and wherein one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, b) mono- or polycyclic aryl or heteroaryl with 1 to 40 C atoms which is optionally mono- or polysubstituted by one or more groups R$^1$ as defined in formula I, c) —O—, —S—, —CO—, —COO—, —OCO—, —O—COO—, —CO—NR$^0$—, —NR$^0$—CO—, —NR$^0$—CO—NR$^{00}$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CX$^1$=CX$^2$—, —CH=CH—COO—, or —OCO—CH=CH—, wherein R$^0$ and R$^{00}$ have the meanings given in formula I and X$^1$ and X$^2$ are selected from H, F, Cl and CN, and d) a combination of one or more groups selected from a), b) and c).

12. A compound according to claim 3, wherein Z and Z' denote a single bond.

13. A compound according to claim 3, wherein Y and Y' are independently of each other —O—, —S— or —N(R$^0$)—.

14. A formulation comprising one or more compounds according to claim 1, one or more organic polymers or organic polymeric binders, or precursors thereof, and optionally one or more solvents.

15. A formulation according to claim 14, wherein the organic binder has a permittivity ∈ at 1,000 Hz of 3.3 or less.

16. A formulation according to claim 14, which comprises one or more binders selected from the group consisting of styrene, α-methyl styrene, copolymers including one and more of styrene, α-methylstyrene and butadiene, and precursors thereof.

17. A formulation according to claim 14, comprising one or more organic solvents selected from the group consisting of dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetralin, decalin, indane and mixtures thereof.

18. An organic semiconducting layer, comprising one or more compounds according to claim 1 or formulations comprising one or more of said compounds, one or more organic polymers or organic polymeric binders, or precursors thereof, and optionally one or more solvents.

19. A process for preparing an organic semiconducting layer according to claim 18, comprising (i) depositing on a substrate a liquid layer of said one or more formulations, (ii) forming from the liquid layer a solid layer which is the organic semiconducting layer, (iii) optionally removing the layer from the substrate.

20. An OFET device comprising an organic semiconductor layer and further comprising a gate insulator layer, wherein the gate insulator layer comprises a fluoropolymer and/or the gate insulator layer is deposited from a formulation comprising an insulator material and one or more fluorosolvents, wherein the organic semiconductor layer is as defined in claim 18.

21. An electronic, optical or electrooptical component or device comprising one or more compounds according to claim 1, or formulations comprising one or more of said compounds, one or more organic polymers or organic polymeric binders, or precursors thereof, and optionally one or more solvents, or organic semiconducting layers, comprising one or more of said compounds or formulations.

22. An organic field effect transistor (OFET), thin film transistor (TFT), component of integrated circuitry (IC), radio frequency identification (RFID) tag, organic light emitting diode (OLED), electroluminescent display, flat panel display, backlight, photodetector, sensor, logic circuit, memory element, capacitor, photovoltaic (PV) cell, charge injection layer, Schottky diode, planarising layer, antistatic film, conducting substrate or pattern, photoconductor, electrophotographic element comprising one or more compounds according to claim 1, or formulations comprising one or more of said compounds, one or more organic polymers or organic polymeric binders, or precursors thereof, and optionally one or more solvents, or organic semiconducting layers, comprising one or more of said compounds or formulations.

23. An OFET device according to claim 22, which is a top gate OFET device.

24. An OFET device according to claim 22, which is a bottom gate OFET device.

25. A compound according to claim 1, wherein at least one of the following conditions is satisfied:
i) both $R^6$ and $R^{13}$ denote —C≡C-MR'R"R''' or —C≡C-MR'R"", wherein
M is Si or Ge,
R', R" and R''' are identical or different groups selected from the group consisting of H, a $C_1$-$C_{40}$-alkyl group, a $C_6$-$C_{40}$-aryl group, a $C_6$-$C_{40}$-arylalkyl group, a $C_1$-$C_{40}$-alkoxy group, and a $C_6$-$C_{40}$-arylalkyloxy group,
R"" forms a cyclic silyl alkyl group together with the M atom,
wherein all these groups are optionally substituted; or
ii) both $R^9$ and $R^{10}$ and/or both $R^2$ and $R^3$ together with the respective polyacene unit form a 5-, 6- or 7-membered aromatic or heteroaromatic ring.

26. A compound according to claim 25, wherein at least one of the following conditions is satisfied:
i) both $R^6$ and $R^{13}$ denote —C≡C-MR'R"R''' or —C≡C-MR'R"", wherein
M is Si or Ge,
R', R" and R''' are identical or different groups selected from the group consisting of H, a $C_1$-$C_{40}$-alkyl group, a $C_6$-$C_{40}$-aryl group, a $C_6$-$C_{40}$-arylalkyl group, a $C_1$-$C_{40}$-alkoxy group, and a $C_6$-$C_{40}$-arylalkyloxy group,
R"" forms a cyclic silyl alkyl group together with the M atom; or
ii) both $R^9$ and $R^{10}$ and/or both $R^2$ and $R^3$ together with the respective polyacene unit form a 5-, 6- or 7-membered aromatic or heteroaromatic ring.

27. A compound according to claim 1, wherein n is an integer 2, 3, 4, 5, 6, 7, 8, 9 or 10.

28. A compound according to claim 1, wherein
$R^{1-14}$ denote, in case of multiple occurrence independently of one another, identical or different groups selected from the group consisting of H, halogen, —CN, —NC, —NCO, —NCS, —OCN, —SCN, —C(=O)NR°R°°, —C(=O)X, —C(=O)R°, —NH₂, —NR°R°°, —SH, —SR°, —SO₃H, —SO₂R°, —OH, —NO₂, —CF₃, —SF₅, silyl, and carbyl and hydrocarbyl with 1 to 40 C atoms that optionally comprises one or more hetero atoms, and R° and R°° are independently of each other H or carbyl or hydrocarbyl group optionally comprising one or more hetero atoms,
wherein at least one of the following conditions is satisfied:
i) both $R^6$ and $R^{13}$ and/or both $R^{6'}$ and $R^{13'}$ and/or both $R^{6''}$ and $R^{13''}$ denote —C≡C-MR'R"R''' or —C≡C-MR'R"", wherein
M is Si or Ge,
R', R" and R''' are identical or different groups selected from the group consisting of H, a $C_1$-$C_{40}$-alkyl group, a $C_6$-$C_{40}$-aryl group, a $C_6$-$C_{40}$-arylalkyl group, a $C_1$-$C_{40}$-alkoxy group, and a $C_6$-$C_{40}$-arylalkyloxy group,
R"" forms a cyclic silyl alkyl group together with the M atom; or
ii) both $R^9$ and $R^{10}$ and/or both $R^2$ and $R^3$ and/or both $R^{2'}$ and $R^{3'}$ and/or both $R^{2''}$ and $R^{3''}$ together with the respective polyacene unit form a 5-, 6- or 7-membered aromatic or heteroaromatic ring.

29. A formulation comprising one or more compounds of formula I

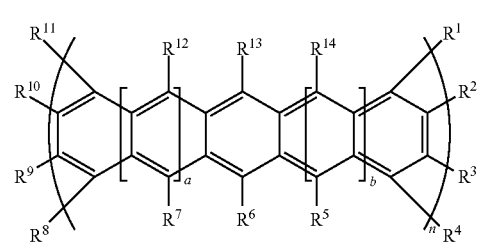

wherein
a is 1,
b is 1,
n is an integer ≧2,
$R^{1-14}$ denote, in case of multiple occurrence independently of one another, identical or different groups selected from the group consisting of H, halogen, —CN, —NC, —NCO, —NCS, —OCN, —SCN, —C(=O)NR°R°°, —C(=O)X, —C(=O)R°, —NH₂, —NR°R°°, —SH, —SR°, —SO₃H, —SO₂R°, —OH, —NO₂, —CF₃, —SF₅, silyl, optionally substituted silyl, and carbyl and hydrocarbyl with 1 to 40 C atoms that is optionally substituted and optionally comprises one or more hetero atoms,
$R^{1-4}$ and $R^{8-11}$ can also denote a linkage to an adjacent polyacene unit, wherein said linkage is a single bond or optionally contains a spacer group,
X is halogen, and
R° and R°° are independently of each other H or an optionally substituted carbyl or hydrocarbyl group optionally comprising one or more hetero atoms,
optionally two or more of the substituents $R^1$-$R^{14}$ which are located on adjacent ring positions of the polyacene or which are located on adjacent polyacene units, constitute a further saturated, unsaturated or aromatic ring system having 4 to 40 C atoms, which is monocyclic or polycyclic, is fused to the polyacene, is optionally intervened by one or more groups selected from the group consisting of —O—, —S—, =N— and —N(R°)—, and is optionally substituted by one or more identical or different groups $R^1$,
optionally one or more of the carbon atoms in the polyacene skeleton or in the rings formed by $R^{1-14}$ are replaced by a heteroatom selected from the group consisting of N, P, As, O, S, Se and Te,
wherein
the n polyacene units are identical or different from each other, and
a polyacene unit is linked to its adjacent polyacene unit(s) via one of $R^{1-4}$ and/or one of $R^{8-11}$, and/or
a polyacene unit is optionally fused to its adjacent polyacene unit(s) via two of $R^{1-4}$ and/or two of $R^{8-11}$,
one or more organic polymers or organic polymeric binders, or precursors thereof,
and optionally one or more solvents;
wherein at least one of the following conditions is satisfied:
i) the organic binder has a permittivity ∈ at 1,000 Hz of 3.3 or less,
ii) comprises one or more binders selected from the group consisting of styrene, α-methyl styrene, copolymers including one and more of styrene, α-methylstyrene and butadiene, and precursors thereof,
iii) comprises one or more organic solvents selected from the group consisting of dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetralin, decalin, indane and mixtures thereof.

30. A formulation according to claim 29, wherein the organic binder has a permittivity ∈ at 1,000 Hz of 3.3 or less.

31. A formulation according to claim 29, which comprises one or more binders selected from the group consisting of styrene, α-methyl styrene, copolymers including one and more of styrene, α-methylstyrene and butadiene, and precursors thereof.

32. A formulation according to claim 29, comprising one or more organic solvents selected from the group consisting of dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetralin, decalin, indane and mixtures thereof.

33. A formulation according to claim 29, wherein $R^{1-14}$ denote, in case of multiple occurrence independently of one another, identical or different groups selected from the group consisting of H, halogen, —CN, —NC, —NCO, —NCS, —OCN, —SCN, —C(=O)NR°R°°, —C(=O)X, —C(=O)R°, —NH₂, —NR°R°°, —SH, —SR°, —SO₃H, —SO₂R°, —OH, —NO₂, —CF₃, —SF₅, silyl, and carbyl and hydrocarbyl with 1 to 40 C atoms that optionally comprises one or more hetero atoms, and
R° and R°° are independently of each other H or carbyl or hydrocarbyl group optionally comprising one or more hetero atoms.

34. A compound of formula I

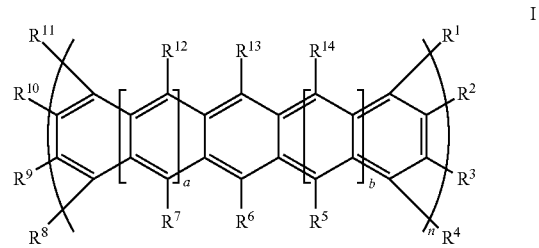

wherein
a is 1,
b is 1,
n is an integer ≧2,
$R^{1-14}$ denote, in case of multiple occurrence independently of one another, identical or different groups selected from the group consisting of H, halogen, —CN, —NC, —NCO, —NCS, —OCN, —SCN, —C(=O)NR°R°°, —C(=O)X, —C(=O)R°, —NH₂, —NR°R°°, —SH, —SR°, —SO₃H, —SO₂R°, —OH, —NO₂, —CF₃, —SF₅, optionally substituted silyl, and carbyl and hydrocarbyl with 1 to 40 C atoms that is optionally substituted and optionally comprises one or more hetero atoms,
$R^{1-4}$ and $R^{8-11}$ can also denote a linkage to an adjacent polyacene unit, wherein said linkage is a single bond or optionally contains a spacer group,
X is halogen, and
R° and R°° are independently of each other H or an optionally substituted carbyl or hydrocarbyl group optionally comprising one or more hetero atoms,
wherein
the n polyacene units are identical or different from each other, and
a polyacene unit is linked to its adjacent polyacene unit(s) via one of $R^{1-4}$ and/or one of $R^{8-11}$, and/or
a polyacene unit is optionally fused to its adjacent polyacene unit(s) via two of $R^{1-4}$ and/or two of $R^{8-11}$.

* * * * *

UNITED STATES PATENT AND TRADEMARK OFFICE
CERTIFICATE OF CORRECTION

PATENT NO. : 7,985,353 B2
APPLICATION NO. : 11/915061
DATED : July 26, 2011
INVENTOR(S) : Leeming et al.

It is certified that error appears in the above-identified patent and that said Letters Patent is hereby corrected as shown below:

Title Page, item (54) reads "OLIGOMERIC IS POLYACENE AND SEMICONDUCTOR FORMULATIONS" should read --OLIGOMERIC POLYACENE AND SEMICONDUCTOR FORMULATIONS--

Column 80, line 49 should read --35. A compound according to claim 1, wherein
$R^{1-14}$ denote, in case of multiple occurrence independently of one another, identical or different groups selected from the group consisting of H, halogen, -CN, -NC, -NCO, -NCS, -OCN, -SCN, -C(=O)NR$^0$R$^{00}$, -C(=O)X, -C(=O)R$^0$, -NH$_2$, -NR$^0$R$^{00}$, -SH, -SR$^0$, -SO$_3$H, -SO$_2$R$^0$, -OH, -NO$_2$, -CF$_3$, -SF$_5$, optionally substituted silyl, and carbyl and hydrocarbyl with 1 to 40 C atoms that is optionally substituted and optionally comprises one or more hetero atoms, $R^{1-4}$ and $R^{8-11}$ can also denote a linkage to an adjacent polyacene unit, wherein said linkage is a single bond or contains a spacer group, which spacer group is selected from the group consisting of a) straight-chain, branched or cyclic alkylene with 1 to 20 C atoms which is optionally mono- or poly-substituted by F, Cl, Br, I or CN, and wherein one or more non-adjacent CH$_2$ groups are optionally replaced, in each case independently from one another, by -O-, -S-, -NH-, -NR$^0$-, -SiR$^0$R$^{00}$-, -CO-, -COO-, -OCO-, -OCO-O-, -S-CO-, -CO-S-, -CH=CH- or -C≡C- in such a manner that O and/or S atoms are not linked directly to one another, b) mono- or polycyclic aryl or heteroaryl with 1 to 40 C atoms which is optionally mono- or polysubstituted by one or more groups $R^1$ as defined in formula I, c) -O-, -S-, -CO-, -COO-, -OCO-, -O-COO-, -CO-NR$^0$-, -NR$^0$-CO-, -NR$^0$-CO-NR$^{00}$-, -OCH$_2$-, -CH$_2$O-, -SCH$_2$-, -CH$_2$S-, -CF$_2$O-, -OCF$_2$-, -CF$_2$S-, -SCF$_2$-, -CF$_2$CH$_2$-, -CH$_2$CF$_2$-, -CF$_2$CF$_2$-, -CH=N-, -N=CH-, -N=N-, -CH=CR$^0$-, -CX$^1$=CX$^2$-, -C≡C-, -CH=CH-COO-, or -OCO-CH=CH-, wherein R$^0$ and R$^{00}$ have the meanings given in formula I and X$^1$ and X$^2$ are selected from H, F, Cl and CN, and d) a combination of one or more groups selected from a), b) and c).--

Signed and Sealed this
Twenty-first Day of February, 2012

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,985,353 B2 |
| APPLICATION NO. | : 11/915061 |
| DATED | : July 26, 2011 |
| INVENTOR(S) | : Leeming et al. |

It is certified that error appears in the above-identified patent and that said Letters Patent is hereby corrected as shown below:

Title Page, item (54) and at Column 1, lines 1 and 2, Title reads "OLIGOMERIC IS POLYACENE AND SEMICONDUCTOR FORMULATIONS" should read --OLIGOMERIC POLYACENE AND SEMICONDUCTOR FORMULATIONS--

Column 80, line 49 should read --35.    A compound according to claim 1, wherein
$R^{1-14}$ denote, in case of multiple occurrence independently of one another, identical or different groups selected from the group consisting of H, halogen, -CN, -NC, -NCO, -NCS, -OCN, -SCN, -C(=O)NR$^0$R$^{00}$, -C(=O)X, -C(=O)R$^0$, -NH$_2$, -NR$^0$R$^{00}$, -SH, -SR$^0$, -SO$_3$H, -SO$_2$R$^0$, -OH, -NO$_2$, -CF$_3$, -SF$_5$, optionally substituted silyl, and carbyl and hydrocarbyl with 1 to 40 C atoms that is optionally substituted and optionally comprises one or more hetero atoms, $R^{1-4}$ and $R^{8-11}$ can also denote a linkage to an adjacent polyacene unit, wherein said linkage is a single bond or contains a spacer group, which spacer group is selected from the group consisting of
   a)    straight-chain, branched or cyclic alkylene with 1 to 20 C atoms which is optionally mono- or poly-substituted by F, Cl, Br, I or CN, and wherein one or more non-adjacent CH$_2$ groups are optionally replaced, in each case independently from one another, by -O-, -S-, -NH-, -NR$^0$-, -SiR$^0$R$^{00}$-, -CO-, -COO-, -OCO-, -OCO-O-, -S-CO-, -CO-S-, -CH=CH- or -C≡C- in such a manner that O and/or S atoms are not linked directly to one another,
   b)    mono- or polycyclic aryl or heteroaryl with 1 to 40 C atoms which is optionally mono- or polysubstituted by one or more groups $R^1$ as defined in formula I, This certificate supersedes the Certificate of Correction issued February 21, 2012.

Signed and Sealed this
Twentieth Day of March, 2012

David J. Kappos
*Director of the United States Patent and Trademark Office* c) $-O-$, $-S-$, $-CO-$, $-COO-$, $-OCO-$, $-O-COO-$, $-CO-NR^0-$, $-NR^0-CO-$, $-NR^0-CO-NR^{00}-$, $-OCH_2-$, $-CH_2O-$, $-SCH_2-$, $-CH_2S-$, $-CF_2O-$, $-OCF_2-$, $-CF_2S-$, $-SCF_2-$, $-CF_2CH_2-$, $-CH_2CF_2-$, $-CF_2CF_2-$, $-CH=N-$, $-N=CH-$, $-N=N-$, $-CH=CR^0-$, $-CX^1=CX^2-$, $-C\equiv C-$, $-CH=CH-COO-$, or $-OCO-CH=CH-$, wherein $R^0$ and $R^{00}$ have the meanings given in formula I and $X^1$ and $X^2$ are selected from H, F, Cl and CN, and d) a combination of one or more groups selected from a), b) and c).--